United States Patent
Wyent et al.

(10) Patent No.: US 11,738,092 B2
(45) Date of Patent: Aug. 29, 2023

(54) METHODS AND COMPOSITIONS FOR SYNTHESIS OF THERAPEUTIC NANOPARTICLES

(71) Applicant: Dantari, Inc., Thousand Oaks, CA (US)

(72) Inventors: Emily A. Wyent, Sherman Oaks, CA (US); Carl M. Blumenfeld, West Hills, CA (US); Robert J. Lamm, Thousand Oaks, CA (US)

(73) Assignee: Dantari, Inc., Thousand Oaks, CA (US)

( * ) Notice: Subject to any disclaimer, the term of this patent is extended or adjusted under 35 U.S.C. 154(b) by 187 days.

(21) Appl. No.: 17/112,288

(22) Filed: Dec. 4, 2020

(65) Prior Publication Data

US 2021/0170049 A1 Jun. 10, 2021

Related U.S. Application Data

(60) Provisional application No. 62/943,594, filed on Dec. 4, 2019, provisional application No. 63/110,182, filed on Nov. 5, 2020.

(51) Int. Cl.
*A61K 47/69* (2017.01)
*C07D 491/22* (2006.01)
*A61K 47/60* (2017.01)
*C07F 5/02* (2006.01)
*C07F 7/08* (2006.01)
*A61K 47/54* (2017.01)

(52) U.S. Cl.
CPC ........ *A61K 47/6929* (2017.08); *A61K 47/549* (2017.08); *A61K 47/60* (2017.08); *C07D 491/22* (2013.01); *C07F 5/025* (2013.01); *C07F 7/0814* (2013.01)

(58) Field of Classification Search
CPC ....... A61K 47/60; A61K 47/62; C07D 491/22
See application file for complete search history.

(56) References Cited

U.S. PATENT DOCUMENTS

| | | | |
|---|---|---|---|
| 4,631,190 A | 12/1986 | Shen et al. | |
| 5,948,878 A | 9/1999 | Burgess et al. | |
| 6,007,845 A | 12/1999 | Domb et al. | |
| 8,557,292 B2 | 10/2013 | Davis et al. | |
| 8,968,714 B2 | 3/2015 | Davis et al. | |
| 9,446,149 B2 | 9/2016 | Davis et al. | |
| 9,468,681 B2 | 10/2016 | Davis et al. | |
| 10,166,291 B2 | 1/2019 | Davis et al. | |
| 10,182,986 B2 | 1/2019 | Wiley et al. | |
| 10,287,401 B2 | 5/2019 | Davis et al. | |
| 2002/0061288 A1 | 5/2002 | Hubbell et al. | |
| 2004/0126838 A1 | 7/2004 | DeFrees et al. | |
| 2004/0220146 A1 | 11/2004 | Freeman et al. | |
| 2006/0078997 A1 | 4/2006 | Lugade et al. | |
| 2008/0099172 A1 | 5/2008 | Pelton et al. | |
| 2010/0040556 A1 | 2/2010 | Davis et al. | |
| 2010/0069500 A1 | 3/2010 | Dhal et al. | |
| 2010/0166865 A1 | 7/2010 | Kumar et al. | |
| 2011/0086431 A1 | 4/2011 | Lugade et al. | |
| 2012/0064107 A1 | 3/2012 | Eliasof | |
| 2012/0225129 A1 | 9/2012 | Eliasof et al. | |
| 2012/0259021 A1 | 10/2012 | Jiang et al. | |
| 2012/0309691 A1 | 12/2012 | Zhou et al. | |
| 2012/0328564 A1 | 12/2012 | Govindan et al. | |
| 2014/0249202 A1 | 9/2014 | Davis et al. | |
| 2014/0249203 A1 | 9/2014 | Davis et al. | |
| 2014/0348754 A1 | 11/2014 | Wiley et al. | |
| 2015/0031832 A1 | 1/2015 | Davis et al. | |
| 2015/0376237 A1 | 12/2015 | Borros et al. | |
| 2017/0071857 A1 | 3/2017 | Wiley et al. | |
| 2019/0117773 A1 | 4/2019 | Davis et al. | |
| 2019/0381188 A1* | 12/2019 | Davis ................. | A61K 31/4045 |

FOREIGN PATENT DOCUMENTS

| | | |
|---|---|---|
| CN | 104530413 A | 4/2015 |
| CN | 106279286 A | 1/2017 |
| EP | 2341774 B1 | 12/2013 |
| EP | 3459546 A1 | 3/2019 |
| EP | 3459546 B1 | 1/2022 |
| WO | WO 2001/070275 A2 | 9/2001 |
| WO | WO 2010/019718 A2 | 2/2010 |
| WO | WO 2011/072133 A1 | 6/2011 |
| WO | WO 2011/159161 A2 | 12/2011 |
| WO | WO 2012/158622 A2 | 11/2012 |
| WO | WO 2017/177055 A1 | 10/2017 |

OTHER PUBLICATIONS

Han (Bioconjugate Chemistry; 2013, 24, 669-677).*
International Patent Application No. PCT/US2013/028681; Int'l Search Report; dated May 17, 2013; 3 pages.
International Patent Application No. PCT/US2013/028681; Int'l Preliminary Report on Patentability; dated Sep. 1, 2015; 6 pages.
International Patent Application No. PCT/US2013/028663; Int'l Search Report; dated Jun. 12, 2013; 4 pages.
International Patent Application No. PCT/US2013/028663; Int'l Preliminary Report on Patentability; dated Sep. 1, 2015; 7 pages.
Sapsford et al.; "Functionalizing nanoparticles with biological molecules: Developing chemistries that facilitate nanotechnology"; Chemical Reviews; vol. 113 No. 3; 2013; p. 1904-2074 (abstract only).
International Patent Application No. PCT/US2014/000099; Int'l Search Report; dated Aug. 19, 2014; 3 pages.
International Patent Application No. PCT/US2014/000099; Int'l Preliminary Report on Patentability; dated Nov. 17, 2015; 9 pages.
International Patent Application No. PCT/US2015/024619; Int'l Search Report; dated Jul. 23, 2015; 6 pages.

(Continued)

*Primary Examiner* — Pancham Bakshi
(74) *Attorney, Agent, or Firm* — BakerHostetler

(57) ABSTRACT

Improved methods and reactants for the chemical synthesis of therapeutic nanoparticles are provided. The nanoparticles comprise a polymeric core, to which is attached one or more homing molecules and one or more therapeutic agents. Improvements in speed, yield and purity are attained using the methods disclosed herein.

17 Claims, No Drawings

(56) References Cited

OTHER PUBLICATIONS

Konkimalla et al.; "Inhibition of epidermal growth factor receptor-overexpressing cancer cells by camptothecin, 20-(N,N-diethyl) glycinate"; Biochemical Pharmacology; vol. 80; Jul. 2010; p. 39-49.
Han et al.; "Targeted Nanoparticles Assembled via Complexation of Boronic-Acid-Containing Targeting Moieties to Diol-Containing Polymers"; Bioconjugate Chem; vol. 24 No. 4; Apr. 2013; p. 669-677.
Han et al.; "Single-Antibody, Targeted Nanoparticle Delivery of Camptothecin"; Mol. Pharmaceutics; vol. 10 No. 7; Jul. 2013; p. 2558-2567.
"*Homo sapiens* epidermal growth factor receptor (EGFR), transcript variant 1, mRNA"; NCBI GenBank Accession No. NM_005228.3; Apr. 6, 2014; accessed Mar. 24, 2022; 8 pages.
International Patent Application No. PCT/US2015/024619; Int'l Preliminary Report on Patentability; dated Oct. 12, 2016; 8 pages.
International Patent Application No. PCT/US2016/037166; Int'l Search Report; dated Sep. 12, 2016; 5 pages.
Gu et al.; "Cationic amphiphilic macromolecule (CAM)—lipid complexes for efficient siRNA gene silencing"; Journal of Controlled Release; vol. 184; Jun. 2014; p. 28-35.
Wu et al.; "Recent progress in copolymer-mediated siRNA delivery"; Journal of Drug Targeting; vol. 20 No. 7; 2012; p. 551-560 (abstract only).
Pan et al.; "Cationic Mucic Acid Polymer-Based siRNA Delivery Systems"; Bioconjugate Chemistry; vol. 26 No. 8; 2015; p. 1791-1803.
International Patent Application No. PCT/US2016/037166; Int'l Preliminary Report on Patentability; dated Jan. 2, 2018; 8 pages.
International Patent Application No. PCT/US2019/036682; Int'l Search Report; dated Sep. 16, 2019; 2 pages.
International Patent Application No. PCT/US2019/036682; Int'l Preliminary Report on Patentability; dated Dec. 15, 2020; 4 pages.
Metcalf III et al.; "In Vitro and In Vivo Studies Demonstrating Sustained Drug Release for Multiple Anticancer Payloads and Improved Anticancer Effects of a Cabazitaxel β-Cyclodextrin-PEG Copolymer-Based Nanoparticle-Drug Conjugate (NDC)"; Abstract No. B176; AACR Int'l Conf. on Molecular Targets and Cancer Therapeutics; Nov. 2015; one page.
Metcalf III et al.; "Significant Improvements in Therapeutic Index for Conjugated Payloads Using a Nanoparticle-Drug Conjugate (NDC) Platform to Provide Sustained Drug Release and Potentially Improved Anticancer Effects"; Abstract No. B43; AACR Special Conf. on Engineering and Physical Sciences in Oncology; Jun. 2016; one page.
Sapra et al.; "Novel Delivery of SN38 Markedly Inhibits Tumor Growth in Xenografts, Including a Camptothecin-11-Refractory Model"; Clinical Cancer Res; vol. 14(6); Mar. 2008; p. 1888-1896.
Sepehri et al.; "Human Serum Albumin Conjugates of 7-Ethyl-10-hydroxycamptothecin (SN38) for Cancer Treatment"; BioMed Research Int'l; vol. 2014 Article ID 963507; 2014; 11 pages.
International Patent Application No. PCT/US2020/063321; Int'l Search Report and the Written Opinion; dated Mar. 17, 2021; 12 pages.
International Patent Application No. PCT/US2009/053620; Int'l Written Opinion and Search Report; dated Apr. 2, 2010; 11 pages.
International Patent Application No. PCT/US2009/053620; Int'l Preliminary Report on Patentability; dated Feb. 15, 2011; 7 pages.
International Patent Application No. PCT/US2020/063321; Int'l Preliminary Report on Patentability; dated Jun. 16, 2022; 7 pages.

\* cited by examiner

METHODS AND COMPOSITIONS FOR SYNTHESIS OF THERAPEUTIC NANOPARTICLES

CROSS REFERENCE TO RELATED APPLICATIONS

This application claims the benefit, under 35 U.S.C. § 119(e)(1), of U.S. Provisional Patent Application No. 62/943,594 filed Dec. 4, 2019 and U.S. Provisional Patent Application No. 63/110,182 filed Nov. 5, 2020; the disclosures of both of which are hereby incorporated by reference, in their entireties, for all purposes.

STATEMENT REGARDING FEDERAL SUPPORT

Not applicable.

FIELD

The present disclosure is in the field of nanoparticles for treatment of various cancers, wherein said nanoparticles comprise a polymeric core, further comprising one or more homing molecules (i.e., targeting molecules) and/or one or more therapeutic molecules. Improved methods for synthesis of such nanoparticles are provided herein.

BACKGROUND

Treatment of many brain disorders such as brain cancer and metastases to the brain requires that therapeutic molecules be delivered to the brain. Direct delivery of therapeutics to the brain poses severe risks to the subject (e.g., breaching the skull), and cannot be feasibly carried out on a continuing basis, as is required for most chemotherapeutic treatments. However, systemic delivery (e.g., via the bloodstream) will not efficiently deliver molecules to the brain, because of the existence of the blood-brain barrier (BBB); a tightly-joined layer of endothelial cells lining the blood vessels of the brain. A similar permeation barrier, known as the blood-tumor barrier (BTB) exists in certain solid tumors.

Cancers of the breast frequently metastasize to the brain and these brain metastases could be treated with chemotherapeutic molecules used for treatment of breast cancer, if the therapeutic could be delivered to the brain in sufficient concentrations. One such chemotherapeutic is camptothecin, an alkaloid that inhibits DNA topoisomerase I, thereby preventing cell division. Due to problems with the solubility of camptothecin in aqueous environments, such as the cell cytoplasm, derivatives of camptothecin with greater solubility have been developed. One such derivative is 7-ethyl-10-hydroxy-camptothecin (SN38), which was originally discovered as a metabolite of the camptothecin analogue irinotecan.

To address the problem of delivering therapeutics across the BBB and the BTB, nanoparticles containing chemotherapeutic molecules and homing (i.e., targeting) molecules have been developed in which the homing molecule binds to the transferrin receptor present on the surface of brain endothelial cells (and endothelial cells of tumor vasculature), which allows the nanoparticle to cross the endothelial cell by transcytosis. See, for example, U.S. Pat. Nos. 9,468,681; 10,166,291 and 10,182,986. Each of these patents are incorporated by reference herein for all purposes, or at least for their teachings of the nature of the nanoparticles, their methods of making and use, and their modes of operation.

Certain steps in the synthesis of such nanoparticles are (1) conversion of mucic acid to a reactive derivative capable of polymerization (i.e., a "mucic acid monomer" or MAM), (2) polymerization of the mucic acid monomer to form a mucic acid polymer (MAP), (3) conversion of the therapeutic molecule to a selectively reactive derivative, and (4) attachment of one or more of the derivatized therapeutic molecules to the MAP.

Nanoparticles containing camptothecin (CPT), that are capable of crossing the blood-brain barrier and the blood tumor barrier, have been described. See, for example, U.S. Pat. Nos. 9,446,149; 9,468,681; 10,166,291 and U.S. Patent Application Publication No. 2019/0381188 (Dec. 19, 2019); each of which is incorporated by reference herein for all purposes or at least for the descriptions of the nanoparticles. However, existing methods for preparing such nanoparticles are reagent- and time-intensive, require elevated temperatures, and provide low yields. Moreover, as noted above, derivatives of CPT that are more highly soluble under aqueous conditions would be preferred. Accordingly, there is a need for improved methods for the synthesis of nanoparticles containing chemotherapeutics such as CPT and its derivatives such as SN38, wherein the methods are rapid, economical in terms of reactants, and provide high yields.

In addition, treatment of non-CNS malignancies such as non-CNS tumors and hematologic malignancies would benefit from improved vehicles for delivery of chemotherapeutics.

SUMMARY

Provided herein are improved methods for synthesis of therapeutic nanoparticles comprising mucic acid-polyethylene glycol (PEG) polymers and chemotherapeutic drugs, such as camptothecin (CPT) and its derivatives and metabolites, such as 7-ethyl-10-hydroxy-camptothecin (SN38). The improvements include, inter alia, new intermediates, use of more stable reactants, formation of more stable intermediates, more rapid reaction times, higher yields of intermediates and products, and new linkers for conjugation of targeting (homing) molecules and therapeutic molecules (e.g., large molecule therapeutics; e.g., antibodies) to the nanoparticles. Derivatized nanoparticles (e.g., containing conjugated CPT or SN38 molecules), for use in the methods described herein, are also provided; as are mucic acid polymer (MAP) conjugates (e.g., MAPs conjugated to CPT, SN38, transferrin and/or trastuzumab) for use in assembling therapeutic nanoparticles.

Accordingly, provided herein are, inter alia, the following embodiments:

1. A method for synthesizing mucic acid di(aspartyl amine) di-trifluoroacetate from mucic acid diaminochloride, the method comprising:
    (a) converting mucic acid diaminochloride having the structure:

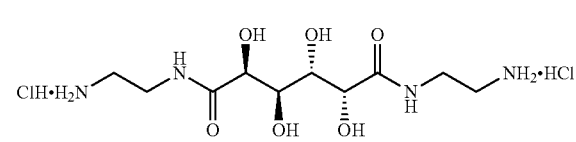

to mucic acid di(aspartyl(O-t-butyl)-Boc) having the structure:

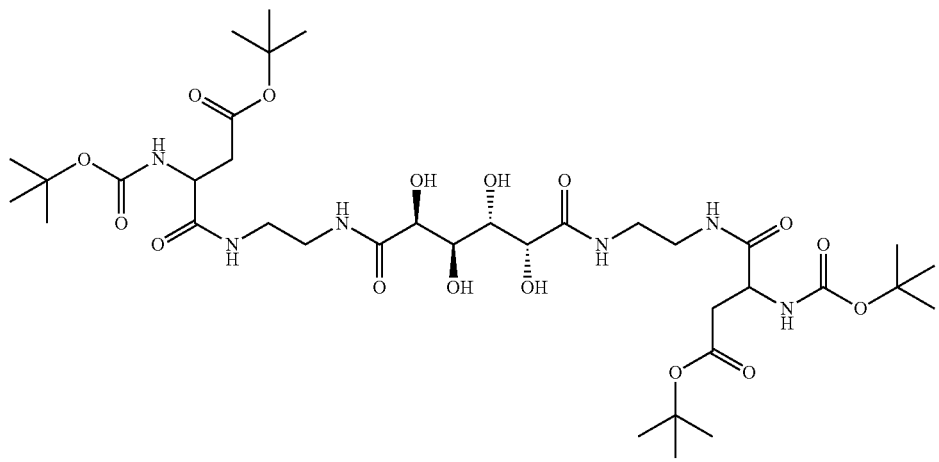

and
(b) converting the mucic acid di(aspartyl(O-t-butyl)-Boc) to mucic acid di(aspartyl amine) di-trifluoroacetate having the structure:

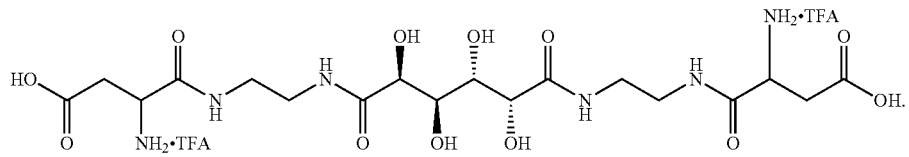

2. The method of embodiment 1, wherein, in step (b):
(a) the mucic acid di(aspartyl(O-t-butyl)-Boc) is converted to the mucic acid di(aspartyl amine) neutral species-having the structure:

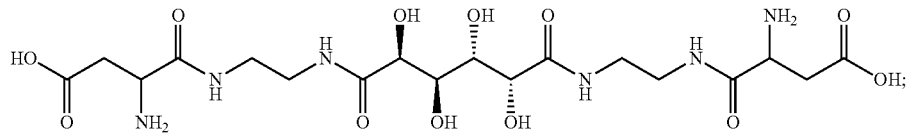

and
(b) the mucic acid di(aspartyl amine) neutral species is converted to the mucic acid di(aspartyl amine) di-trifluoroacetate.

3. A method for synthesizing mucic acid di(aspartyl amine) di-trifluoroacetate, the method comprising converting mucic acid di(aspartyl amine) neutral species having the structure:

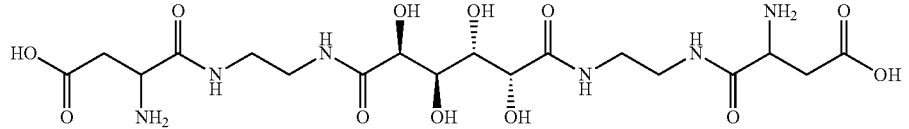

to the mucic acid di(aspartyl amine) di-trifluoroacetate having the structure:

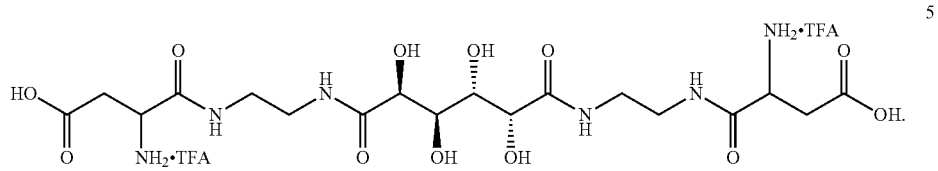

4. A mucic acid di(aspartyl amine) neutral species having the structure:

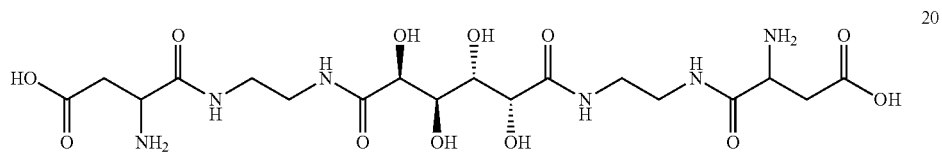 [SMILES: NC(CC(=O)O)C(=O)NCCNC(=O)[C@@H](O)[C@H](O)[C@H](O)[C@@H](O)C(=O)NCCNC(=O)C(N)CC(=O)O]

5. A method for synthesizing a 10-TBDPS derivative of SN38, the method comprising heating a mixture of SN38 and tert-butyl(chloro)diphenylsilane (TBDPSCl) in a base (e.g., an amine base, e.g., a trialkyl amine, e.g., triethylamine) and a solvent (e.g., dichloromethane (DCM)), wherein the product has the structure:

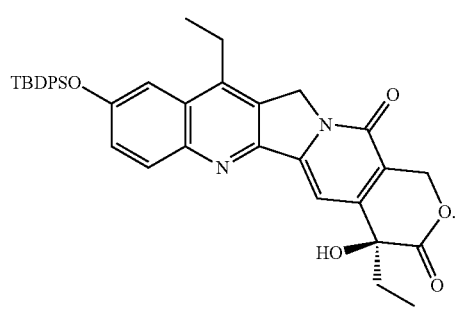

In certain embodiments, the mixture is heated a temperature in a range of from 15° C. to 90° C. for a time in a range of from 5 minutes to 48 hours. In additional embodiments, at the conclusion of the reaction, the reaction mixture is washed sequentially with a dilute acid (e.g., 0.2 N HCl), a weak base (e.g., saturated NaHCO$_3$), and brine. In further embodiments, the neutralized solution is dried (e.g., with MgSO$_4$). In additional embodiments, the dried solution is evaporated under vacuum to give a solid. In further embodiments, the solid is recrystallized; e.g., by dissolving the residue (e.g., in DCM) and precipitating the product (e.g., with hexanes).

In additional embodiments, derivatives or analogues of SN38 or CPT, having a 20-OH group and/or a 10-OH group, are used as starting material instead of SN38.

Combinations of the above embodiments are also contemplated as additional embodiments of the inventions disclosed herein.

6. A method for synthesizing a 20-Boc-aminoacyl, 10-TBDPS derivative of SN38, the method comprising combining 10-TBDPS-SN38 and Boc-amino acid-OH in the presence of a solvent, a base and a coupling agent. In certain embodiments the reactants are combined in a solvent (e.g., DCM), and/or a coupling agent (e.g., 1-(3-dimethylaminopropyl)-3-ethylcarbodiimide hydrochloride (EDC·HCl)) and/or a base (e.g., 4-dimethylaminopyridine (DMAP)). In certain embodiments, the reaction is conducted at a temperature of 0° C. to 20° C. or any integral or decimal value therebetween.

7. The method of embodiment 6, wherein the amino acid is selected from the group consisting of glycine (Gly), valine (Val), gamma-amino butyric acid (GABA) and hexanoic acid (Hex).

8. 20-(Boc-Gly)-10-TBDPS-SN38 having the structure:

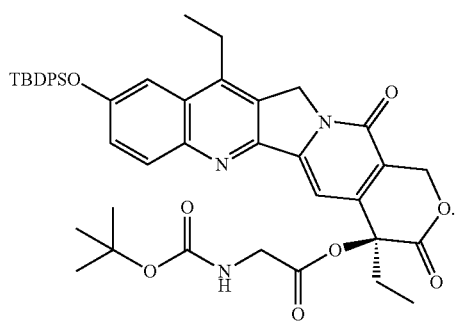

9. 20-(Boc-GABA)-10-TBDPS-SN38 having the structure:

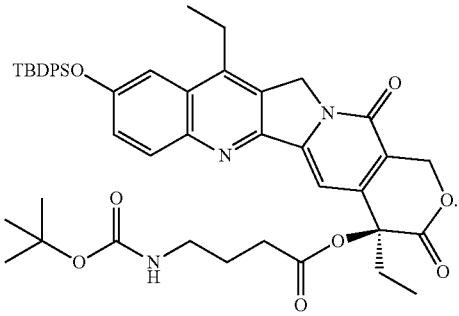

10. 20-(Boc-Hex)-10-TBDPS-SN38 having the structure:

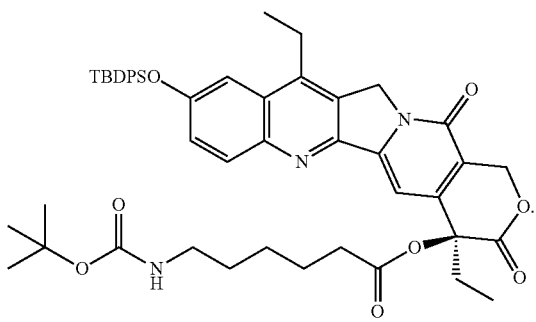

11. 20-(Boc-Val)-10-TBDPS-SN38 having the structure:

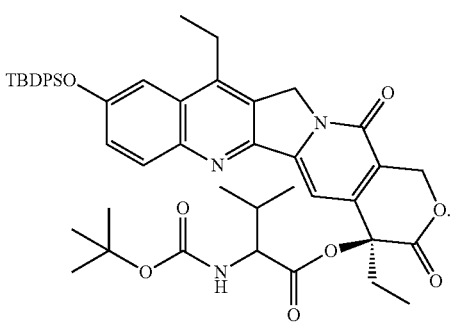

12. A method for synthesizing a 10-OBoc derivative of SN38 (10-OBoc-SN38), the method comprising combining SN38 with di-tert-butyl dicarbonate in the presence of a base (e.g., pyridine) and a solvent (e.g., DCM), wherein the 10-OBoc-SN38 has the structure:

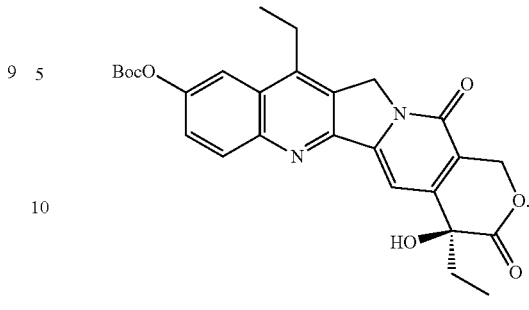

13. A method for synthesizing a 20-(Boc-aminoacyl), 10-OBoc derivative of SN38, the method comprising combining 10-OBoc-SN38 with Boc-amino acid-OH in the presence of a solvent (e.g., DCM), a base (e.g., DMAP) and a coupling agent (e.g., EDC·HCl) at reduced temperature, wherein the 20-(Boc-aminoacyl)-10-OBoc-SN38 has the structure:

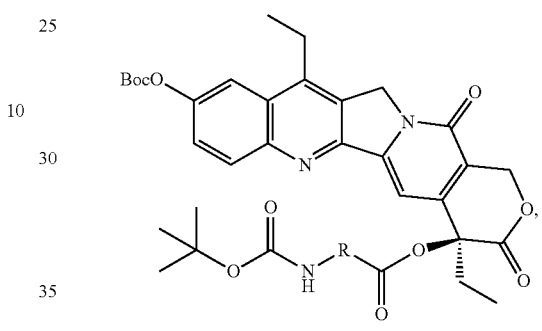

20-(Boc-aminoacyl)-10-OBoc-SN38 wherein R is one or more α-carbon atoms of an amino acid optionally bonded to an amino acid functional group. In certain embodiments, the reaction is conducted at a temperature of 0° C. to 20° C. or any integral or decimal value therebetween.

14. The method of embodiment 12, wherein the amino acid functional group is selected from functional groups of glycine (Gly), alanine (Ala), β-alanine (β-Ala), valine (Val) and leucine (Leu).

15. 20-(Boc-Gly)-10-OBoc-SN38 having the structure:

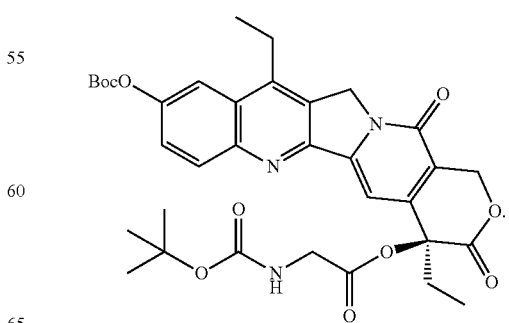

16. 20-(Boc-Ala)-10-OBoc-SN38 having the structure:
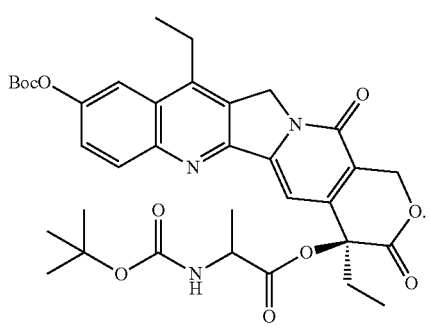
17. 20-(Boc-β-Ala)-10-OBoc-SN38 having the structure:
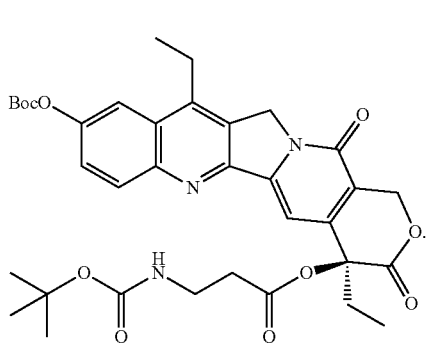
18. 20-(Boc-Val)-10-OBoc-SN38 having the structure:
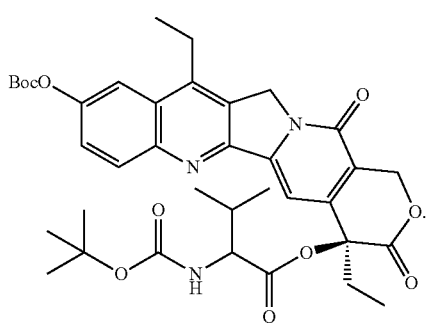
19. 20-(Boc-Leu)-10-OBoc-SN38 having the structure:
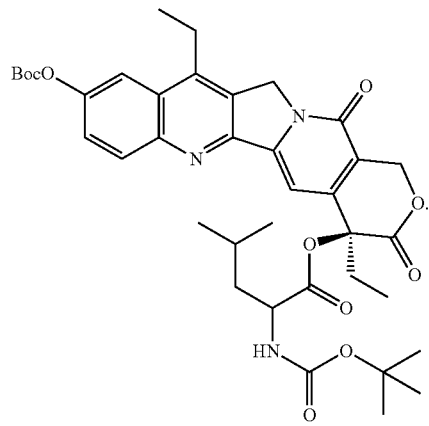
20. 20-(HCl·Gly)-SN38 having the structure:
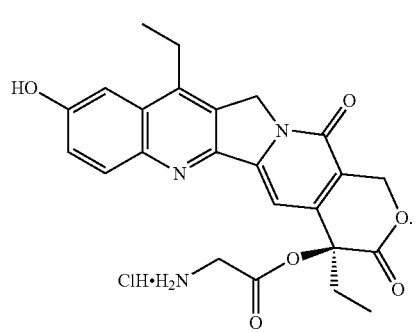
21. 20-(TFA·GABA)-SN38 having the structure:
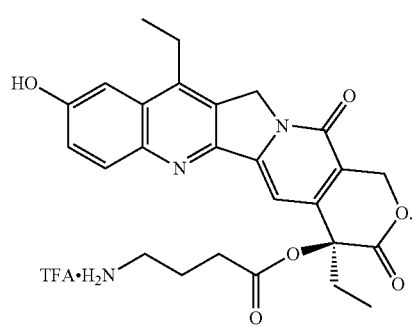

22. 20-(TFA·Hex)-SN38 having the structure:
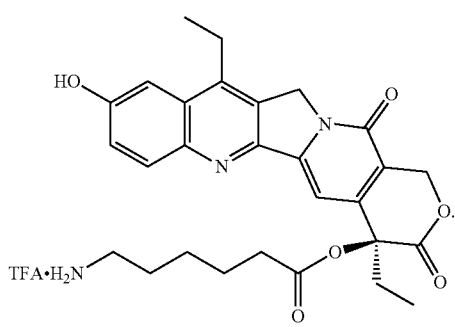
23. 20-(HCl·Val)-SN38 having the structure:
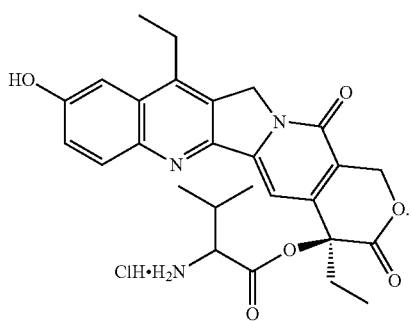
24. 20-(TFA·Gly)-SN38 having the structure:
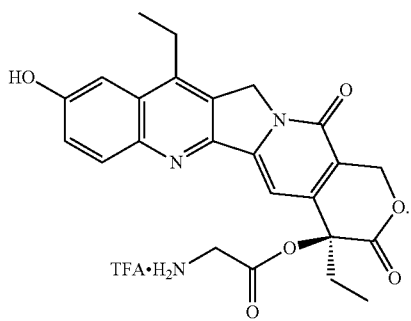
25. 20-(TFA·Ala)-SN38 having the structure:
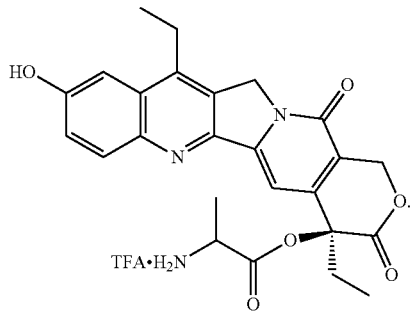
26. 20-(TFA·β-Ala)-SN38 having the structure:
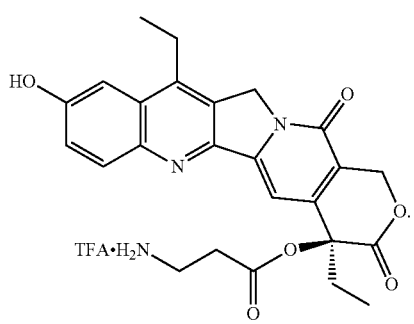
27. 20-(TFA·Val)-SN38 having the structure:
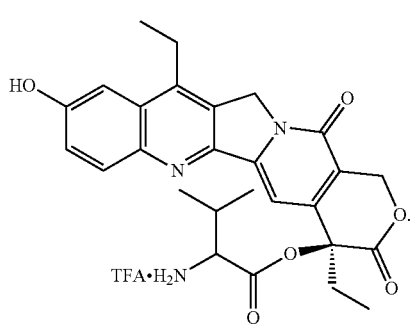

28. 20-(TFA·Leu)-SN38 having the structure:

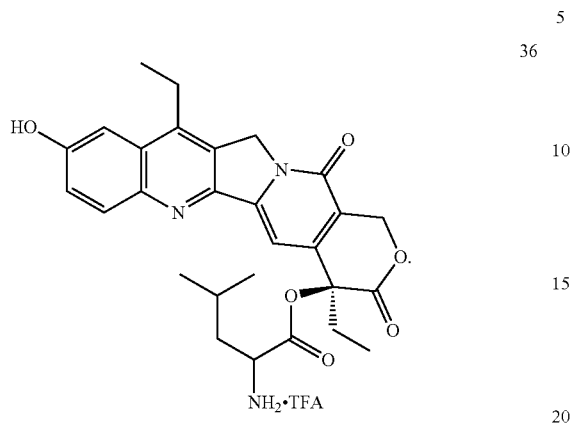

29. A mucic acid polymer-SN38 conjugate (MAP-Gly-SN38) having the structure:

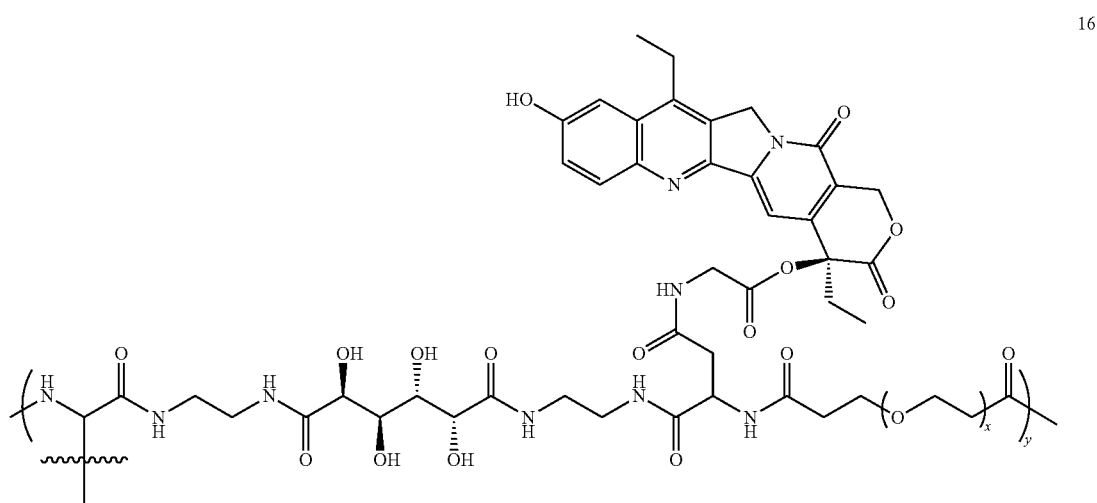

In certain embodiments, x, in Compound 16, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

30. A mucic acid polymer-SN38 conjugate (MAP-GABA-SN38) having the structure:

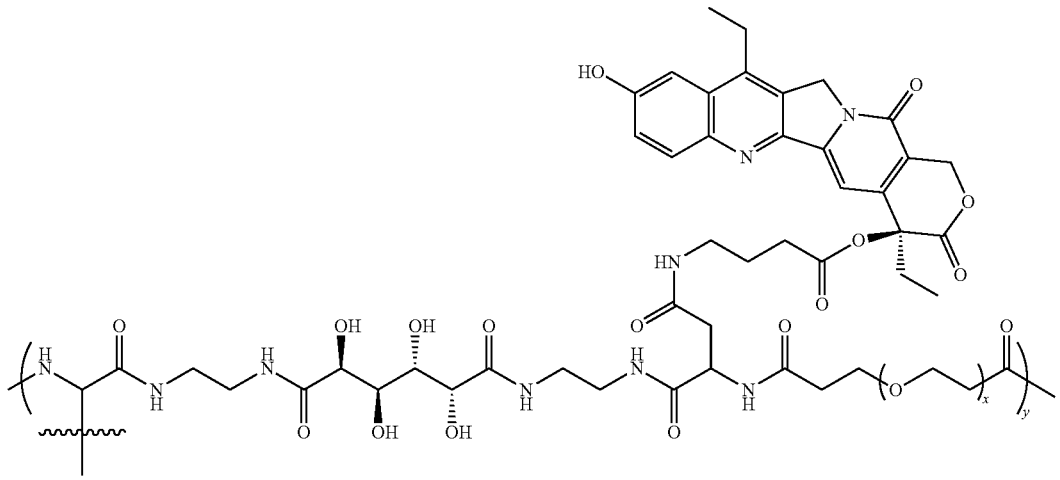

17

In certain embodiments, x, in Compound 17, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—$CH_2$—$CH_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

31. A mucic acid polymer-SN38 conjugate (MAP-Hex-SN38) having the structure:

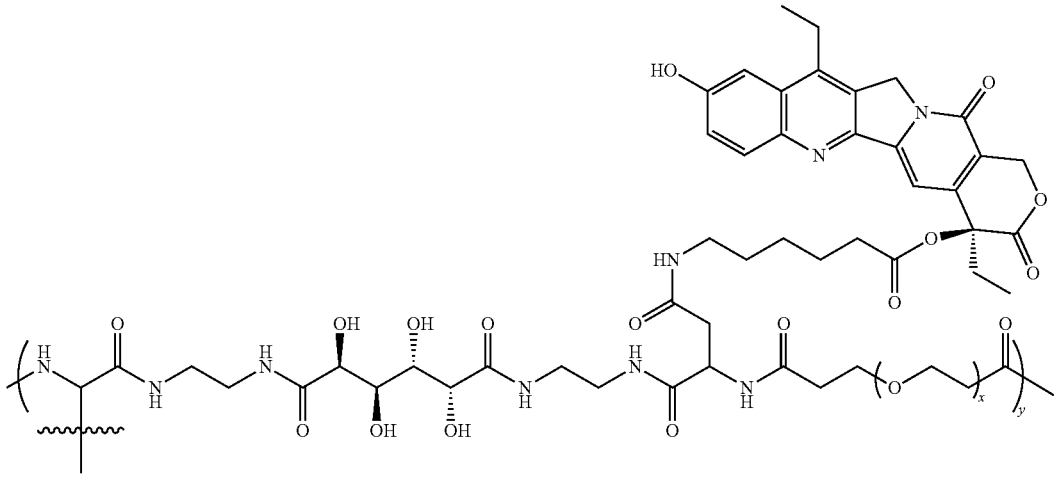

18

In certain embodiments, x, in Compound 18, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

32. A mucic acid polymer-SN38 conjugate (MAP-Val-SN38) having the structure:

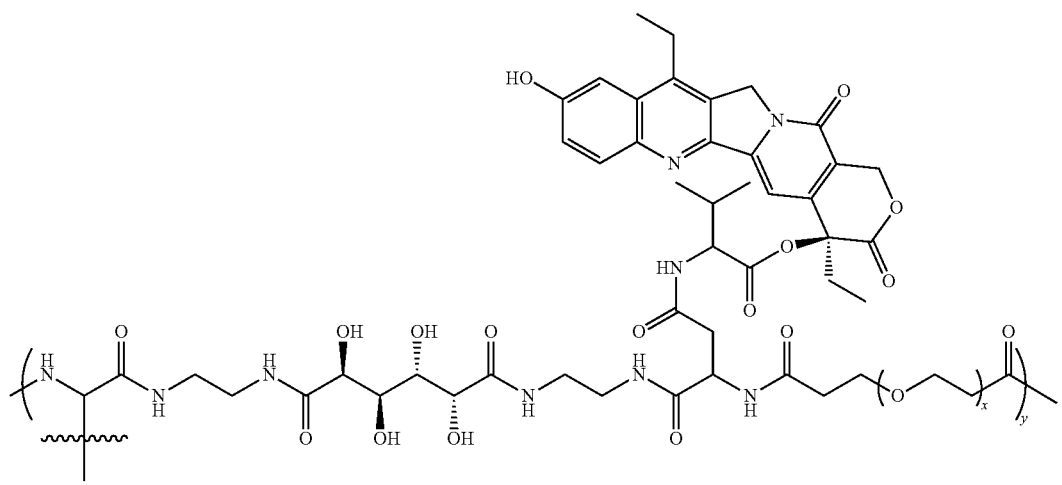

19

In certain embodiments, x, in Compound 19, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

33. A mucic acid polymer-SN38 conjugate (MAP-Ala-SN38) having the structure:

37

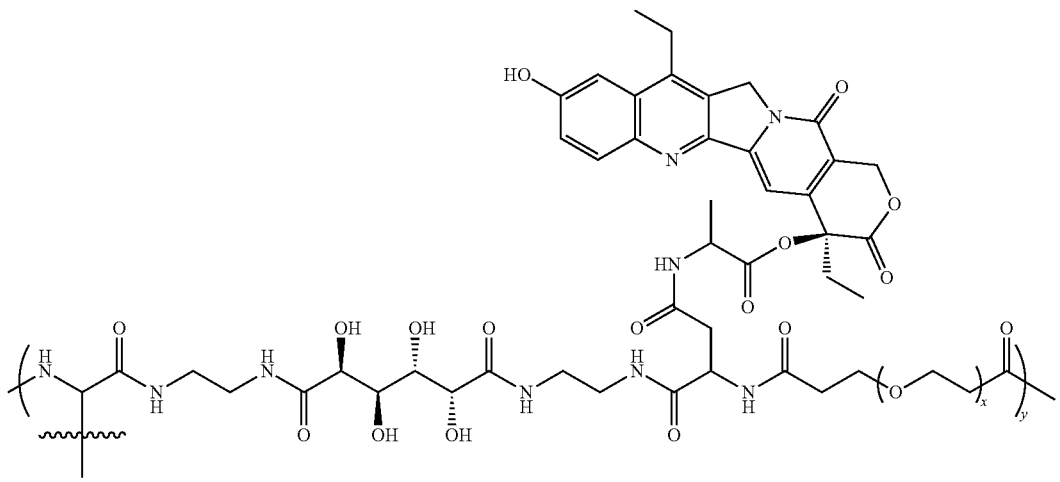

In certain embodiments, x, in Compound 37, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

34. A mucic acid polymer-SN38 conjugate (MAP-β-Ala-SN38) having the structure:

38

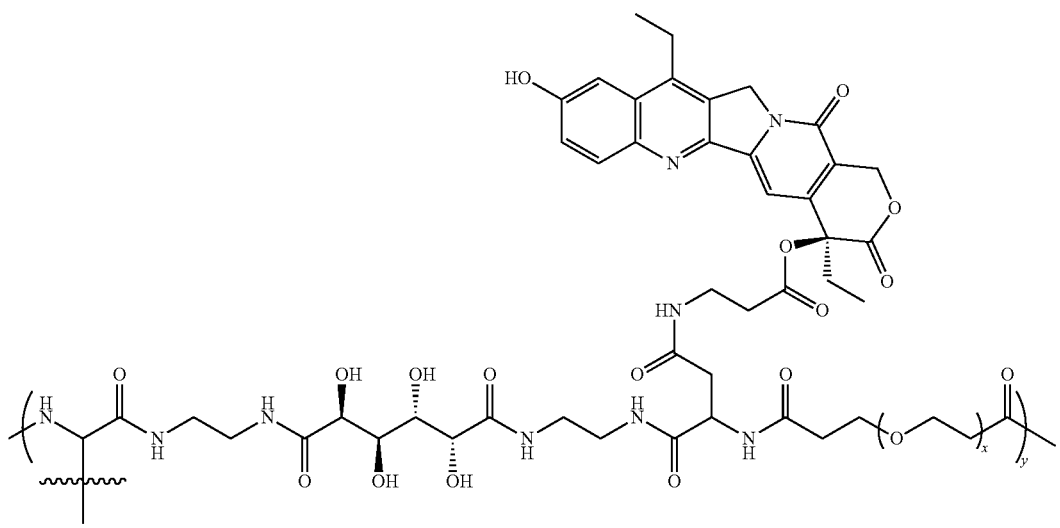

In certain embodiments, x, in Compound 38, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

35. A mucic acid polymer-SN38 conjugate (MAP-Leu-SN38) having the structure:

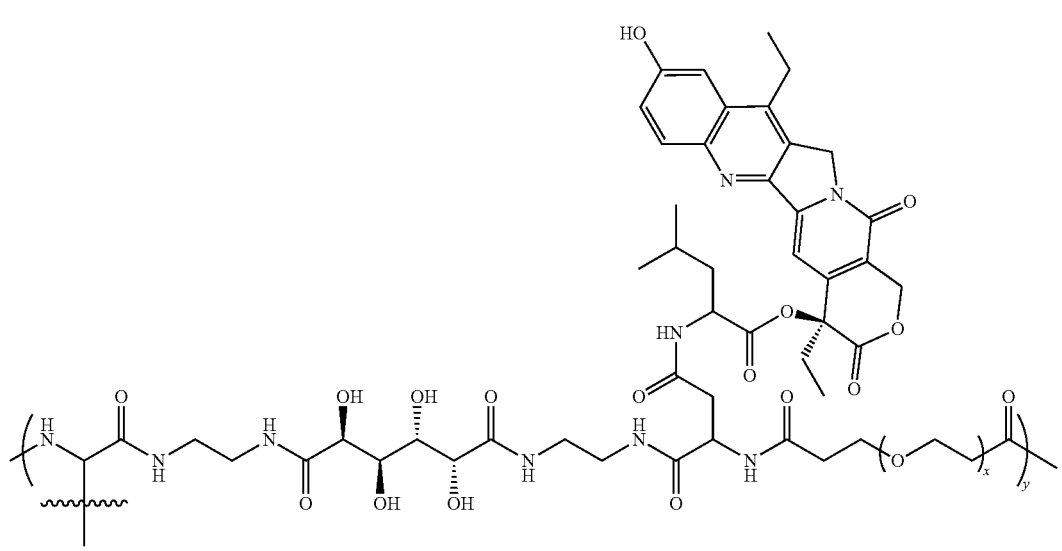

In certain embodiments, x, in Compound 39, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

36. A nanoparticle comprising the MAP-SN38 conjugate of any of embodiment 29-35.

37. 20-(Boc-Gly)-CPT having the structure:

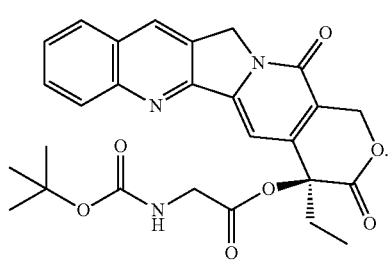

38. 20-(Boc-Val)-CPT having the structure:
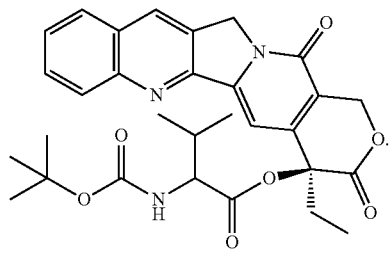
39. 20-(Boc-Ala)-CPT having the structure:
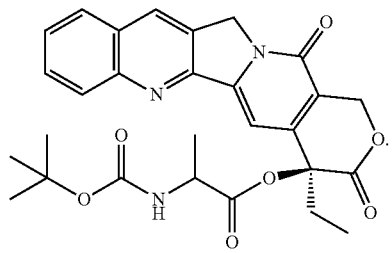
40. 20-(Boc-β-Ala)-CPT having the structure:
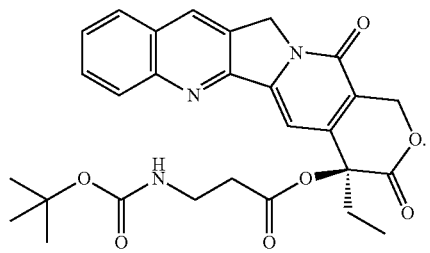
41. 20-(Boc-GABA)-CPT having the structure:
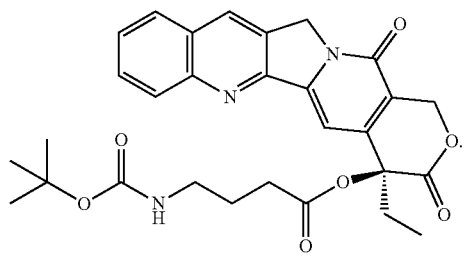
42. 20-(Boc-Phe-Gly)-CPT having the structure:
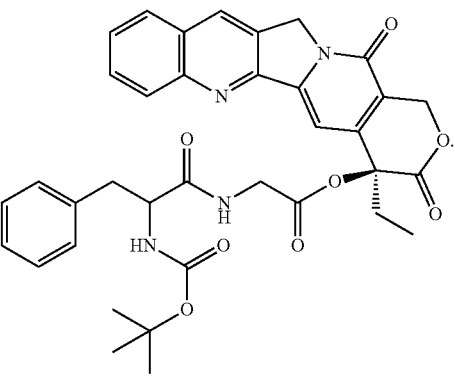
43. 20-(TFA·Gly)-CPT having the structure:
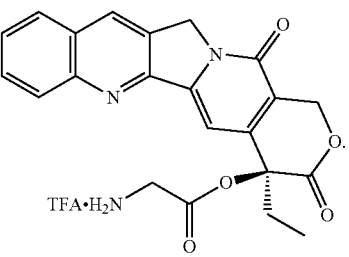
44. 20-(TFA·Ala)-CPT having the structure:
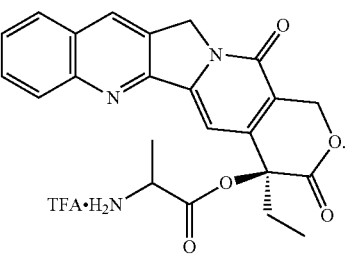
45. 20-(TFA·β-Ala)-CPT having the structure:
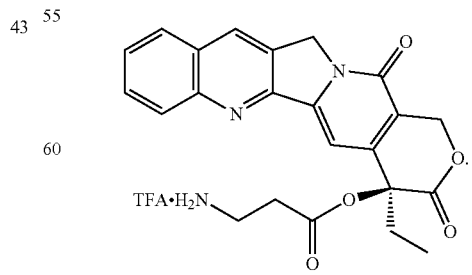

46. 20-(TFA·Val)-CPT having the structure:

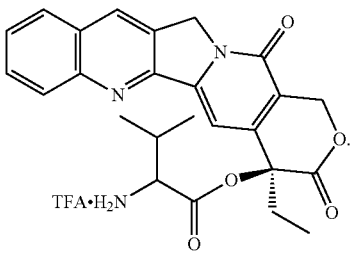

47. 20-(TFA·GABA)-CPT having the structure:

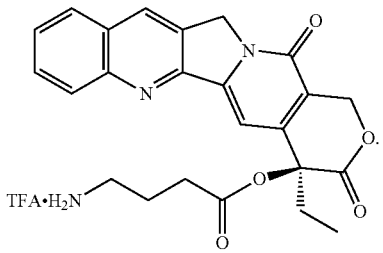

48. 20-(TFA·Phe-Gly)-CPT having the structure:

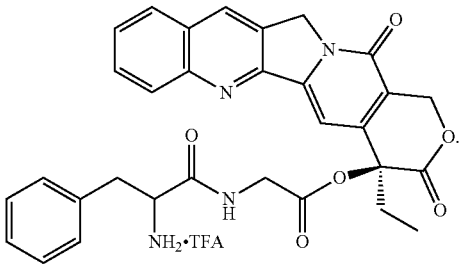

49. A method for synthesizing a nitrophenyl boronic acid-polyethylene glycol conjugate (NPBA-PEG-AA) having the structure:

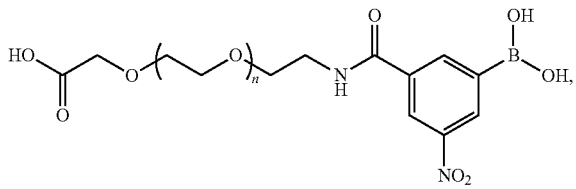

the method comprising:
(a) suspending NH$_2$-PEG-acetic acid (AA) in a base (e.g., N,N'-diisopropylethylamine, DIPEA) and a solvent (e.g., DCM);
(b) dissolving 3-carboxy-5-nitrophenylboronic acid in a solvent mixture (e.g., DCM and dimethyl formamide (DMF));
(c) adding a coupling agent (e.g., N-ethoxycarbonyl-2-ethoxy-1,2-dihydroquinoline, EEDQ) to the solution of (b);
(d) combining the solutions of (a) and (c); and
(e) acidifying the mixture,
wherein n is a number in a range of from 2 to 2,000 or any integral values therebetween; e.g., from 100 to 300, from 20 to 300, from 120 to 180, and/or from 140 to 160.

In certain embodiments, the reaction is conducted at reduced temperature; for example, at a temperature in a range of from 0° C. to 20° C. or any integral or decimal value therebetween, and subsequently warmed to ambient temperature prior to acidification and purification. In certain embodiments the mixture is acidified to a pH of approximately 4. In additional embodiments, the product is purified by extraction with a solvent (e.g., isopropyl acetate, iPrOAc).

In certain embodiments, the value of n is such that the PEG (i.e., —CH$_2$—CH$_2$—O—) portion of the compound has a weight average molecular weight in a range of from about 2 to about 15 kDa; e.g., about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, or about 15 kDa.

50. A compound (NPBA-PEG-AA-PFP) having the structure:

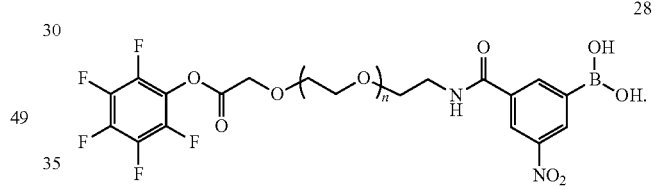

In certain embodiments, n is a number in a range of from 2 to 2,000 or any integral values therebetween; e.g., from 100 to 300, from 20 to 300, from 120 to 180, and/or from 140 to 160.

In certain embodiments, the value of n is such that the PEG (i.e., —CH$_2$—CH$_2$—O—) portion of the compound has a weight average molecular weight in a range of from about 2 to about 15 kDa; e.g., about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, or about 15 kDa.

51. A method for making the compound of embodiment 50, the method comprising: combining the NPBA-PEG-AA of embodiment 49 with bis(pentafluorophenyl) carbonate and a base catalyst (e.g., N-methylmorpholine).

52. A method for synthesizing a NPBA-PEG-transferrin conjugate, the method comprising:
combining the NPBA-PEG-AA-PFP of embodiment 50 with holo-transferrin (i.e., iron-bound transferrin).

53. A method for synthesizing a NPBA-PEG-trastuzumab conjugate, the method comprising:
combining the NPBA-PEG-AA-PFP of embodiment 50 with trastuzumab.

54. A method for synthesizing a NPBA-PEG-therapeutic polypeptide conjugate, the method comprising:
combining the NPBA-PEG-AA-PFP of embodiment 50 with a therapeutic polypeptide.

55. A 20-Boc-aminoacyl, 10-TBDPS derivative of SN38 (20-(Boc-aminoacyl)-10-TBDPS-SN38) having the structure:

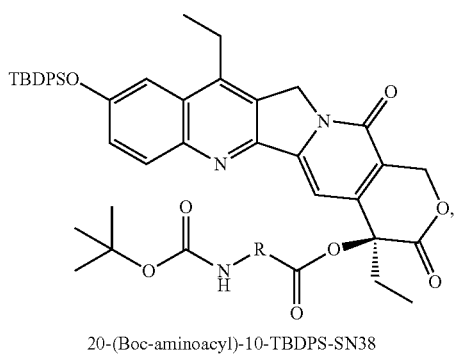

20-(Boc-aminoacyl)-10-TBDPS-SN38 wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

56. The 20-Boc-aminoacyl, 10-TBDPS SN38 derivative of embodiment 55, wherein the amino acid functional group is selected from functional groups of glycine, valine, gamma-amino butyric acid (GABA) and hexanoic acid.

57. A 20-Boc-aminoacyl, 10-OBoc derivative of SN38 (20-(Boc-aminoacyl)-10-OBoc-SN38) having the structure:

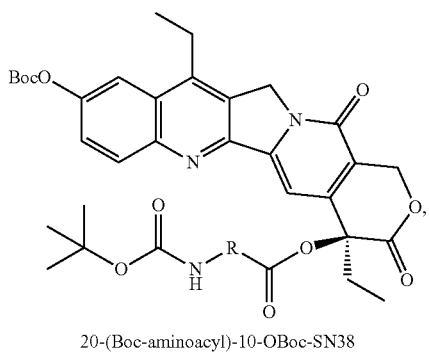

20-(Boc-aminoacyl)-10-OBoc-SN38 wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

58. The 20-Boc-aminoacyl, 10-OBoc SN38 derivative of embodiment 57, wherein the amino acid functional group is selected from functional groups of glycine, alanine, β-alanine, valine and leucine.

59. A HCl salt of a 20-aminoacyl derivative of SN38 (20-(HCl·aminoacyl)-SN38) having the structure:

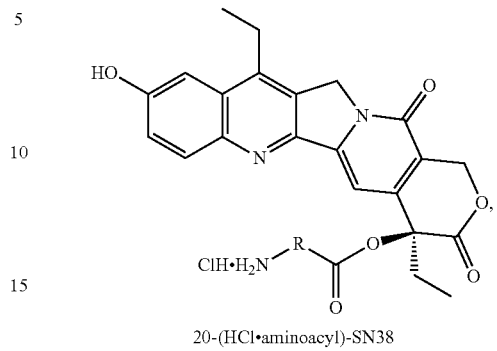

20-(HCl·aminoacyl)-SN38 wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

60. The HCl salt of embodiment 59, wherein the amino acid functional group is selected from functional groups of glycine and valine.

61. A trifluoroacetate (TFA) salt of a 20-aminoacyl derivative of SN38 (20-(TFA·aminoacyl)-SN38) having the structure:

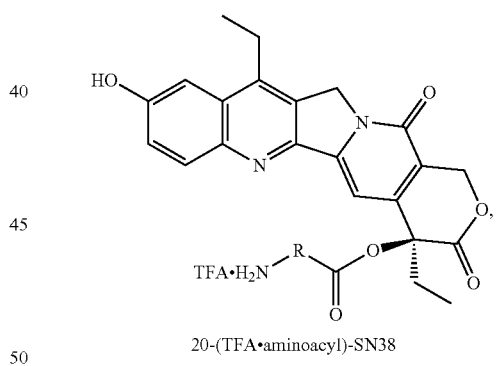

20-(TFA·aminoacyl)-SN38 wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

62. The TFA salt of embodiment 61, wherein the amino acid functional group is selected from functional groups of glycine, alanine, β-alanine, valine, GABA, hexanoic acid and leucine.

63. A mucic acid polymer (MAP)-amino acid-SN38 conjugate having the structure:

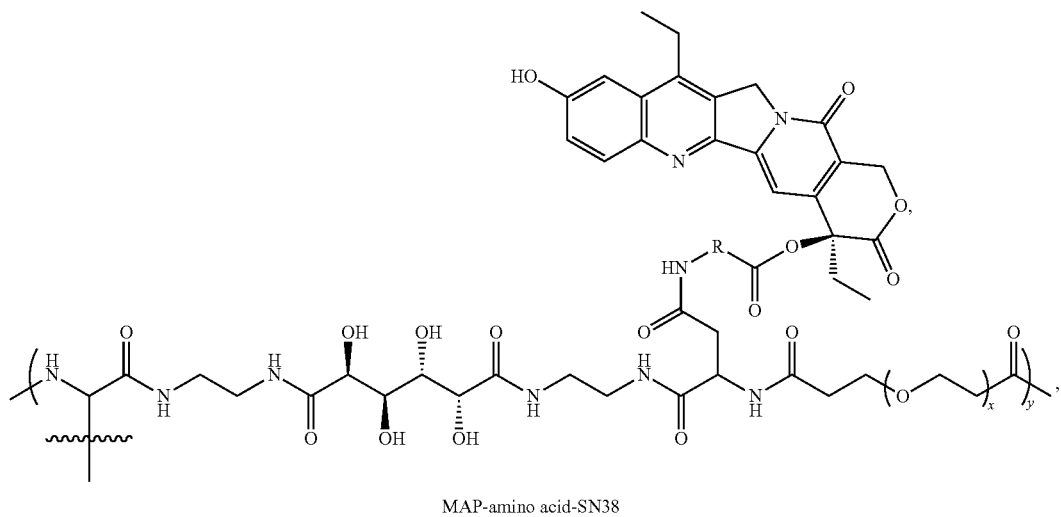

MAP-amino acid-SN38 wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

In certain embodiments, x, in a MAP-amino acid-SN38 conjugate, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

64. The MAP-amino acid-SN38 conjugate of embodiment 63, wherein the amino acid functional group is selected from functional groups of glycine, alanine, β-alanine, valine, GABA, hexanoic acid and leucine.

65. A nanoparticle comprising the MAP-amino acid-SN38 conjugate of either of embodiments 63 or 64.

66. A 20-Boc-aminoacyl derivative of camptothecin (20-(Boc-aminoacyl)-CPT) having the structure:

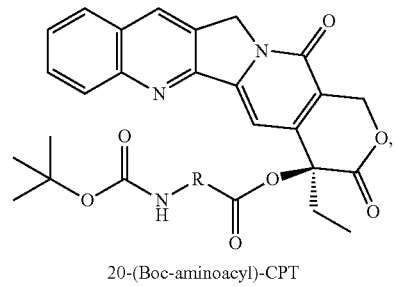

20-(Boc-aminoacyl)-CPT wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

67. The 20-(Boc-aminoacyl) CPT derivative of embodiment 66, wherein the amino acid functional group is selected from functional groups of glycine, valine, alanine, β-alanine, GABA and the dipeptide phenylalanine-glycine.

68. A trifluoroacetate (TFA) salt of a 20-aminoacyl derivative of CPT (20-(TFA·aminoacyl)-CPT) having the structure:

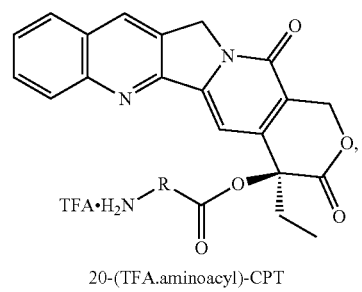

20-(TFA·aminoacyl)-CPT wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide.

69. The TFA salt of embodiment 68, wherein the amino acid functional group is selected from functional groups of glycine, alanine, β-alanine, valine, GABA and the dipeptide phenylalanine-glycine.

70. A mucic acid polymer (MAP)-amino acid-CPT conjugate having the structure:

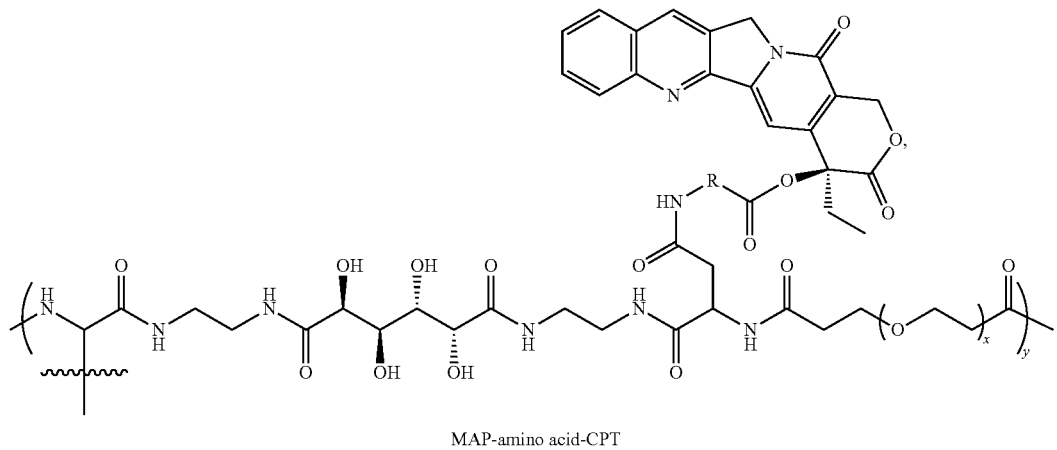

MAP-amino acid-CPT wherein R is one or more α-carbon atoms of an amino acid optionally bonded to an amino acid functional group. The term "R is one or more α-carbon atoms of an amino acid" reflects the fact that —NH—R—CO$_2$— in the structure above (i.e., the linker between the SN38 portion and the MAP/PEG portion of the structure) represents an amino acid. "One or more" reflects the fact that the linker can comprise more than one amino acid; i.e., the linker can be a dipeptide, tripeptide or oligopeptide. In certain embodiments, the amino acid functional group is selected from functional groups of alanine, β-alanine, valine, GABA and the dipeptide phenylalanine-glycine.

In certain embodiments, x, in a MAP-amino acid-CPT conjugate, is a number in a range of from 20 to 200, and y is a number in a range of from 5 to 200 (or any integral values therebetween; e.g., from 10 to 150, from 20 to 120, from 50 to 100, or from 10 and 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

71. A nanoparticle comprising the MAP-amino acid-CPT conjugate of embodiment 70.

DETAILED DESCRIPTION

The present disclosure may be understood more readily by reference to the following description taken in connection with the accompanying Examples, all of which form a part of this disclosure. It is to be understood that this disclosure is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the disclosure herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (and the systems used in such methods and the compositions derived therefrom) to prepare and use the inventive materials, and the materials themselves, where the methods and materials are capable of delivering the highlighted properties using only the elements provided in the claims. That is, while other materials may also be present in the inventive compositions, the presence of these extra materials is not necessary to provide the described benefits of those compositions (i.e., the effects may be additive) and/or these additional materials do not compromise the performance of the product compositions. Similarly, where additional steps may also be employed in the methods, their presence is not necessary to achieve the described effects or benefits and/or they do not compromise the stated effect or benefit.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Likewise, a term such as $C_{1-3}$ alkyl also includes, as separate embodiments, $C_1$ alkyl, $C_2$ alkyl, $C_3$ alkyl, $C_{1-2}$ alkyl, and $C_{2-3}$ alkyl.

Throughout this specification, words are to be afforded their normal meaning, as would be understood by those skilled in the relevant art. However, so as to avoid misunderstanding, the meanings of certain terms will be specifically defined or clarified.

Reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

Abbreviations

AA: acetic acid
ACN: acetonitrile
Ala: alanine, alanyl
ARS: alizarin red S
Asp: aspartate, aspartic acid
β-Ala: beta-alanine, beta-alanyl
BBB: blood-brain barrier
Boc: tert-butoxy carbonyl
BTB: blood-tumor barrier
CPME: cyclopentyl methyl ether
CPT: camptothecin
CV: column volume
DCM: dichloromethane
DIC: N,N'-diisopropylcarbodiimide
DIPEA: N,N'-diisopropylethyamine
diSPA-PEG: di(succinimidyl propionate)-PEG
DMA: dimethylacetamide
DMAP: 4-dimethylaminopyridine
DMF: dimethyl formamide
DMSO: dimethyl sulfoxide EDC·HCl: 1-(3-dimethylaminopropyl)-3-ethylcarbodiimide hydrochloride
EEDQ: N-ethoxycarbonyl-2-ethoxy-1,2-dihydroquinoline
EtOAc: ethyl acetate
GABA: gamma-amino butyric acid, gamma-amino butyryl
Gly: glycine, glycyl
GPC: gel permeation chromatography
HBSS: Hank's balanced salt solution
HCl: hydrochloric acid
Hex: 6-aminohexanoic acid
HIC: hydrophobic interaction chromatography
HOPO: hydroxypyridine N-oxide
IPA: isopropyl alcohol
iPrOAc: isopropyl acetate
MAM: polymerizable mucic acid monomer
MAP: mucic acid polymer
MeOH: methanol
MTBE: methyl tert-butyl ether
NHS: N-hydroxysuccinimide
NP (or P): nanoparticle
NPBA: 3-carboxy-5-nitrophenylboronic acid
Mono-NPBA-PEG-Tf: mono-PEGylated fraction of transferrin
Mono-NPBA-PEG-Tras: mono-PEGylated fraction of Trastuzumab
PEO: polyethylene oxide
PBS: phosphate-buffered saline
PEG: polyethylene glycol
PES: polyethersulfone
PFP: pentafluorophenyl
PyAOP: (7-azabenzotriazol-1-yloxy)trispyrrolidinophosphonium hexafluorophosphate
SN38: 7-ethyl-10-hydroxy-camptothecin
SpP: strands per particle
TBDPS: tert-butyldiphenylsilane; tert-butyldiphenylsilyl
TBDPSCl: tert-butlyl(chloro)diphenylsilane
TEA: triethylamine
Tf: holo-transferrin
TFA: trifluoroacetate, trifluoroacetic acid
THF: tetrahydrofuran
Tras: trastuzumab
UF/DF: ultrafiltration and diafiltration
Val: valine, valyl
Reaction Components The procedures described herein include standard solvents and catalysts as are known in the art. Although particular compounds (e.g., acids, bases, coupling agents) are recited in the disclosure, it is clear to one of skill in the art that different reagents can be used.

To that end, exemplary solvents include but are not limited to chlorinated solvents (e.g., dichloromethane, chloroform, 1,2-dichloroethane), ethers (e.g., diethyl ether, tert-butyl methyl ether, cyclopentyl methyl ether, diglyme, 1,4-dioxane, 2-methyltetrahydrofuran), alcohols (e.g., methanol, ethanol, isopropanol, tert-butanol), alkanes (e.g., pentane, hexanes, heptanes), glycols (e.g., ethylene glycol, polyethylene glycol), polar aprotic solvents (e.g., dimethylacetamide, acetonitrile, dimethyl sulfoxide, dimethyl formamide, acetone, N-methyl-2-pyrrolidone), and polar protic solvents (e.g., water, ethanol, acetic acid, propionic acid).

Exemplary acids include but are not limited to mineral acids (e.g., hydrochloric acid, nitric acid, phosphoric acid, sulfuric acid) and organic acids (e.g., acetic acid, malonic acid, methanesulfonic acid, propionic acid, thioacetic acid, p-toluenesulfonic acid, tribromoacetic acid, trichloroacetic acid, trifluoroacetic acid).

Exemplary bases include but are not limited to amino bases (e.g. 1,4-diazabicyclo[2.2.2]octane, diethylamine, triethylamine, N,N-diisopropylethylamine, lithium amide, lithium bis(trimethylsilyl)amide, morpholine, piperidine), alkoxides (e.g., barium tert-butoxide, lithium tert-butoxide, sodium methoxide), hydroxides (e.g., tetrabutylammonium hydroxide, sodium hydroxide, potassium hydroxide), organometallic bases (e.g., n-butyllithium, tert-butyllithium, butyl magnesium chloride), pyridines (e.g., 4-dimethylaminopyridine, 2,6-lutidine, pyridine), carbonates (e.g., lithium carbonate, sodium carbonate, magnesium carbonate, potassium carbonate), and hydrides (e.g., sodium hydride, calcium hydride, potassium hydride).

Exemplary coupling agents include but are not limited to carbodiimide reagents (e.g., N,N'-diisopropylcarbodiimide, 1-(3-dimethylaminopropyl)-3-ethylcarbodiimide hydrochloride, N,N'-dicyclopentylcarbodiimide), additives for carbodiimide reagents (e.g., 1-hydroxy-7-azabenzotriazole, 6-chloro-1-hydroxy benzotriazole, N-hydroxysuccinimide, 1-hydroxy-2-pyridinone, 6-chloro-N-hydroxy-2-phenylbenzimidazole, ethyl 2-cyano-2-(hydroxyimino)acetate), anhydride based or forming reagents (e.g., ditertbutyl carbonate, acetic anhydride, 2-ethoxy-1-ethoxycarbonyl-1,2-dihydroquinoline, ethylchloroformate), acylazoles (e.g., carbonyl diimidazole), acid halide generating reagents (e.g., thionyl chloride, phosgene, cyanuric chloride, benzyltriphenylphosphonium dihydrogen trifluoride), phosphonium salt coupling reagents (e.g., benzotriazol-1-yloxytris(diemthylamino)phosphonium hexafluorophosphate), tetramethyl aminium reagents (e.g., 2-(2-oxo-1(2H)-pyridyl-1,1,3,3-tetramethyluronium tetrafluoroborate), aminium reagents (e.g., 2-chloro-1,3-dimethylimidazolidinium hexafluorophosphate), oxyma uranium salts (e.g., 1-((1-cyano-2-ethoxy-2-oxoethylideneaminooxy)(morpholino)methylene) pyrrolidinium hexafluorophosphate), antimonate uranium salts (e.g., benzotriazol-1-yloxuy-N,N-dimethyl-methaniminium hexachloroantimonate), organophosphorus reagents (e.g., diethylcyanophosphonate, 1-oxo-chlorophospholane, 2-propanephosphonic acid anhydride), triazine based reagents (e.g., 2-chloro-4,6-dimethoxy-1,3,5-triazine), organosulfur reagents (e.g., pentafluorophenyl-4-nitrobenzenesulfonate), pyridinium reagents (e.g., 2-chloro-1-methylpyridinium iodide), polymer bound reagents (e.g., polymer supported N-ethoxycarbonyl-2-ethoxy-1,2-dihydroquinoline).

Synthesis of Polymerizable Mucic Acid Monomer (MAM)

Provided herein are, inter alia, methods for synthesis of a polymerizable derivative of mucic acid (a "mucic acid monomer" or MAM). In the first stage, mucic acid is reacted with methanol (MeOH) in the presence of sulfuric acid to form a 1,6-dimethyl diester of mucic acid (Compound 1). The diester is then reacted with N-Boc-ethylenediamine in the presence of triethylamine (TEA) and MeOH to form a N-Boc-protected mucic acid ethylenediamine (Compound 2).

In an alternative method for preparative-scale manufacture of N-Boc-protected mucic acid ethylenediamine, mucic acid is reacted with MeOH in the presence of sulfuric acid to generate a methoxylated mucic acid derivative followed by reaction of the methoxylated mucic acid with N-(2- aminoethyl)(tert-butoxy)carboxamide, in TEA and MeOH, to generate the N-Boc-protected mucic acid diamine. See Example 24.

Previous methods have conducted this first stage (i.e., conversion of mucic acid to N-Boc-protected mucic acid ethylene diamine) in two separate reactions; first forming the diester, purifying the diester, and then converting the isolated diester to the N-Boc-protected mucic acid ethylenediamine. See, for example, U.S. Pat. No. 10,166,291; and U.S. Patent Application Publication No. 2019/0381188 (Dec. 19, 2019). In the methods described herein, the conversion of mucic acid to N-Boc-protected mucic acid ethylenediamine is accomplished in a single reaction. See Example 1.

Any and all combinations of two or more of the preceding embodiments are also contemplated as additional embodiments of the inventions disclosed herein.

In the next stage, the Boc protecting group is removed from N-Boc-protected mucic acid ethylenediamine by reacting with MeOH and HCl. This converts the N-Boc-protected mucic acid ethylenediamine to mucic acid ethylenediamine chloride (Compound 3). See Example 2. An alternative preparative-scale method for preparing mucic acid ethylenediamine chloride (mucic acid diaminochloride) by reaction with MeOH and HCl is provided in Example 25.

In the next stage, mucic acid ethylenediamine chloride is converted to mucic acid di(aspartyl(O-t-butyl)-Boc) (Compound 4) by reaction of the mucic acid diaminochloride with Boc-L-aspartic acid 4-tert-butyl ester in the presence of hydroxypyridine N-oxide (HOPO), N,N'-diisopropylcarbodiimide (DIC) and acetonitrile (ACN). See Example 3. Reaction time can be a in a range of from 5 minutes to 48 hours at a temperature in a range of from 15° C. to 90° C. In previous methods, mucic acid ethylenediamine was reacted with di(aspartyl(O-benzyl)-Boc) in the presence of ACN and pyridine, resulting in the addition of a di(aspartyl (O-benzyl)-Boc) protecting group (see, for example, U.S. Patent Application Publication No. 2019/0381188 (Dec. 19, 2019)), rather than the di(aspartyl(O-t-butyl)-Boc) protecting group used in the methods disclosed herein. Thus, the methods described herein utilize new reagents (HOPO and DIC instead of pyridine) and a different protecting group (O-t-butyl instead of O-benzyl). The advantage of the t-butyl protecting group used in the present methods, compared to the benzyl group used in previous methods, is that the t-butyl protecting group can be removed with HCl or trifluoroacetic acid (TFA). Accordingly, in the next stage of the synthesis, both protecting groups (t-butyl and Boc) can be removed with a single reagent (e.g., TFA or HCl).

An alternative method for synthesizing mucic acid di(aspartyl(O-t-butyl)-Boc) on a preparative scale is to react Boc-L-aspartic acid 4-tert-butyl ester with ethyl cyanohydroxyiminoacetate (Oxyma) in dichloromethane (DCM), driven by the addition of 1-(3-dimethylaminopropyl)-3-ethylcarbodiimide hydrochloride (EDC·HCl). This mixture is then combined with mucic acid diaminochloride (Compound 3) in an aqueous solution of sodium carbonate. Crude product is concentrated and crystallized by addition of ACN while distilling off the aqueous phase. See Example 26.

Any and all combinations of two or more of the preceding embodiments are also contemplated as additional embodiments of the inventions disclosed herein.

In the final stage of the synthesis of the mucic acid polymerizable monomer, mucic acid di(aspartyl(O-t-butyl)-Boc) is converted to mucic acid di(aspartyl amine) (Compound 5) by reaction of mucic acid di(aspartyl(O-t-butyl)-Boc) with TFA in the presence of DCM. See Example 4. Reaction time can be in a range of from 5 minutes to 96 hours at a temperature in a range of from 15° C. to 90° C. Previous methods (see, e.g., U.S. Patent Application Publication No. 2019/0381188 (Dec. 19, 2019)) required two steps for this conversion; first converting mucic acid di(Asp (O-benzyl)-Boc) to mucic acid di(Asp(O-benzyl)-amine); and then converting the mucic acid di(Asp(O-benzyl)-amine) to mucic acid di(Asp-amine). The use of t-butyl and Boc protecting groups in the methods described herein; instead of O-benzyl and Boc protecting groups as described previously, allows removal of the two protecting groups in a single step in aqueous or organic solution; and avoids the need for homogeneous or heterogeneous hydrogenation.

For preparative-scale applications, mucic acid di(aspartyl (O-t-butyl)-Boc) is converted to a mucic acid di(aspartyl amine) neutral species (Compound 20), which is in turn converted to the di-TFA salt of mucic acid di(aspartyl amine) (Compound 5). In these embodiments, mucic acid di(aspartyl(O-t-butyl)-Boc) is reacted with TFA and triisopropylsilane in DCM and water, and can optionally be further recrystallized using tetrahydrofurn (TIF) to form the mucic acid monomer neutral species (20). See Example 27. The neutral mucic acid monomer is then reacted with TFA in DCM and water, and then combined with a solution of seed crystals of Compound 5 in ether to precipitate the MAM-diTFA salt (5). See Example 28.

Any and all combinations of two or more of the preceding embodiments are also contemplated as additional embodiments of the inventions disclosed herein.

Synthesis of Mucic Acid Polymer (MAP)

Provided herein are, inter alia, methods for synthesis of a polymer of mucic acid (a "mucic acid polymer" or MAP). In certain embodiments, diTFA-mucic acid di(aspartyl amine) (MAM, Compound 5) is combined with di(succinimidyl propionate)-PEG (diSPA-PEG) (e.g., diSPA-PEG$_{3.5k}$) in a solvent (e.g., dimethyl sulfoxide, DMSO), a base (e.g., N,N'-diisopropylethylamine, DIPEA) is added, and the reaction is conducted at a temperature range of 15° C. to 70° C. (e.g., 35° C.) for a time in a range of from one hour to 96 hours (e.g., 66 hours). After the desired polymer length is obtained (generally in the range of from 10 kDa to 120 kDa), the reaction mixture is dialyzed against DMSO, dialyzed against water, and filtered to yield MAP (Compound 6).

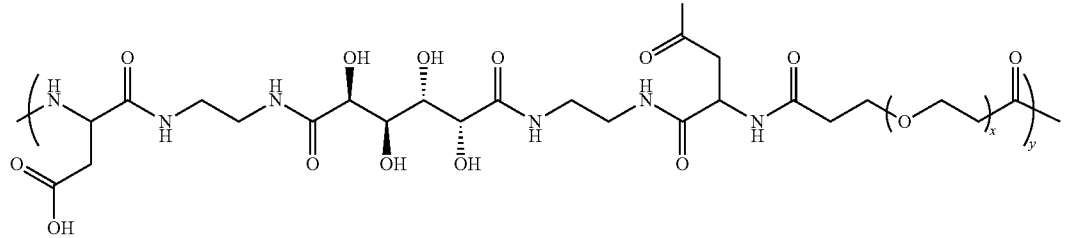

6

The molecular weight of the polymer is controlled by adjusting the molar ratio of MAM to diSPA-PEG; with the highest molecular weight obtained at a 1:1 molar ratio of reactants. The molecular weight of the polymer obtained becomes lower as the molar ratio of MAM to diSPA-PEG become greater than, or less than, 1. In our Examples, further decrease in molecular weight correlates with increase in the MAM to diSPA-PEG ratio. See Example 29.

In certain embodiments, x, in Compound 6, is a number in a range of from 20 to 200, and y is a number in a range of from 5 to 200 (or any integral values therebetween; e.g., from 10 to 150, from 20 to 120, from 50 to 100, or from 10 to 25. In certain embodiments, x is chosen so as to provide a number average molecular weight for the PEG portion of the polymer (i.e., —O—CH$_2$—CH$_2$—) in a range from about 500 Da to about 50,000 Da.

In certain embodiments, the weight average molecular weight of the MAP is in a range of from 5 to 150 kDa or any integral values therebetween, e.g., from 20 to 120 kDa, and the values of x and y are chosen accordingly.

In additional embodiments, values of x and y are chosen such that, after assembly of the MAP, or the drug-conjugated MAP, into a nanoparticle, the size of the nanoparticle is in a range of from 10 to 900 nm or any integral values therebetween, e.g., from 100 to 800 nm, from 200 to 500 nm, from 400 to 700 nm, or from 20 to 100 nm.

In some embodiment the methods described herein are carried out using a targeted nanoparticle that includes a nanoparticle core, as described herein, that is conjugated to any one of the targeting agents, described herein, and any one of the chemotherapeutic agents as described herein, where the total size of the targeted nanoparticle is from about 20 nm to about 100 nm. In some embodiments the size of the targeted nanoparticle is from about 40 nm to about 100 nm. In some embodiments the size of the targeted nanoparticle is from about 40 nm to about 90 nm. In some embodiments the size of the targeted nanoparticle is from about 40 nm to about 80 nm. In some embodiments the size of the targeted nanoparticle is from about 40 nm to about 70 nm. In some embodiments the size of the targeted nanoparticle is from about 40 nm to about 60 nm. In some embodiments the size of the targeted nanoparticle is from about 40 nm to about 50 nm. In some embodiments the size of the targeted nanoparticle is from about 50 nm to about 100 nm. In some embodiments the size of the targeted nanoparticle is from about 50 nm to about 90 nm. In some embodiments the size of the targeted nanoparticle is from about 60 nm to about 80 nm. In some embodiments the size of the targeted nanoparticle is from about 50 nm to about 70 nm. In some embodiments the size of the targeted nanoparticle is from about 70 nm to about 100 nm.

In certain embodiments, the solvent is, for example, dimethyl sulfoxide (DMSO), dimethyl formamide (DMF) or dimethylacetamide (DMA).

In certain embodiments, the elevated temperature is any temperature in a range of from 20° C. to 40° C.; i.e., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

Dialysis can be conducted with membranes of various porosities, for example, membranes having a molecular weight cut-off of 1 kDa, 3 kDa, 5 kDa, 10 kDa, 30 kDa or 50 kDa can be used.

Any and all combinations of two or more of the preceding embodiments are also contemplated as additional embodiments of the inventions disclosed herein.

Determination of Polymer Molecular Weight

Molecular weight determinations of MAPs are conducted by gel filtration chromatography (e.g., a Malvern OMNISEC gel permeation chromatography (GPC) system) using polyethylene oxide (PEO) standards. The chromatography apparatus can comprise, for example, a solvent delivery pump, degasser, autosampling injector, column compartment, refractive index detector, and light scattering detector.

Samples are prepared, for example, by dissolving the MAP in phosphate-buffered saline (PBS) containing 0.02% sodium azide at a concentration in a range of from 1 to 5 mg/mL, then filtering the sample, e.g., through a 0.45 micron (0.45 μm pore size) filter. 100 μL of filtered sample, along with PEO molecular weight standards, is injected onto a gel filtration or gel permeation column, (e.g., a 2×Agilent PL Aquagel-OH 40 column; 300 mm long×7.5 mm diameter; 8 μm particle size) with a mobile phase of PBS+0.02% sodium azide at a flow rate of, e.g., 0.7 mL/minute at a column temperature of, e.g., 30° C. Peak fractions are detected by differential refractive index and/or light scattering and analyzed using, e.g., Malvern OMNISEC software.

Camptothecin (CPT) and its Derivatives, Metabolites and Analogues

The present disclosure provides, inter alia, methods and compositions for preparing selectively reactive derivatives of CPT and its derivatives, metabolites, and analogues. In general, these molecules comprise five fused aromatic rings, one or more of which rings are heteroaromatic, and containing one or more pendant hydroxyl groups, as shown in the diagram below showing the structure of CPT.

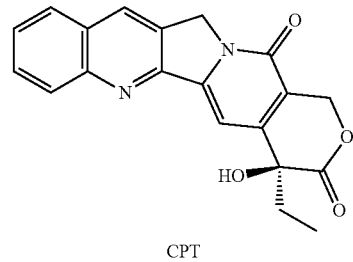 [SMILES: CC[C@@]1(O)C(=O)OCc2c1cc1n(c2=O)Cc2cc3ccccc3nc2-1 ; "CPT"]

CPT

Exemplary molecules in these categories include topotecan, irinotecan, silatacan, cositecan, exatecan, lurtotecan, gimatecan, belotecan, rubitecan, SN38, diflomotecan, karenitecan, namitecan, elomotecan, delimotecan, chimmitecan, ZBH-1205, DRF-1042 and FL118.

Derivatized 7-ethyl-10-hydroxy-camptothecin (SN38) for Linkage to MAPs

Previously described nanoparticles for use in treating brain cancers and brain metastases utilized CPT as the therapeutic molecule. However, as noted above, more soluble derivatives of CPT, such as, for example SN38, provide higher therapeutic indices and lower toxicity. Accordingly, the present disclosure provides, inter alia, methods for synthesis of nanoparticles having a polymeric mucic acid backbone to which is attached a plurality of SN38 molecules. To this end, the present disclosure provides methods and compositions for synthesis of a number of derivatized variants of SN38 that are capable of being covalently joined to the MAPs described above.

Accordingly, provided herein are, inter alia, methods for synthesizing a reactive derivative of the chemotherapeutic molecule SN38. The methods involve attachment of a number of different amino acid-based linker molecules to the SN38 molecule via a SN38 hydroxyl group. SN38 and other CPT derivatives have two hydroxyl groups: a 10-hydroxyl and a 20-hydroxyl. Conjugation at the 20-hydroxyl stabilizes the active lactone form of these molecules; reducing or preventing their conversion to a less active, carboxylate form after administration to a subject; however, the 10-hydroxyl is also reactive.

In the methods described herein, the 10-hydroxyl of SN38 is first blocked from reactivity (i.e., protected); then a linker is added to the 20-hydroxyl group. Exemplary amino acid linkers include glycine, alanine, β-alanine, gamma-amino butyric acid (GABA), valine, leucine, isoleucine, pentanoic acid, hexanoic acid, arginine, histidine, lysine aspartic acid, glutamic acid, serine, threonine, asparagine, glutamine, tyrosine, tryptophan, as well as dipeptides (e.g., phenylalanine-glycine), tripeptides and oligopeptides.

Methods for the attachment of a number of different linkers to the 20-hydroxyl group of SN38 are provided herein. Each of the different linkers exemplified herein (e.g., glycine, alanine, β-alanine, leucine valine, gamma-amino butyric acid and 6-aminohexanoic acid; and others such as the dipeptide phenylalanine-glycine) after conjugation at the 20-hydroxyl group of SN38, are capable of reacting with the carboxyl groups of the MAP (via an amidation reaction between the amine group of the linker and a carboxyl group of the polymer) so as to covalently join SN38 molecules to the MAP. Each of the different linkers has different stability and affects the properties (e.g., size, density) of the resultant nanoparticles, which influence, inter alia, the rate at which SN38 is released from the nanoparticle after its traversal of the blood-brain barrier (BBB) or blood-tumor barrier (BTB).

Synthesis of 10-hydroxy Protected SN38 (10-TBDPS-SN38)

In an initial step for synthesis of derivatized SN38, a tert-butyldiphenylsilyl (TBDPS) protecting group is added to the 10-hydroxyl group of SN38 (to block reactivity at that site) by combining SN38 and tert-butlyl(chloro)diphenylsilane (TBDPSCl) in DCM and triethylamine. The mixture is refluxed (e.g., at 45° C.) for approximately 16 hours with stirring, then washed with HCl (e.g., 0.2 N), saturated NaHCO$_3$ and brine; and finally dried with MgSO$_4$ and evaporated under vacuum. The product (10-TBDPS-SN38, Compound 7) is dissolved in DCM, precipitated with hexanes and the solid is dried.

The TBDPS protecting group is selective for the 10-hydroxy group of SN38 (leaving the 20-OH group free to react in subsequent steps), and the resulting compound is less subject to spontaneous loss of the protecting group during storage; thereby providing a more stable intermediate.

A further advantage of the use of TBDPS to protect the 10-OH group of SN38 is that it can be removed under the same conditions (1 M-12 M HCl or water:TFA at between 1:1 and 1:4 v/v) as those used for the removal of the Boc protecting group from the linker attached to the 20-OH group.

Synthesis of 10-hydroxy-protected SN38 with a Protected 20-hydroxy Glycine Linker A protected glycine (Gly) linker is added to the 20-hydroxy position of 10-TBDPS-SN38 by combining 10-TBDPS-SN38 with Boc-Gly-OH at 0° C. in DCM. EDC·HCl and 4-dimethylaminopyridine (DMAP) are added and the mixture is stirred at 0° C. Stirring can be for 0.5 hour, 1 hour, 1.5 hours, 2 hours, 2.5 hours, 3 hours, 3.5 hours, 4 hours, or any interval therebetween. After stirring, the mixture is washed twice with 0.5% NaHCO$_3$, once with water, twice with 0.1 N HCl, and once with brine. The solution is dried (e.g., with MgSO$_4$) and evaporated under vacuum to yield 20-(Boc-Gly)-10-TBDPS-SN38 (Compound 8).

Synthesis of 20-(HCl·Gly)-SN38

20-(Boc-Gly)-10-TBDPS-SN38 is deprotected, at both the 10-hydroxy group and the 20-hydroxy group, by treatment with HCl (at a concentration in a range of from 1 N to 12 N) under a layer of hexane at room temperature. This generates a SN38 derivative in which the 10-hydroxy group is restored and a glycine linker is covalently attached to the 20-hydroxy group (20-(HCl·Gly)-SN38, Compound 12).

Synthesis of 10-hydroxy-protected SN38 with a Protected 20-hydroxy GABA Linker A protected gamma-amino-butyric acid (GABA) linker is added to the 20-hydroxy position of 10-TBDPS-SN38 by combining 10-TBDPS-SN38 with Boc-GABA-OH at 0° C. in DCM. EDC·HCl and DMAP are added and the mixture is stirred at 0° C. Stirring can be for 0.5 hour, 1 hour, 1.5 hours, 2 hours, 2.5 hours, 3 hours, 3.5 hours, 4 hours, or any interval therebetween. After stirring, the mixture is washed twice with 0.5% NaHCO$_3$, once with water, twice with 0.1 N HCl, and once with brine. The solution is dried (e.g., with MgSO$_4$) and evaporated under vacuum to yield 20-(Boc-GABA)-10-TBDPS-SN38 (Compound 9).

Synthesis of 20-(TFA·GABA)-SN38

20-(Boc-GABA)-10-TBDPS-SN38 is deprotected, at both the 10-hydroxy group and the 20-hydroxy group, by treatment with TFA in water, at concentrations in a range of from 1:1 to 4:1 v/v, under a layer of hexane, at room temperature. This generates a SN38 derivative in which the 10-hydroxy group is restored and a GABA linker is covalently attached to the 20-hydroxy group (20-(TFA·GABA)-SN38, Compound 13).

Synthesis of 10-hydroxy-protected SN38 with a Protected 20-hydroxy Hexanoic Acid Linker A protected 6-aminohexanoic acid (Hex) linker is added to the 20-hydroxy position of 10-TBDPS-SN38 by combining 10-TBDPS-SN38 with Boc-Hex-OH at 0° C. in DCM. EDC·HCl and DMAP are added and the mixture is stirred at 0° C. Stirring can be for 0.5 hour, 1 hour, 1.5 hours, 2 hours, 2.5 hours, 3 hours, 3.5 hours, 4 hours, or any interval therebetween. After stirring, the mixture is washed twice with 0.5% NaHCO$_3$, once with water, twice with 0.1 N HCl, and once with brine. The solution is dried (e.g., with MgSO$_4$) and evaporated under vacuum to yield 20-(Boc-Hex)-10-TBDPS-SN38 (Compound 10).

Synthesis of 20-(TFA·Hex)-SN38

20-(Boc-Hex)-10-TBDPS-SN38 is deprotected, at both the 10-hydroxy group and the 20-hydroxy group, by treatment with TFA in water, at concentrations in a range of from 1:1 to 4:1 v/v, under a layer of hexane, at room temperature. This generates a SN38 derivative in which the 10-hydroxy group is restored and a Hex linker is covalently attached to the 20-hydroxy group (20-(TFA·Hex)-SN38, Compound 14).

Synthesis of 10-hydroxy-protected SN38 with a Protected 20-hydroxy Valine Linker A protected valine (Val) linker is added to the 20-hydroxy position of 10-TBDPS-SN38 by combining 10-TBDPS-SN38 with Boc-Val-OH at 0° C. in DCM. EDC·HCl and DMAP are added and the mixture is stirred at 0° C. Stirring can be for 0.5 hour, 1 hour, 1.5 hours, 2 hours, 2.5 hours, 3 hours, 3.5 hours, 4 hours, or any interval therebetween. After stirring, the mixture is washed twice with 0.5% NaHCO$_3$, once with water, twice with 0.1 N HCl, and once with brine. The solution is dried (e.g., with MgSO$_4$) and evaporated under vacuum to yield 20-(Boc-Val)-10-TBDPS-SN38 (Compound 11).

Synthesis of 20-(HCl·Val)-SN38

20-(Boc-Val)-10-TBDPS-SN38 is deprotected, at both the 10-hydroxy group and the 20-hydroxy group, by treatment with HCl (at a concentration in a range of from 1 N to 12 N) under a layer of hexane at room temperature. This generates a SN38 derivative in which the 10-hydroxy group is restored and a valine linker is covalently attached to the 20-hydroxy group (20-(HCl·Val)-SN38, Compound 15).

Use of the Same Protecting Group at Both 10- and 20-OH Groups of SN38

An alternate route for synthesizing a reactive derivative of SN38 with an amino acid linker is to place a Boc-O protecting group on the 10-OH group and a Boc-amino acid protecting group on the 20-OH. When this compound (20-(Boc-aminoacyl)-10-OBoc-SN38) is reacted with TFA, the 10-OH group is restored and the TFA salt of an amino acid linker is appended to the 20-OH. Using this method 20-Boc-glycyl, -alanyl, -β-alanyl, -leucyl and -valyl derivatives of SN38 have been synthesized. See below and Examples 33-35. Other amino acids that can be used in this method include GABA, isoleucine, and hexanoic acid, as well as dipeptides, e.g., phenylalanine-glycine.

26

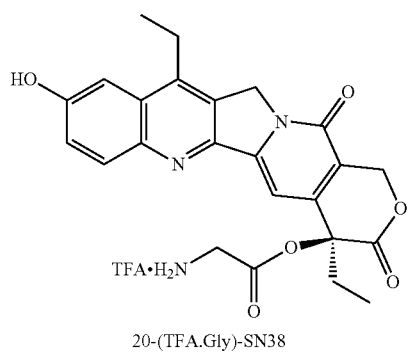

20-(TFA.Gly)-SN38

32

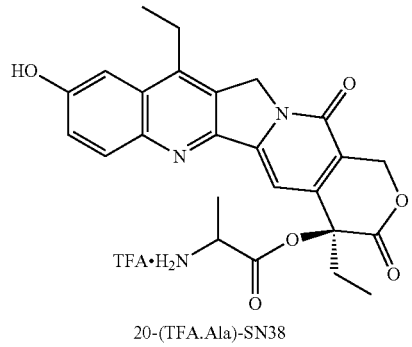

20-(TFA.Ala)-SN38

33

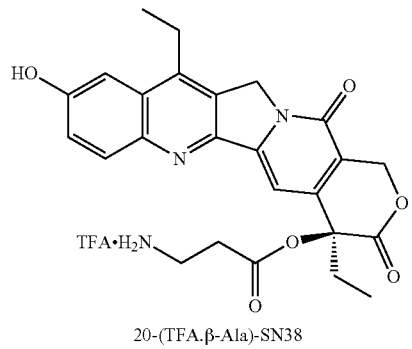

20-(TFA.β-Ala)-SN38

34

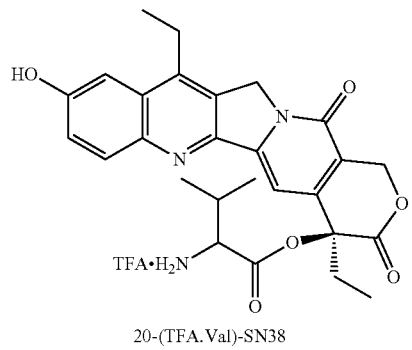

20-(TFA.Val)-SN38

36

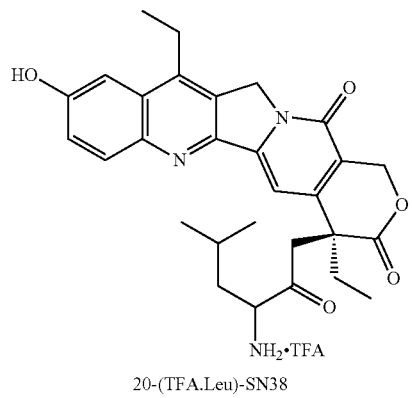

20-(TFA.Leu)-SN38

Synthesis of Polymer-Drug Conjugates

Provided herein are, inter alia, methods for forming polymer-drug conjugates (i.e., MAP-linker-SN38 nanoparticles), by covalent attachment of derivatized SN38 to a MAP. A number of different conjugates are provided, which differ in the nature (i.e., size and chemical properties) of the linker between the polymer and the drug. The different conjugates are made by using SN38 that has been derivatized with various types of linker. In one embodiment the linker is a glycyl (Gly) moiety. In one embodiment the linker is a valyl (Val) moiety. In one embodiment, the linker is a gamma-amino butyric acid (GABA) moiety. In one embodiment, the linker is a 6-aminohexanoic acid (Hex) moiety. In one embodiment the linker is an alanyl (Ala) moiety. In one embodiment the linker is a β-alanyl (β-Ala) moiety. In one embodiment the linker is a leucyl (Leu) moiety.

To form polymer-drug conjugates, MAP is dissolved in DMSO, following which EDC·HCl and N-hydroxysuccinimide (NHS) are added. After addition of EDC·HCl and NHS, derivatized SN38 and DIPEA are added and the mixture is stirred at room temperature for approximately 18 hours. Derivatized SN38 can be, for example, 20-(HCl·Gly)-SN38, 20-(HCl·Val)-SN38, 20-(TFA·GABA)-SN38, 20-(TFA·Hex)-SN38, 20-(TFA·Gly)-SN38, 20-(TFA·Ala)-SN38, 20-(TFA. β-Ala)-SN38, 20-(TFA·Val)-SN38 or 20-(TFA·Leu)-SN38. The reaction mixture is next dialyzed against DMSO, then against water at pH 4 using a 10 kDa membrane. The dialyzed product is filtered (e.g., through a 0.22 μm filter), frozen and lyophilized. Depending on the derivatized SN38 that is used, the products are MAP-Gly-SN38 (Compound 16); MAP-GABA-SN38 (Compound 17), MAP-Hex-SN38 (Compound 18), MAP-Val-SN38 (Compound 19), MAP-Ala-SN38 (Compound 37), MAP-β-Ala-SN38 (Compound 38) or MAP-Leu-SN38 (Compound 39).

Formation of Nanoparticles

To convert a polymer-drug conjugate (i.e., any one of Compounds 16, 17, 18 or 19, 37, 38 or 39) to nanoparticles, the lyophilized polymer-drug conjugate is dissolved to a concentration of 1-10 mg/mL (e.g., 4 mg/mL) in water at pH 4. The solution is then filtered and can be frozen until further use.

The size of the nanoparticles ranges from about 20 to about 60 nm in diameter. Exemplary nanoparticle diameters are 15 nm, 16 nm, 17 nm, 18 nm, 19, nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 45 nm, 50 nm, 55 nm, 60 nm or larger.

Release of SN38 from Nanoparticles In Vitro

When nanoparticles at a concentration of 0.1 mg SN38/mL were incubated in a humidified oven at 37° C. in PBS at a pH of 6.5, 7.0 or 7.4; release of SN38 from the MAP-Gly-SN38, MAP-GABA-SN38, MAP-Hex-SN38, MAP-Val-SN38, MAP-Ala-SN38, MAP-β-Ala-SN38 and MAP-Leu-SN38 nanoparticles all exhibited first-order kinetics. A strong dependence of release rate with pH was observed. As the pH increased from 6.5 to 7.4, the release half-lives decreased for all nanoparticle formulations, indicating that hydrolysis plays an important role in the release of SN38. Longer half-lives were observed for nanoparticles with more hydrophobic and sterically hindered linkers.

Derivatized CPT for Linkage to MAPs

In certain embodiments, the present disclosure provides nanoparticles containing CPT as a therapeutic agent. A derivative of CPT conjugated to an amino acid (e.g., 20-(TFA·Gly)-CPT) is used for synthesis of said nanoparticles. Exemplary amino acid linkers include glycine, alanine, β-alanine, gamma-amino butyric acid (GABA), valine, leucine, isoleucine, pentanoic acid, hexanoic acid, as well as dipeptides (e.g., phenylalanine-glycine), tripeptides and oligopeptides.

20-(TFA·Gly)-CPT is synthesized in two steps. In the first step, CPT is combined with Boc-Gly-OH in DMAP in an inert atmosphere (e.g., under argon), and the reactants are made into a slurry by addition of DCM. DIC is then added dropwise to the reaction mixture over the course of several minutes, after which the mixture is stirred for several hours (e.g., three hours) at room temperature. Approximately half of the solvent is then removed under vacuum, and chilled MeOH is added to precipitate the product (20-(Boc-Gly)-CPT, Compound 21), which is obtained by filtration. Solids are washed with chilled MeOH and chilled methyl tert-butyl ether (MTBE) and dried under vacuum. See Example 30.

In the second step, TFA is added gradually to a stirring suspension of 20-(Boc-Gly)-CPT in DCM and the mixture is stirred for several hours (e.g., 2 hours). The product (20-(TFA·Gly)-CPT, Compound 22) is then precipitated with MTBE, filtered, washed and dried under vacuum. See Example 31

Additional CPT derivatives can be made by using other Boc-protected amino acids (or peptides), in place of Boc-Gly-OH. For example, using Boc-Ala-OH as starting material, one obtains 20-(Boc-Ala)-CPT (Compound 41) and 20-(TFA·Ala)-CPT (Compound 45). Using Boc-β-Ala-OH as starting material, one obtains 20-(Boc-β-Ala)-CPT (Compound 42) and 20-(TFA·β-Ala)-CPT (Compound 46). Using Boc-Val-OH as starting material, one obtains 20-(Boc-Val)-CPT (Compound 40) and 20-(TFA·Val)-CPT (Compound 47). Using Boc-GABA-OH as starting material, one obtains 20-(Boc-GABA)-CPT (Compound 43) and 20-(TFA·GABA)-CPT (Compound 48). Using Boc-Phe-Gly-OH as starting material, one obtains 20-(Boc-Phe-Gly)-CPT (Compound 44) and 20-(TFA·Phe-Gly)-CPT (Compound 49).

Synthesis of CPT-Polymer Conjugate

Conjugates of CPT and MAP are provided in certain embodiments. To synthesize these conjugates, MAP and 20-(TFA·aminoacyl)-CPT (see preceding section for exemplary amino acid and peptide derivatives of CPT) are dissolved in DMSO in an inert atmosphere (e.g., under argon). In a separate vessel, (7-azabenzotriazol-1-yloxy)trispyrrolidinophosphonium hexafluorophosphate (PyAOP) is dissolved in DMSO. The PyAOP solution is then added to the MAP/20-(TFA·aminoacyl)-CPT solution and stirred for several minutes (e.g., 2 min), then DIPEA is added and the reaction mixture is stirred in the dark at room temperature for 12-24 hours (e.g., 18 hours). Product is precipitated (optionally in several batches) with cold (0-4° C.) ethyl acetate (EtOAc) and washed with cold EtOAc. The product can be further isolated by freeze-drying. See Example 32.

Nitrophenylboronic Acid (NPBA)-polyethylene Glycol (PEG) Conjugates

In certain embodiments, macromolecules such as targeting (homing) molecules or large-molecule therapeutics (e.g., antibodies) are linked to a MAP via a nitrophenyl boronic acid-polyethylene glycol (NPBA-PEG) linker. Such a NPBA-PEG linker can be synthesized by combining an amine derivative of a PEG (e.g., $PEG_{3.5k}$, $PEG_{5k}$) with a carboxyl derivative of NPBA to form a NPBA-PEG-acetic acid (AA) conjugate joined by an amide linkage. In certain embodiments, the PEG derivative contains an amino group at one terminus (for reaction with NPBA) and a carboxyl group at the opposite terminus (which can, in a subsequent reaction, be activated to react with a macromolecule such a polypeptide). See Example 36.

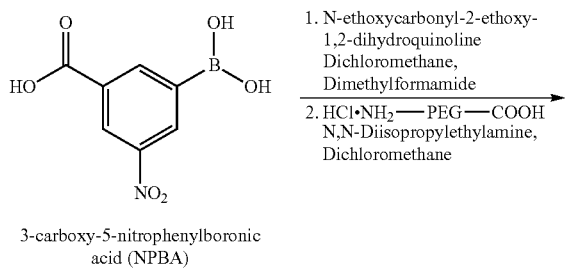

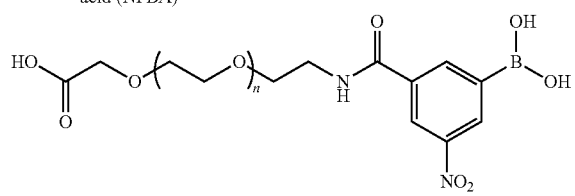

In certain embodiments, n is a number in a range of from 2 to 2,000 or any integral values therebetween; e.g., from 100 to 300, from 20 to 300, from 120 to 180, or from 140 to 160.

In certain embodiments, the value of n is such that the PEG (i.e. —CH$_2$—CH$_2$—O—) portion of the compound has a weight average molecular weight in a range of from about 2 to about 15 kDa; e.g., about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, or about 15 kDa.

The NPBA-PEG-AA conjugate is activated, for reaction with a polypeptide (such as, for example, transferrin), by forming a pentafluorophenyl (PFP) derivative. In these embodiments, bis(pentafluorophenyl) carbonate is combined with a NPBA-PEG-AA conjugate to form a NPBA-PEG-pentafluorophenyl ester (e.g., NPBA-PEG$_{5k}$-AA-PFP). See Example 37.

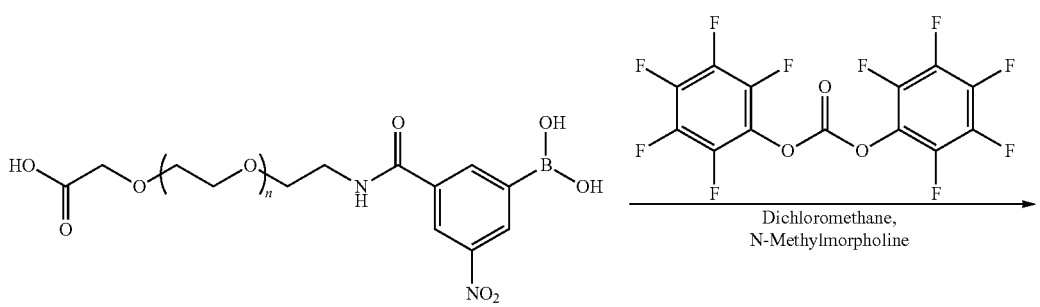

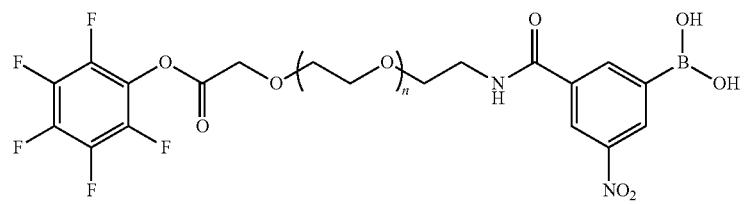

In certain embodiments, n is a number in a range of from 2 to 2,000 or any integral values therebetween; e.g., from 100 to 300, from 20 to 300, from 120 to 180, and/or from 140 to 160.

In certain embodiments, the value of n is such that the PEG (i.e. —CH$_2$—CH$_2$—O—) portion of the compound has a weight average molecular weight in a range of from about 2 to about 15 kDa; e.g., about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, or about 15 kDa.

Polymer Conjugates Containing Homing (Targeting) Molecules

In certain embodiments, MAPs as described herein contain, instead of or in addition to a small molecule therapeutic such as CPT or SN38, a homing (or targeting) molecule. Targeting molecules are known in the art and include, for example, small molecules (e.g., vitamins, e.g., folate), saccharides (e.g., mannose, allose, altrose, glucose, gulose, idose, galactose, talose, disaccharides, trisaccharides, oligosaccharides), peptides (e.g., RGD), polypeptides (e.g., antibodies, proteins that bind cell-surface receptors such as transferrin), nucleic acids, peptoids and peptide nucleic acids (PNAs).

For example, MAPs (and nanoparticles made from MAPs) can comprise the homing molecule transferrin, which targets the polymer (or a nanoparticle formed from the polymer) to endothelial cells of the blood-brain or blood-tumor barriers. In these embodiments, the homing molecule is attached to a NPBA-PEG polymer by way of reaction with a PFP active ester, which is described above. Inasmuch as primary amine groups in proteins react with the PFP active ester, attachment of holo-transferrin to the NPBA-PEG-pentafluorophenyl ester is achieved by combining the ester with holo-transferrin. Progress of the reaction is monitored by HPLC, and the mono-PEGylated transferrin product (e.g., mono-NPBA-PEG$_{5k}$-Tf) is purified by hydrophobic interaction chromatography (HIC), based on the differential binding of mono-PEGylated transferrin compared to fractions with higher degrees of PEGylation (e.g., di- and tri-PEGylated fractions). See Examples 38 and 39. This method prevents loss of iron from transferrin during purification, as occurred using previous methods, thereby preserving the holo-transferrin structure.

Polymer Conjugates Containing Large Molecule Therapeutics

In certain embodiments, MAPs as described herein contain, instead of or in addition to a small molecule therapeutic such as CPT or SN38, a large molecule therapeutic. Large molecule therapeutics are known in the art and include, for example, therapeutic polypeptides (e.g., antibodies, enzymes, and bioactive proteins) and nucleic acids.

Exemplary therapeutic polypeptides include, but are not limited to antibodies, such as trastuzumab (anti-Her2), anti-Her3, anti-Trop2, anti-PSMA, anti-LIV-1, anti-FOLR1, anti-DLL3, anti-PDGF, anti-FRalpha, anti-PTK7, anti-mesothelin, anti-c-MET, anti-MUC1, anti-CD70, anti-CD74, anti-CD30, anti-CD33, anti-FLT3, anti-CD22, anti-CD20, and anti-CD19.

Certain polypeptide therapeutics, such as antibodies directed to tumor markers like those exemplified in the previous paragraph, are also used at targeting (homing) molecules.

For example, MAPs (and nanoparticles made from MAPs) can comprise the anti-Her2 antibody trastuzumab. In these embodiments, the antibody is attached to a NPBA-PEG polymer by way of reaction with a PFP active ester, which is described above.

Inasmuch as the primary amine groups in proteins react with the PFP active ester, attachment of trastuzumab to the NPBA-PEG-pentafluorophenyl ester is achieved by combining the ester with trastuzumab. Progress of the reaction is monitored by HPLC and the mono-PEGylated trastuzumab product (e.g., mono-NPBA-PEGk-Tras) is purified by HIC, based on the differential binding on mono-PEGylated trastuzumab compared to fractions containing higher degrees of PEGylation (e.g., di- and tri-PEGylated fractions). See Examples 41 and 42.

Determination of Number of Polymer Strands Per Nanoparticle

To determine the number of polymer strands per nanoparticle, the average molecular weight of the nanoparticle is divided by the molecular weight of the corresponding polymer-drug (i.e., MAP-SN38) conjugate.

The molecular weight of a nanoparticle is determined by gel permeation chromatography (GPC) using PEO standards with nominal molecular weights of 100 kDa and 200 kDa. The molecular weight of the polymer-drug conjugate is calculated from the molecular weight of the polymer (i.e., MAP) used in the synthesis of the conjugate, adjusted for drug loading as follows:

$$MW_{conjugate} = MW_{polymer}/(1-T)$$

where $MW_{polymer}$ is the molecular weight of the MAP used in the synthesis of the conjugate, and T is the fractional loading of the therapeutic agent, expressed as a decimal fraction.

Strands per particle (SpP), as used herein, is the number of mucic acid polymer ("MAP") therapeutic agent conjugate molecules present in a particle or nanoparticle. For purposes of determining SpP, a particle or nanoparticle is an entity having at least one MAP-therapeutic agent-protein conjugate molecule which, at the concentration suitable for administration to humans, behaves as a single unit in any aqueous solution, e.g. water at neutral pH, PBS at pH 7.4, or any formulation in which it will be administered to patients. For purposes of calculating strands per particle, a MAP-therapeutic agent conjugate molecule is a single MAP polymer with its covalently linked therapeutic agent.

Methods disclosed herein provide for evaluating a particle wherein said particles comprise one or more MAP-therapeutic agent conjugate molecules. Generally, the method requires providing a sample comprising a plurality of said particles and determining a value for the number of MAP-therapeutic agent conjugates per particle in the sample, to thereby evaluate a preparation of particles. The value for a particle sample will be a function of values obtained for a plurality of particles.

As discussed above, SpP is defined as the number of MAP-therapeutic agent conjugate molecules that self-assemble into a particle or nanoparticle, thus SpP=[MAP–therapeutic agent conjugate molecule]/$P$ (or NP)

where [MAP-therapeutic agent conjugate molecules] is the number of MAP-therapeutic agent conjugate molecules, and P (or NP) is a single particle (or nanoparticle).

In certain embodiments, the method further comprises comparing the determined value with a reference value. The comparison can be used in a number of ways. By way of example, in response to a comparison or determination made in the method, a decision or step is taken, e.g., a production parameter in a process for making a particle is altered, the sample is classified, selected, accepted or discarded, released or withheld, processed into a drug product, shipped, moved to a different location, formulated, e.g., formulated with another substance, e.g., an excipient, labeled, packaged, released into commerce, or sold or offered for sale. For example, based on the result of the determination, or upon comparison to a reference standard, the batch from which the sample is taken can be processed, e.g., as just described.

To calculate the number of strands per particle, the size of the particle is determined, e.g. molecular weight by light scattering of self-assembled particles, and the size of individual polymers, e.g. molecular weight by light scattering of individual polymers, and the loading of therapeutic agent, e.g. mass %. With these values, SpP is calculated as follows:

$$SpP=MW_{particle}/(MW_{conjugate})$$

where $MW_{particle}$ is the molecular weight of the particle, and $MW_{conjugate}$ is the molecular weight of a MAP-therapeutic agent conjugate molecule which is calculated as follows:

$$MW_{conjugate}=MW_{polymer}/(1-T\%)$$

where $MW_{polymer}$ is the molecular weight of the MAP, and T % is the percent loading of therapeutic agent expressed as a decimal, e.g. 10% loading results in T %=0.1. The determination of SpP is demonstrated with MAPs with varying linkers and drugs. MAPs of the same molecular weight with CPT and SN38 result in ~1.5-2.5 strands per particle. Different linkers alter the strands per particle and therefore density of the particles, which is demonstrated with SN38. The linkers glycine, gamma-amino butyric acid, hexanoic acid, alanine, β-alanine, leucine and valine vary the strands per particle from ~1.3-~4.6 strands per particle.

Polymer molecular weight distribution and particle dispersity: MAPs are synthesized such that they have a range of molecular weights. Molecules of varied molecular weight provide varying contributions to particle diameter and the strands per particle. Particles could form with MAPs, here considered strands, that are smaller or larger than average. Strands may also associate to a maximum size which could be shear-limited.

Particle shape: Particle shape is assumed to be approximately spherical. Self-assembly is assumed to be driven by the hydrophobic region created by the therapeutic agents of the MAP-therapeutic agent conjugate molecule.

Formulations, Kits, and Routes of Administration

Therapeutic compositions comprising nanoparticles as disclosed herein are also provided. Such compositions typically comprise the nanoparticles and a pharmaceutically acceptable carrier. Supplementary active compounds can also be incorporated into nanoparticle compositions.

The therapeutic compositions disclosed herein are useful for, inter alia, treating cancer, cancer metastases and other disorders of the brain and central nervous system. Accordingly, a "therapeutically effective amount" of a composition comprising nanoparticles is any amount that reduces symptoms or, e.g., stimulates tumor regression. For example, dosage amounts of nanoparticles can vary from about 0.1-1.0 mg/kg body weight, or from about 0.5 to 2.0 mg/kg body weight or from about 1-5 mg/kg body weight or from about 1 mg/kg body weight to about 10 mg/kg body weight or more (or any integral value therebetween); with a frequency of administration of, e.g., hourly, twice per day, once per day, twice per week, once per week, twice per month, once per month, depending upon, e.g., body weight, route of administration, severity of disease, etc. Thus, a therapeutically effective amount can comprise a plurality of administrations of the same amount, or different amounts, of nanoparticles. In certain embodiments, a single administration of nanoparticles is a therapeutically effective amount.

In certain embodiments, nanoparticles are administered at a dosage of 1-20 mg nanoparticle (or any integral or decimal value therebetween) per square meter of the surface area of the body of the subject, as is typical for dosages of chemotherapeutics.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The nanoparticles described herein can be suspended in a physiologically compatible carrier for administration. As used herein, the term "physiologically compatible carrier" refers to a carrier that is compatible with the nanoparticles and with any other ingredients of the formulation, and is not deleterious to the recipient thereof. Those of skill in the art are familiar with physiologically compatible carriers. Examples of suitable carriers include water (e.g., pH 4 water), phosphate-buffered saline, Hank's balanced salt solution+/−glucose (HBSS), and multiple electrolyte solutions such as, e.g., Plasma-Lyte™ A (Baxter).

The volume of a nanoparticle suspension administered to a subject will vary depending on the site of administration, treatment goal and number of nanoparticles in solution. Typically the amount of nanoparticles administered will be a therapeutically effective amount. As used herein, a "therapeutically effective amount" or "effective amount" refers to the number of administered nanoparticles which are required to effect treatment of the particular disorder; i.e., to produce a reduction in the amount and/or severity of the symptoms associated with that disorder. For example, in the case of a cancer metastasis to the brain, administration of a therapeutically effective amount of nanoparticles results in reduction and/or reversal of the symptoms of metastasis; e.g., regression of the metastatic tumor. Therapeutically effective amounts vary with the type and extent of brain damage, and can also vary depending on the overall condition of the subject.

The disclosed therapeutic compositions can also include pharmaceutically acceptable materials, compositions or vehicle, such as a liquid or solid filler, diluent, excipient, solvent or encapsulating material, i.e., carriers. These carriers can, for example, stabilize the nanoparticles and/or facilitate the retention of the nanoparticles in the body. Each carrier is "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol and polyethylene glycol; polyols, such as glycerin, sorbitol and mannitol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Nanoparticles can be administered to a subject by any suitable route, including, but not limited to, inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard practice. Administration of the compounds described herein can be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or by oral administration. A pharmaceutical composition of the nanoparticles described herein can be for administration by injection, or for oral, pulmonary, nasal, transdermal, or ocular administration.

Exemplary formulations include, but are not limited to, those suitable for parenteral administration, e.g., intrapulmonary, intravenous, intra-arterial, intra-ocular, intra-cranial, sub-meningeal, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered intracranially at or near a site of brain injury or metastasis. Such localized delivery allows for the delivery of the composition non-systemically, thereby reducing the body burden of the composition as compared to systemic delivery. Local delivery can be achieved, for example, by intra-cranial injection, or through the use of various medically implanted devices including, but not limited to, stents and catheters, or can be achieved by inhalation, phlebotomy, or surgery. Methods for coating, implanting, embedding, and otherwise attaching desired agents to medical devices such as stents and catheters are established in the art and contemplated herein.

Another aspect of the present disclosure relates to kits for carrying out the administration of nanoparticles, optionally in combination with another therapeutic agent, to a subject. In one embodiment, a kit comprises a composition of nanoparticles formulated in a pharmaceutical carrier, suitable for administration, e.g., by injection.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g., amounts, temperature, etc.) but some experimental error and deviation should be accounted for. Unless indicated otherwise, temperature is in degrees Centigrade, pressure is at or near atmospheric. Any reference to molecular weight, unless said otherwise, is intended to refer to number average molecular weight.

Examples 1-4 describe conversion of mucic acid to a polymerizable mucic acid monomer (MAM). Examples 5 and 6 describe polymerization of MAM to form a mucic acid polymer (MAP). Examples 7-15 describe derivatization of 7-ethyl-10-hydroxy-camptothecin (SN38), with four different amino acid-based linkers, to a form capable of reacting with MAP to form covalent MAP-SN38 conjugates. Examples 16-20 describe reactions used to synthesize MAP-SN38 conjugates joined by amino acid-based linkers. Example 21 describes a method for conversion of MAP-SN38 conjugates to nanoparticles. Examples 22 and 23 describe characterization of the MAP-SN38 nanoparticles. Examples 24-29 describe routes for preparative-scale synthesis of a MAP. Examples 30-32 describe derivatization of camptothecin (CPT) and its attachment to a MAP. Examples 33-35 describe derivatization of SN38 for attachment to a MAP. Examples 36 and 37 describe synthesis of a nitrophenyl boronic acid-polyethylene glycol (NPBA-PEG) polymer with a reactive terminus suitable for protein conjugation. Examples 38-40 describe conjugation of a targeting (homing) molecule to a NPBA-PEG polymer and characterization of the product. Examples 41-43 describe conjugation of a large molecule therapeutic to a NPBA-PEG polymer and characterization of the product.

Example 1. Synthesis of N-Boc-Protected Mucic Acid Diamine (Compound 2)

A 1 L round bottom flask with 18 g (86 mmol) of mucic acid and a magnetic stir bar was charged with 400 mL of methanol (MeOH) and 1.4 mL of concentrated sulfuric acid. The mixture was heated to reflux (85° C.) overnight (~18 hours) under constant stirring. After ~18 hours, 32 mL triethylamine (TEA) was added the flask and the mixture was allowed to stir at reflux (85° C.) for 60 minutes. To the reaction mixture was then added 30 g (187 mmol) N-Boc-ethylenediamine dissolved in 50 mL of MeOH. The reaction was stirred at reflux (85° C.) overnight (~18 hours). The reaction mixture was allowed to cool to room temperature, filtered, and washed with MeOH. The collected solids were then taken into 450 mL of MeOH and refluxed under constant stirring for 1 hour. The reaction mixture was allowed to cool to room temperature, filtered under vacuum, and washed with MeOH. Collected solids were dried overnight under vacuum to afford 26.1 g (52.8 mmol, 62% yield) of N-Boc-protected mucic acid diamine (2).

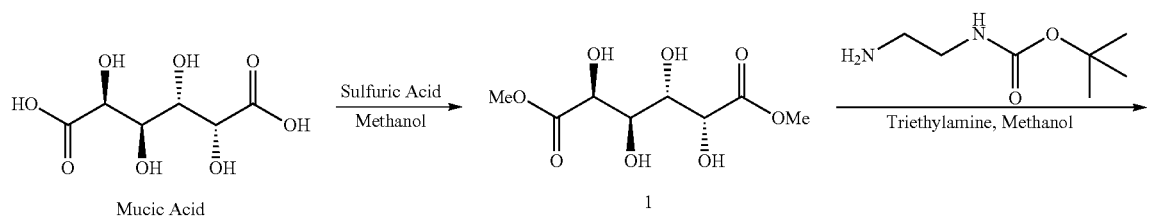

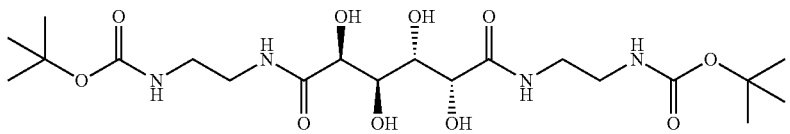

Example 2. Synthesis of Mucic Acid Diaminochloride (Compound 3)

To a 500 mL round bottom flask with 25.9 g (52 mmol) N-Boc-protected mucic acid diamine (2) and magnetic stir bar was added 466 mL of 3 M aqueous hydrochloric acid (HCl) in MeOH slowly under constant stirring. Following slow addition of HCl, the reaction flask was moved to an orbital shaker and shaken overnight at room temperature. The reaction slurry was filtered, and the solids were washed with MeOH three times (150 mL). Collected solids were dried overnight for several hours under vacuum at 35° C. to afford 18.0 g (49 mmol, 94% yield) of mucic acid diaminochloride (3).

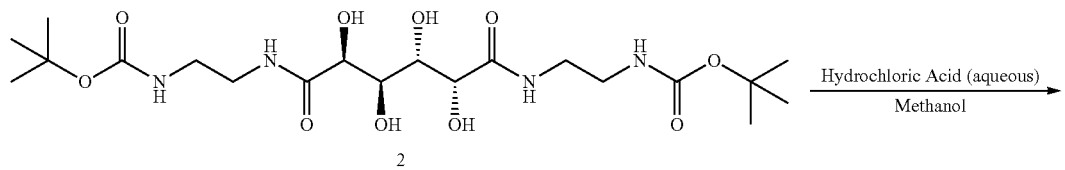

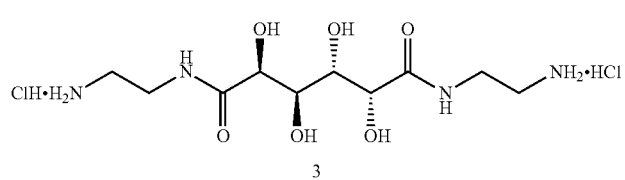

Example 3. Synthesis of Mucic Acid di(Asp(OtBu)-Boc) (Compound 4)

To a 250 mL round bottom flask with 14.9 g (51 mmol) Boc-L-aspartic acid 4-tert-butyl ester, 6 g (54 mmol) hydroxypyridine N-oxide (HOPO), and a magnetic stir bar was added 140 mL of acetonitrile (ACN) and 8.5 mL (54 mmol) N,N'-diisopropylcarbodiimide (DIC). This reaction mixture was allowed to stir for 10 minutes. To the reaction flask was then added a suspension of 6.3 g (17 mmol) mucic acid diaminochloride (3) dissolved in a mixture of water (55 mL) and TEA (5.4 mL). The reaction mixture was heated (80° C.) under constant magnetic stirring for ~24 hours. Following heating, ACN was removed from the reaction mixture using vacuum. To the concentrated reaction was added additional water (150 mL), and the mixture was heated (85° C.) for 1 hour. Following cooling, the reaction mixture was collected by vacuum filtration, and washed with water three times (100 mL). The washed solids were returned to a round bottom flask along with ACN (150 mL). The reaction mixture was heated to reflux under constant stirring until soluble. Following cooling, the reaction mixture was collected by filtration and washed with chilled ACN three times (100 mL). The collected solids were again returned to a round bottom flask along with ACN (150 mL) and the reaction mixture was heated to reflux under constant stirring for ~1 hour. Following cooling, the reaction mixture was collected by filtration and washed with chilled ACN three times (100 mL). Collected solids were dried overnight under vacuum to afford 5.9 g (7 mmol, 41% yield) of mucic acid di(Asp(OtBu)-Boc) (4).

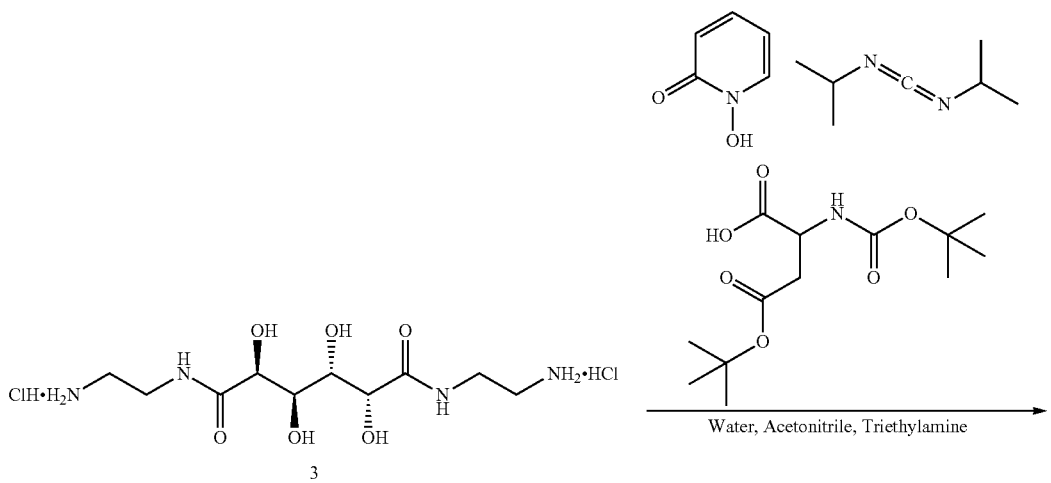

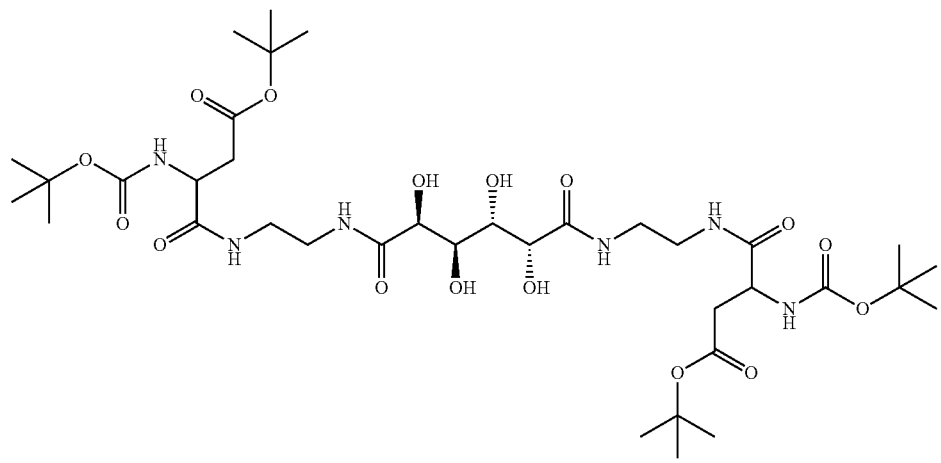

Example 4. Synthesis of Mucic Acid Monomer (MAM) (Compound 5)

To a 40 mL vial charged with 1 g (1 mmol) mucic acid di(Asp(OtBu)-Boc) (4) and a magnetic stir bar was added dichloromethane (DCM, 7.5 mL). To this reaction mixture under constant stirring, trifluoroacetic acid (TFA, 7.5 mL, 98 mmol) was added slowly. After stirring at room temperature for 1 hour, the reaction mixture was precipitated by slow addition of methyl tert-butyl ether (MTBE, 100 mL). The precipitated mixture was centrifuged and subsequently washed one time with MTBE (100 mL). The collected solids were dried under vacuum, and then dissolved in water (30 mL). The dissolved product was then passed through a 0.22 μm filter, frozen, and lyophilized to afford 0.2767 g (0.384 mmol, 32% yield) of MAM (5).

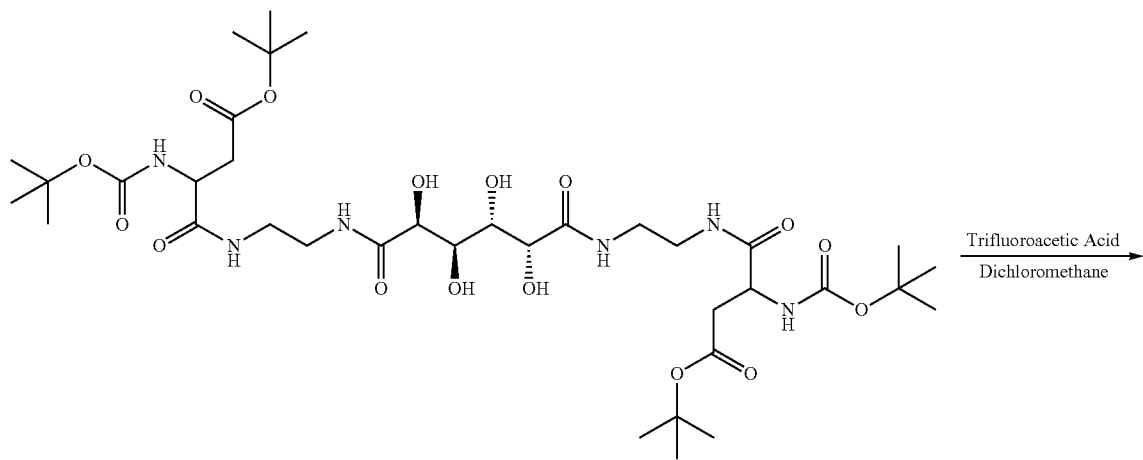

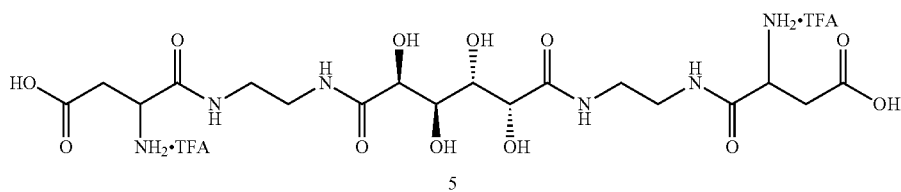

Example 5. Synthesis of Mucic Acid Polymer (MAP) (Compound 6)

A 10 mL round bottom flask with 224 mg (0.30 mmol) of MAM (5), 1 g of di(succinimidyl propionate)-PEG (diSPA-PEG$_{3.5k}$) (0.27 mmol) and a magnetic stir bar was sealed, and the two solids were dried under vacuum at room temperature for 4 hours. To the reaction flask was then added 4.1 mL of anhydrous dimethyl sulfoxide (DMSO), and the mixture was heated (35° C.). Following solubilization, 208 μL of anhydrous N,N'-diisopropylethylamine (DIPEA, 1.19 mmol) was added to the reaction mixture. The reaction mixture was heated (35° C.) under constant magnetic stirring for 66 hours. The reaction mixture was dialyzed against DMSO, and then water using a 10 kDa membrane. The dialyzed product was then passed through a 0.22 μm filter, frozen, and lyophilized to afford 1.03 g (quantitative yield) of MAP (6).

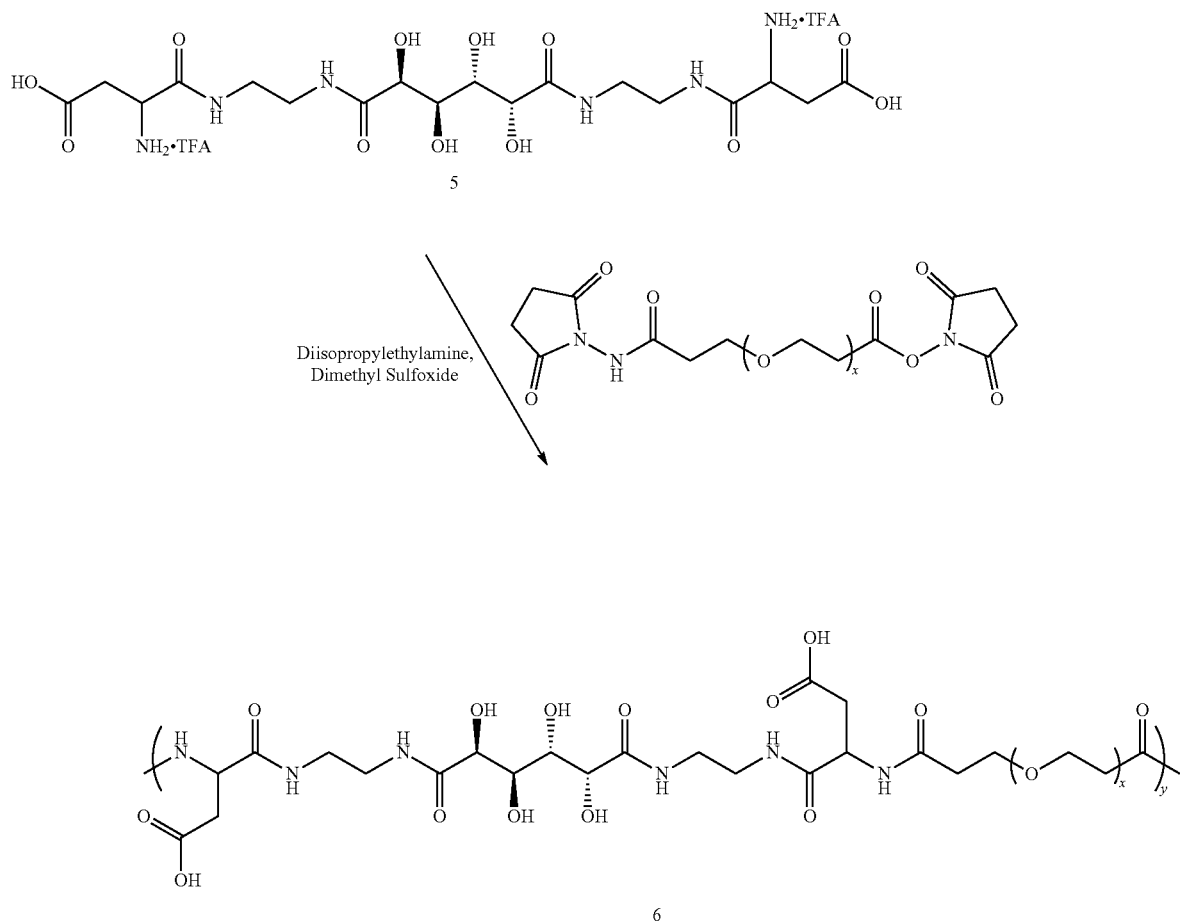

For Compound 6 synthesized by this method, x was about 80 and y was about 16. Accordingly, Compound 6 had an average molecular weight of about 65 kDa, determined as the arithmetic mean of the number average molecular weight and the weight average molecular weight. These values will change if a different starting material (e.g., diSPA-PEG$_{2k}$) is used (e.g., x is about 46 for 2 kDa PEG).

Example 6. Determination of MAP Molecular Weight

MAP (6) molecular weight was determined on a Malvern Omnisec gel permeation chromatography (GPC) system, which comprised a solvent delivery pump, degasser, autosampling injector, column compartment, refractive index detector, and light scattering detector. Samples were prepared for analysis by dissolving MAP (6) at a known concentration in the range of 1-5 mg/mL in phosphate-buffered saline (PBS)+0.02% sodium azide. Once fully dissolved, samples were passed through a 0.45 µm filter. Absolute molecular weight was determined by injecting 100 µL of filtered sample onto 2×PL Aquagel-OH 40 columns (Agilent) at a flow rate of 0.7 mL/min. Analysis was performed at 30° C. The resulting polymer peak was analyzed using Malvern OMNISEC software.

Example 7. Synthesis of 10-TBDPS-SN38 (Compound 7)

A 250 mL round bottom flask with 2 g (5.10 mmol) SN38 and magnetic stir bar was charged with 100 mL of anhydrous DCM and 4.2 mL (30.58 mmol) of TEA. To the reaction mixture was then added 7.9 mL (30.58 mmol) of tert-butyl (chloro)diphenylsilane (TBDPSCl). The mixture was heated to reflux (50° C.) overnight (~16 hours) under constant stirring, and then washed with 0.2 N HCl (2×50 mL), saturated NaHCO$_3$ (100 mL) and brine (100 mL). The organic solution was dried with MgSO$_4$, and evaporated under vacuum. The residue was dissolved in anhydrous DCM, and precipitated with hexanes. This precipitation was repeated to further remove excess TBDPSCl. The solids were dried under vacuum to afford 1.2 g (1.9 mmol 37% yield) of 10-TBDPS-SN38 (7).

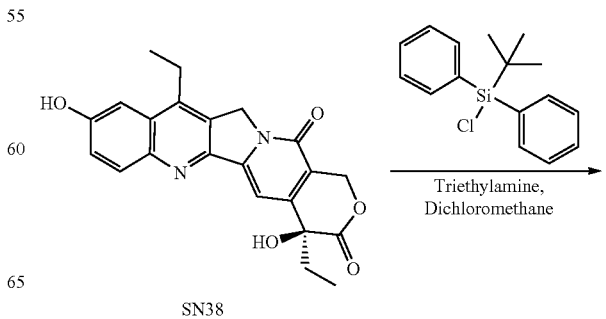

Example 8. Synthesis of 20-(Boc-Gly)-10-TBDPS-SN38 (Compound 8)

To a 40 mL vial with 0.5 g (0.8 mmol) 10-TBDPS-SN38 (7) was added 8.9 mL anhydrous DCM and a magnetic stir bar. Following solvent addition, the reaction was cooled to 0° C. To a separate vial was added 0.35 g Boc-Gly-OH (2.0 mmol), 0.39 g (2.0 mmol) 1-(3-dimethylaminopropyl)-3-ethylcarbodiimide hydrochloride (EDC·HCl), 0.1 g (0.8 mmol) 4-dimethylaminopyridine (DMAP), and 3.8 mL anhydrous DCM. The contents of the second vial were then transferred to the flask containing 7. After stirring at 0° C. for 3 hours, the mixture was washed with 0.5% NaHCO$_3$ (2×50 mL), water (50 mL), 0.1 N HCl (2×50 mL) and brine. The organic solution was dried with MgSO$_4$, and evaporated under vacuum to afford 0.54 g crude 20-(Boc-Gly)-10-TBDPS-SN38 (8) (0.7 mmol, 86% yield).

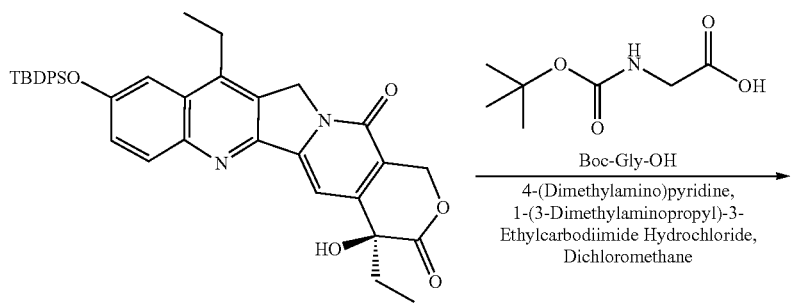

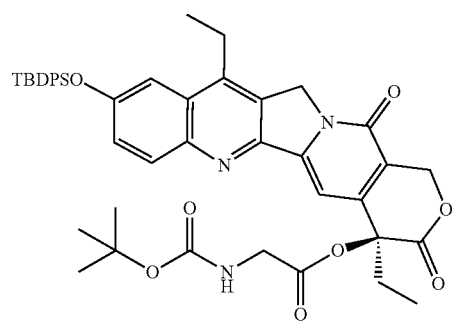

Example 9. Synthesis of 20-(Boc-GABA)-10-TBDPS-SN38 (Compound 9)

To a 40 mL vial with 1 g (1.6 mmol) 10-TBDPS-SN38 (7) was added 17.7 mL anhydrous DCM and a magnetic stir bar. Following solvent addition, the reaction was cooled to 0° C. To a separate vial was added 0.82 g (4.0 mmol) Boc-GABA-OH, 0.77 g (4.0 mmol) EDC·HCl, 0.20 g (1.6 mmol) DMAP, and 7.6 mL anhydrous DCM. The contents of the second vial were then transferred to the flask containing 7. After stirring at 0° C. for 3 hours, the mixture was washed with 0.5% NaHCO$_3$ (2×50 mL), water (50 mL), 0.1 N HCl (2×50 mL) and brine. The organic solution was dried with MgSO$_4$, and evaporated under vacuum to afford 1.05 g crude 20-(Boc-GABA)-10-TBDPS-SN38 (9) (1.28 mmol, quantitative yield).

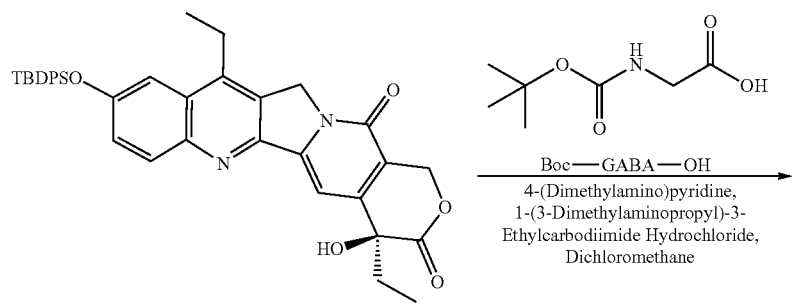

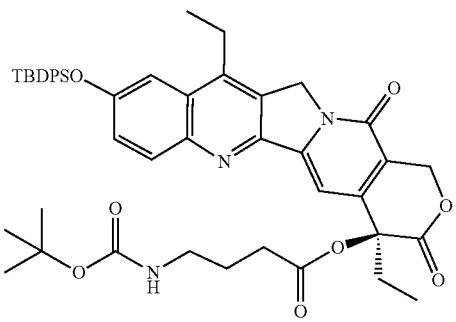

Example 10. Synthesis of 20-(Boc-Hex)-10-TBDPS-SN38 (Compound 10)

To a 40 mL vial with 0.6 g (0.95 mmol) 10-TBDPS-SN38 (7) was added 10.4 mL anhydrous DCM and a magnetic stir bar. Following solvent addition, the reaction was cooled to 0° C. To a separate vial was added 0.55 g Boc-Hex-OH (2.4 mmol), 0.45 g (2.4 mmol) EDC·HCl, 0.12 g (0.98 mmol) DMAP, and 4.5 mL anhydrous DCM. The contents of the second vial were then transferred to the flask containing 7. After stirring at 0° C. for 3 hours, the mixture was washed with 0.5% NaHCO$_3$ (2×50 mL), water (50 mL), 0.1 N HCl (2×50 mL) and brine. The organic solution was dried with MgSO$_4$, and evaporated under vacuum to afford 0.88 g crude 20-(Boc-Hex)-10-TBDPS-SN38 (10) (1.0 mmol, 111% yield).

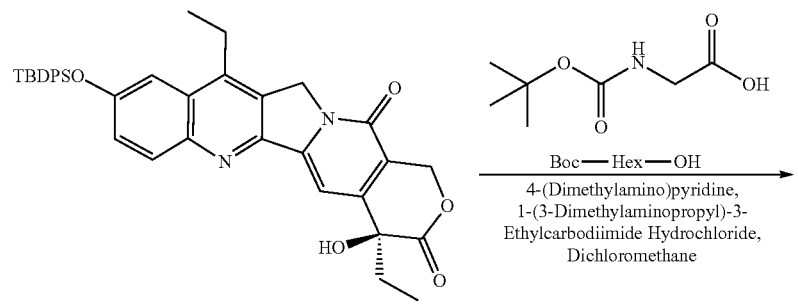

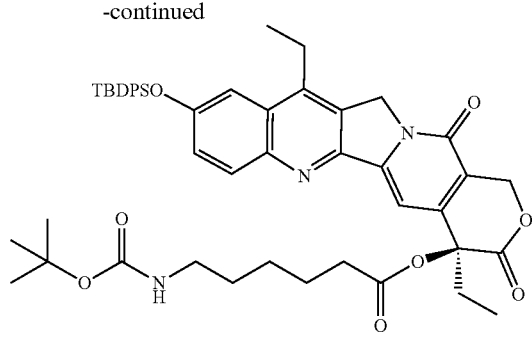

10

Example 11. Synthesis of 20-(Boc-Val)-10-TBDPS-SN38 (Compound 11)

To a 100 mL round bottom flask with 1.0 g (1.6 mmol) 10-TBDPS-SN38 (7) was added 17.7 mL anhydrous DCM and a magnetic stir bar. Following solvent addition, the reaction was cooled to 0° C. To a separate vial was added 0.87 g Boc-Val-OH (4.0 mmol), 0.77 g (4.0 mmol) EDC·HCl, 0.20 g (1.6 mmol) DMAP, and 7.6 mL anhydrous DCM. The contents of the second vial were then transferred to the flask containing 7. After stirring at 0° C. for 3 hours, the mixture was washed with 0.5% NaHCO₃ (2×50 mL), water (50 mL), 0.1 N HCl (2×50 mL) and brine. The organic solution was dried with MgSO₄, and evaporated under vacuum to afford 1.24 g crude 20-(Boc-Val)-10-TBDPS-SN38 (11) (1.5 mmol, 93% yield).

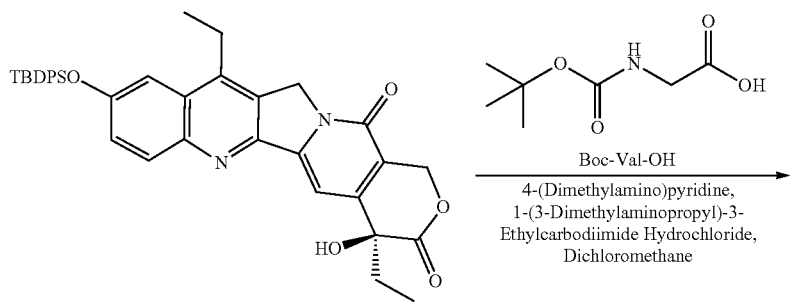

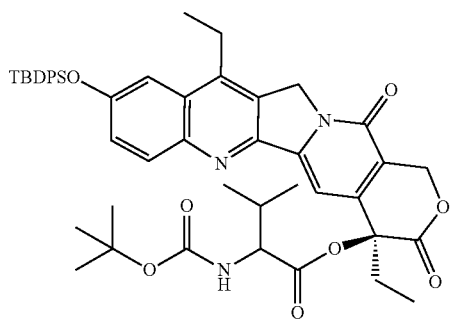

11

Example 12. Synthesis of 20-(HCl·Gly)-SN38 (Compound 12)

To a 100 mL round bottom flask with 1.2 g (1.5 mmol) 20-(Boc-Gly)-10-TBDPS-SN38 (8) and magnetic stir bar, 75 mL of 12 N HCl was added slowly under constant stirring. Atop the HCl solution was added hexane (20 mL). After stirring at room temperature overnight (~16 hours), the hexane layer was removed from the reaction. The reaction was then washed with hexane in triplicate (3×20 mL). HCl was then removed from the reaction mixture using vacuum. The residue was dissolved in MeOH, and precipitated with MTBE. The solids were dried under vacuum to afford 0.44 g (0.91 mmol, 60% yield) of 20-(HCl·Gly)-SN38 (12).

tated with MTBE. The solids were dried under vacuum to afford 0.16 g (0.27 mmol, 60% yield) of 20-(TFA·GABA)-SN38 (13).

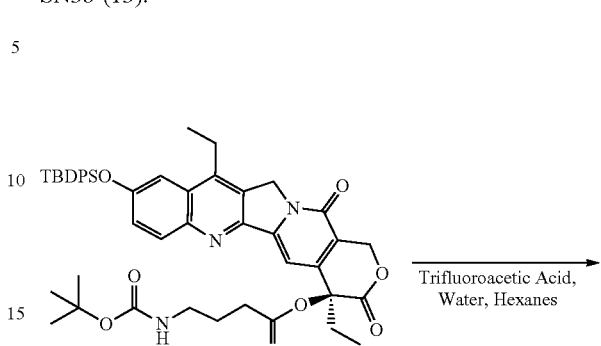

9

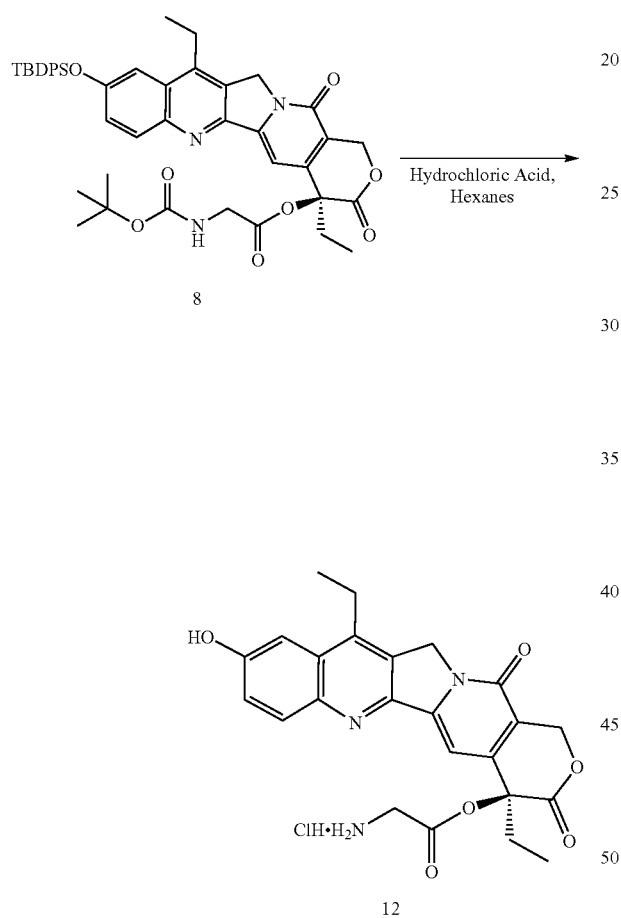

8

12

Example 13. Synthesis of 20-(TFA·GABA)-SN38 (Compound 13)

To a 50 mL round bottom flask with 0.37 g (0.45 mmol) 20-(Boc-GABA)-10-TBDPS-SN38 (9), 8.6 mL water, and a magnetic stir bar, 8.6 mL of TFA was added slowly under constant stirring. Atop the TFA solution was added hexanes (20 mL). After stirring at room temperature overnight (~16 hours), the hexane layer was removed from the reaction. The reaction was then washed with hexanes in triplicate (3×20 mL). The reaction mixture was then concentrated using vacuum. The residue was dissolved in MeOH, and precipi-

13

Example 14. Synthesis of 20-(TFA·Hex)-SN38 (Compound 14)

To a 50 mL round bottom flask with 0.37 g (0.43 mmol) 20-(Boc-Hex)-10-TBDPS-SN38 (10), 8.3 mL water, and a magnetic stir bar, 8.3 mL of TFA was added slowly under constant stirring. Atop the TFA solution was added hexanes (20 mL). After stirring at room temperature overnight (~16 hours), the hexane layer was removed from the reaction. The reaction was then washed with hexanes in triplicate (3×20 mL). The reaction mixture was then concentrated using vacuum. The residue was dissolved in MeOH, and precipitated with MTBE. The solids were dried under vacuum to afford 0.16 g (0.26 mmol, 60% yield) of 20-(TFA·Hex)-SN38 (14).

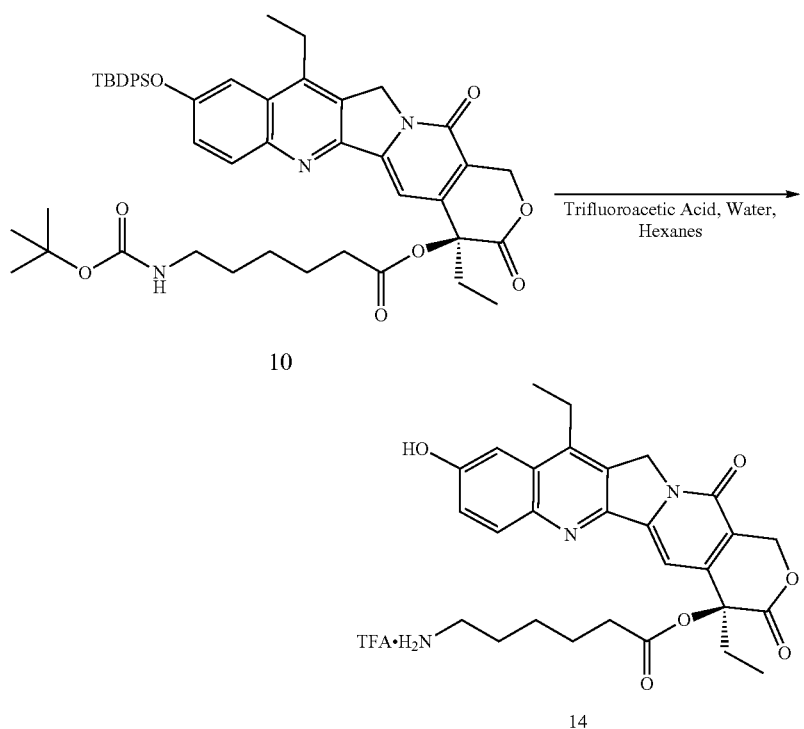

10

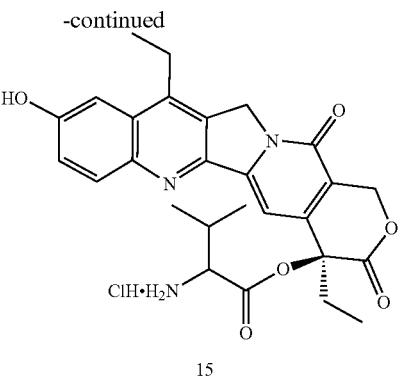

14

Example 15. Synthesis of 20-(HCl·Val)-SN38 (Compound 15)

To a 100 mL round bottom flask with 1.2 g (1.4 mmol) 20-(Boc-Val)-10-TBDPS-SN38 (11) and a magnetic stir bar, 75 mL of 12 N HCl was added slowly under constant stirring. Atop the HCl solution was added hexane (20 mL). After stirring at room temperature overnight (~16 hours), the hexane layer was removed from the reaction. The reaction was then washed with hexane in triplicate (3×20 mL). HCl was then removed from the reaction mixture using vacuum. The residue was dissolved in MeOH, and precipitated with MTBE. The solids were dried under vacuum to afford 0.46 g (0.86 mmol, 60% yield) of 20-(HCl·Val)-SN38 (15).

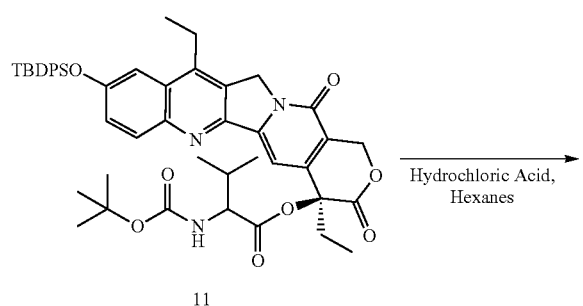

11

-continued

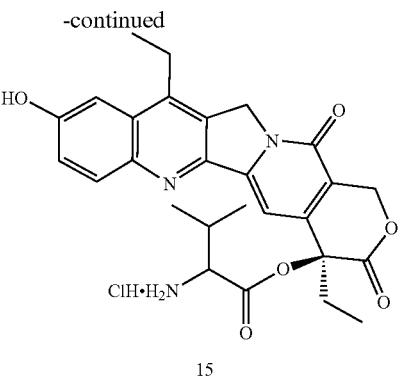

15

Example 16. Synthesis of MAP-Gly-SN38 (Compound 16)

A 10 mL round bottom flask with 100 mg MAP (6) and a magnetic stir bar was charged with 8 mL of anhydrous DMSO. To the reaction mixture was then added 51.9 mg (0.27 mmol) EDC·HCl and 24.9 mg (0.22 mmol) N-hydroxysuccinimide (NHS). Following the addition of EDC·HCl and NHS, to the reaction mixture was added 105.2 mg (0.22 mmol) 20-(HCl·Gly)-SN38 (12) and anhydrous DIPEA (0.22 mmol). The mixture was stirred overnight (~18 hours) at room temperature. The reaction mixture was dialyzed against DMSO, and then against pH 4 water using a 10 kDa membrane. The dialyzed product was then passed through a 0.22 μm filter, frozen, and lyophilized to afford 98 mg (quantitative yield) of MAP-Gly-SN38 (16).

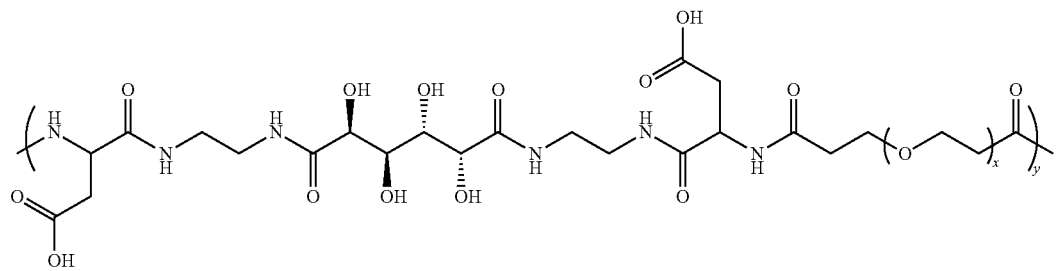

6

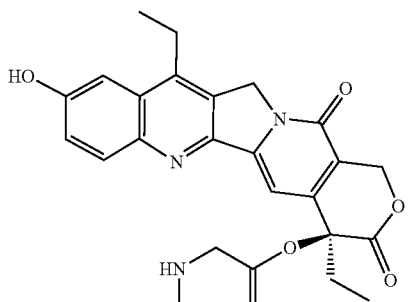

1-(3-Dimethylaminopropyl)-3-
Ethylcarbodiimide Hydrochloride,
N-Hydroxysuccinimide,
Diisopropylethylamine, Dimethyl Sulfoxide

12

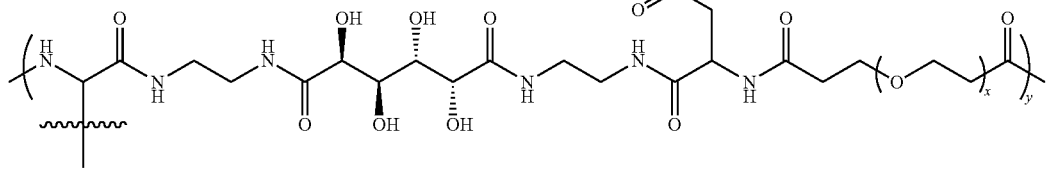

16

As stated in Example 5, x was about 80 and y was about 16 for Compounds 6 and 16.

Example 17. Synthesis of MAP-GABA-SN38 (Compound 17)

A 10 mL round bottom flask with 100 mg MAP (6) and a magnetic stir bar was charged with 8 mL of anhydrous DMSO. To the reaction mixture was then added 51.9 mg (0.27 mmol) EDC·HCl and 24.9 mg (0.22 mmol) NHS. Following the addition of EDC·HCl and NHS, to the reaction mixture was added 128.3 mg (0.22 mmol) 20-(TFA·GABA)-SN38 (13) and anhydrous DIPEA (0.22 mmol). The mixture was stirred overnight (~18 hours) at room temperature. The reaction mixture was dialyzed against DMSO, and then against pH 4 water using a 10 kDa membrane. The dialyzed product was then passed through a 0.22 μm filter, frozen, and lyophilized to afford 91 mg (quantitative yield) of MAP-GABA-SN38 (17).

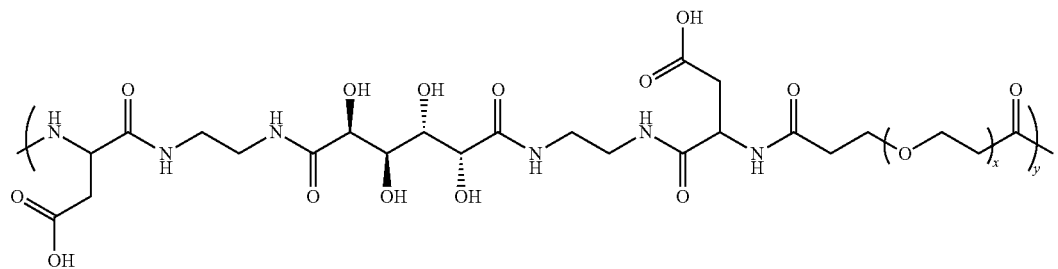

6

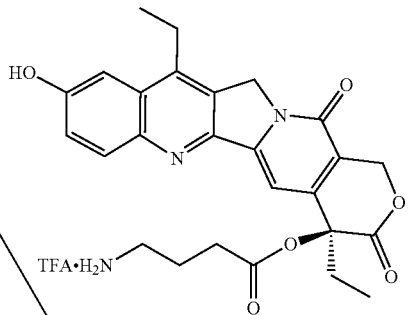

1-(3-Dimethylaminopropyl)-3-
Ethylcarbodiimide Hydrochloride,
N-Hydroxysuccinimide,
Diisopropylethylamine, Dimethyl Sulfoxide

13

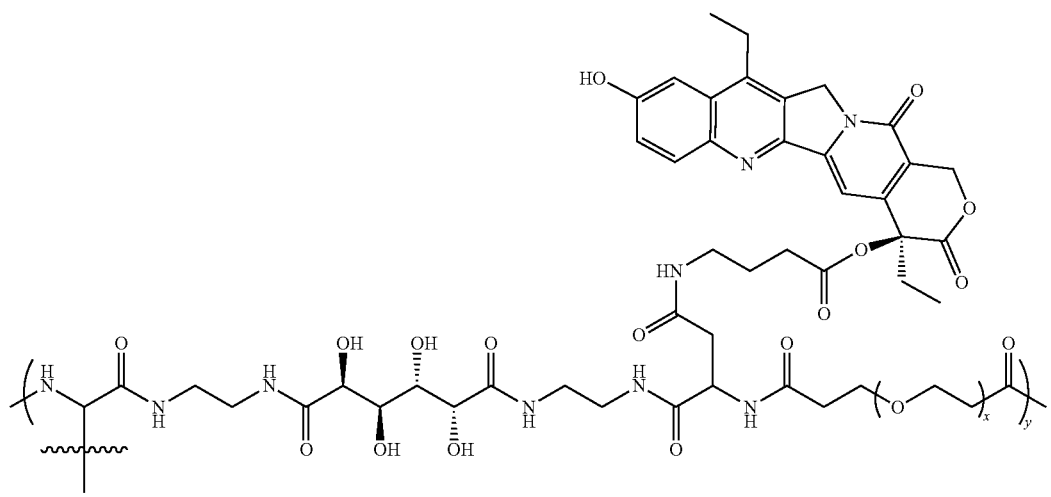

17

As stated in Example 5, x was about 80 and y was about 16 for Compounds 6 and 17.

Example 18. Synthesis of MAP-Hex-SN38 (Compound 18)

A 10 mL round bottom flask with 100 mg MAP (6) and a magnetic stir bar was charged with 8 mL of anhydrous DMSO. To the reaction mixture was then added 51.9 mg (0.27 mmol) EDC·HCl and 24.9 mg (0.22 mmol) NHS. Following the addition of EDC·HCl and NHS, to the reaction mixture was added 134.4 mg (0.22 mmol) 20-(TFA·Hex)-SN38 (14) and anhydrous DIPEA (0.22 mmol). The mixture was stirred overnight (~18 hours) at room temperature. The reaction mixture was dialyzed against DMSO, and then against pH 4 water using a 10 kDa membrane. The dialyzed product was then passed through a 0.22 μm filter, frozen, and lyophilized to afford 97 mg (quantitative yield) of MAP-Hex-SN38 (18).

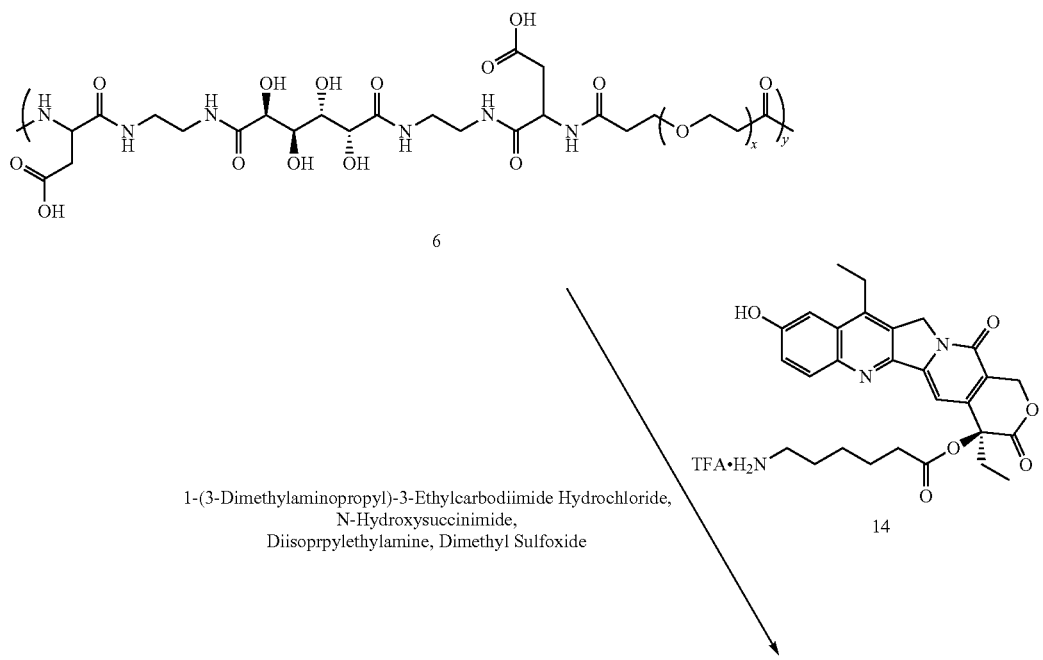

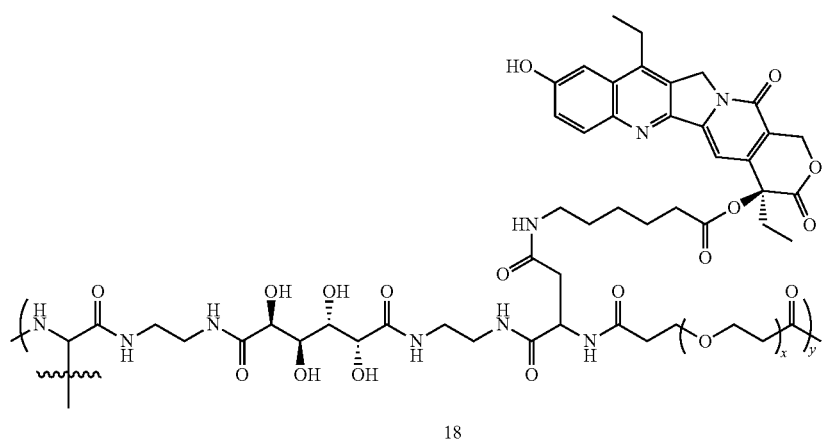

As stated in Example 5, x was about 80 and y was about 16 for Compounds 6 and 18.

Example 19. Synthesis of MAP-Val-SN38 (Compound 19)

A 10 mL round bottom flask with 100 mg MAP (6) and a magnetic stir bar was charged with 8 mL of anhydrous DMSO. To the reaction mixture was then added 51.9 mg (0.27 mmol) EDC·HCl and 24.9 mg (0.22 mmol) NHS. Following the addition of EDC·HCl and NHS, to the reaction mixture was added 114.3 mg (0.22 mmol) 20-(HCl·Val)-SN38 (15) and anhydrous DIPEA (0.22 mmol). The mixture was stirred overnight (~18 hours) at room temperature. The reaction mixture was dialyzed against DMSO, and then against pH 4 water using a 10 kDa membrane. The dialyzed product was then passed through a 0.22 μm filter, frozen, and lyophilized to afford 96 mg (quantitative yield) of MAP-Val-SN38 (19).

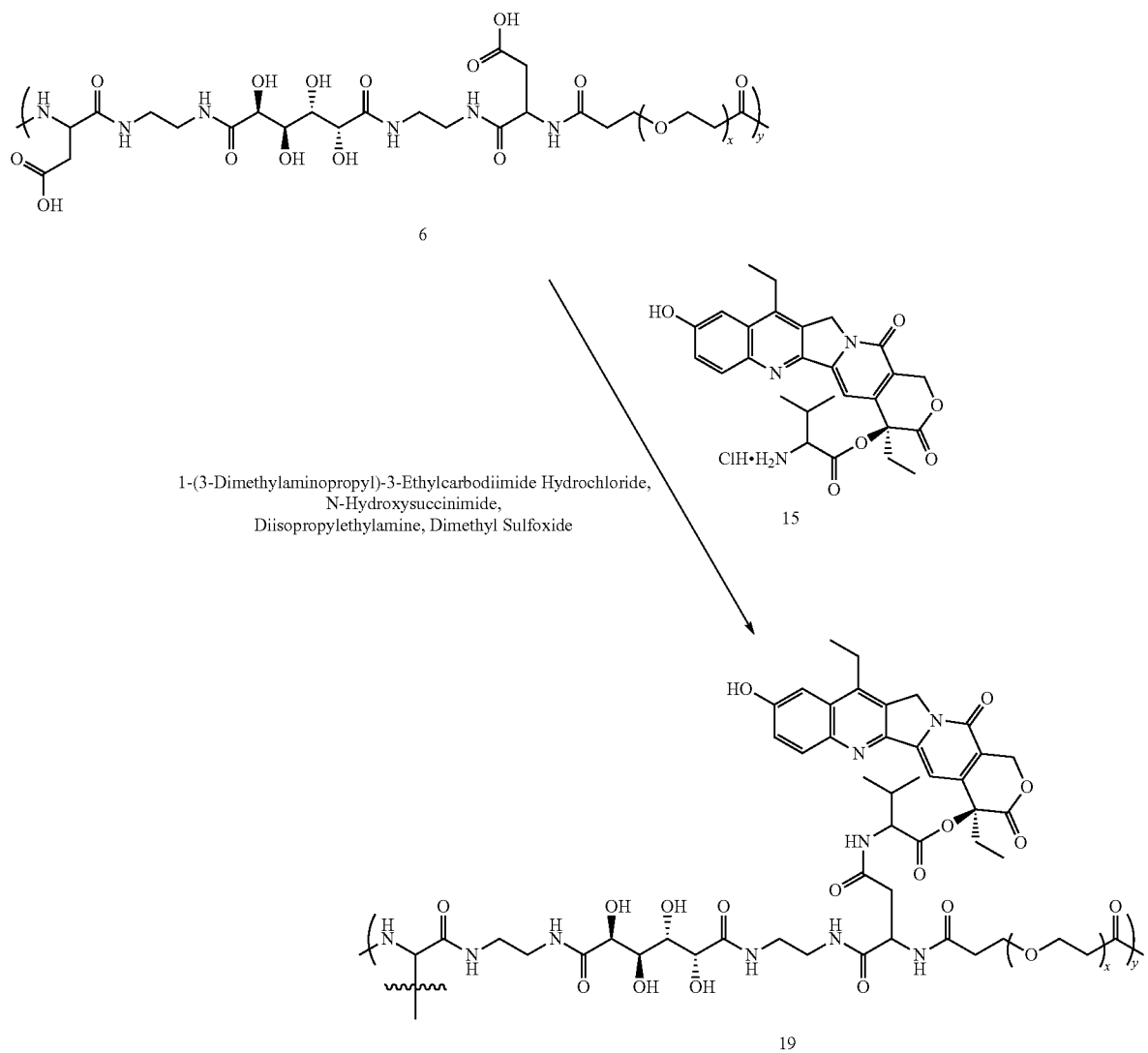

As stated in Example 5, x was about 80 and y was about 16 for Compounds 6 and 19.

Example 20. Characterization of Drug Loading

Loading of SN38 onto the MAP was determined on an Agilent 1100 HPLC system with a reverse phase column (Synergi 4 m Hydro-RP 80 Å, Phenomenex) connected to a fluorescence detector set to 375/536 nm (ex/em). ACN/10 mM potassium phosphate buffer, pH 4 (1:1 v/v) was used as the eluent at a flow rate of 0.5 mL/min.

For analysis, polymer drug conjugates (Compounds 16-19) were dissolved to a concentration of 1 mg/mL in PBS, pH 7.4. The amount of unconjugated SN38 was determined by first mixing 10 μL of sample with 10 μL of 0.1 N HCl and incubating at room temperature for 30 min. 6.7 μL of water, followed by 73.3 μL ACN was then added and the mixture incubated at room temperature for 3 h. This mixture was centrifuged at 14,000 g for 10 min at 4° C., and the supernatant was then passed through a 0.45 μm filter. SN38 concentration was determined by injecting 10 μL of filtered sample. The resulting peak area of the eluted SN38 was compared to that of known concentrations of SN38.

To measure the total amount of SN38, 10 μL of sample was mixed with 6.7 μL of 0.1 N NaOH. This solution was incubated at room temperature for 3.5 h to allow SN38 to be released from parent polymer. 10 μL of 0.1 N HCl was then added (to convert the carboxylate SN38 form to the lactone form) and the mixture was incubated for 45 min. 73.3 μL of ACN was subsequently added and the mixture incubated for 3 h at room temperature. The sample was then centrifuged and processed as above. Polymer-bound SN38 was determined from the difference between total SN38 and unconjugated SN38 concentrations.

Example 21. Formation of MAP-Linker-SN38 Nanoparticles

Polymer drug conjugates (Compounds 16-19) were dissolved to a concentration of 4 mg/mL in pH 4 water to form MAP-linker-SN38 nanoparticles. The solutions were then passed through a 0.22 μm filter and frozen for subsequent analyses. Nanoparticles were diluted to 2 mg/mL in pH 4 water, and hydrodynamic diameter was measured by dynamic light scattering (DLS) using a ZetaPALS (Brookhaven Instruments Corporation) instrument. Five runs of 1 min each were performed for the nanoparticles. All nanoparticles had diameters near 25 nm, varying from 19 to 32 nm.

Example 22. In Vitro Release Studies

Experiments were conducted to assess the release of SN38 from MAP-Gly-SN38, MAP-GABA-SN38, MAP-Hex-SN38, MAP-Val-SN38, MAP-Ala-SN38, MAP-3-Ala-SN38 and MAP-Leu-SN38 nanoparticles. See examples 33-35 below for synthesis of MAP-Ala-SN38, MAP-β-Ala-SN38 and MAP-Leu-SN38 nanoparticles. These studies were conducted at 0.1 mg SN38/mL in PBS at pH values of 6.5, 7.0, or 7.4.

PBS media were pipetted into cuvettes which were incubated at 37° C. in a humidified oven for 2 h for equilibration. Nanoparticle formulations were mixed into the relevant medium and placed back into the oven. Samples were taken out at predetermined time points and immediately frozen at −80° C. until time for analysis. The amount of unconjugated SN38 and the total amount of SN38 were determined as described supra in Example 20. Polymer-bound SN38 concentration was determined from the difference between total SN38 and unconjugated SN38 concentrations.

The results indicated that release of SN38 exhibited first-order kinetics from all seven of the nanoparticles: MAP-Gly-SN38, MAP-GABA-SN38, MAP-Hex-SN38, MAP-Val-SN38, MAP-Ala-SN38, MAP-β-Ala-SN38 and MAP-Leu-SN38. A strong dependence of release rate with pH was observed. As the pH increased from 6.5 to 7.4, the release half-lives decreased for all nanoparticle formulations, indicating that hydrolysis plays an important role in the release of SN38. Longer half-lives for the nanoparticles with increasingly hydrophobic and sterically hindered linkers were observed, varying from ~30 to >168 h.

Example 23. Determination of Number of Strands Per Particle

The number of strands per nanoparticle (SpP) was determined by calculating the ratio between the molecular weight of the particle and the molecular weight of the MAP. Polyethylene oxide (PEO) standards with nominal molecular weights of 100 kDa and 200 kDa, and samples of interest, were prepared for GPC analysis (Omnisec GPC, Malvern) by dissolving to a concentration of 1-5 mg/mL in pH 3 water or PBS+0.02% sodium azide. Concentrations were chosen to be similar to those expected after particle formation. Once dissolved, samples were passed through a 0.45 μm filter and analyzed on a Zenix SEC 300 or Zenix-C SEC 300 column (Sepax, 3 μm) at 0.35 mL/min at 30° C. Light scattering and Differential Refractive Index information were used with Malvern OMNISEC software, or similar molecular weight analysis software, to determine molecular weight of the particles.

The molecular weight of the particles was divided by the molecular weight of the MAP-SN38 conjugate molecule to determine the Strands per Particle. The molecular weight of the MAP-SN38 conjugate molecule was calculated from the molecular weight of the polymer adjusted with the percent drug loading, according to the equation:

$$MW_{conjugate} = MW_{polymer}/(1-T\%)$$

in which $MW_{polymer}$ is the molecular weight of the MAP, and T % is the percent loading of therapeutic agent expressed as a decimal, e.g. 10% loading results in T %=0.1.

The determination of SpP was demonstrated with MAPs with varying linkers and drugs. MAPs of the same molecular weight conjugated to CPT or SN38 produce nanoparticles with ~1.5-2.5 strands per particle. The use of different linkers on the derivatized SN38 alters the number of strands per particle and, therefore, the density of the resultant particles. The number of strands per particle varied from ~1.3-~4.6, depending on the linker (glycine, gamma-amino butyric acid, hexanoic acid, alanine, β-alanine, leucine or valine).

Example 24. Preparative Scale Synthesis of N-Boc-Protected Mucic Acid Diamine (Compound 2)

To a mechanically stirred 15 liter reaction vessel under nitrogen was added 450 g (2.1 mol) mucic acid and MeOH (5.75 L). To this reaction vessel was added a solution consisting of MeOH (1 L) and concentrated sulfuric acid (34.2 mL, 0.64 mol). The mixture was heated to an internal temperature of 65° C. for 48 hours. The contents of the reaction vessel were cooled to 22° C. at which point 0.81 L (5.78 mol) TEA was added over 20 minutes. The reaction was stirred for 1 hour at which point a solution of 0.76 kg (4.71 mol) N-(2-aminoethyl)(tert-butoxy)carboxamide in 0.9 L MeOH was added over 20 minutes. The reaction was heated to an internal temperature of 63° C. and after 60 minutes 1.8 L of MeOH was added to facilitate stirring. After a total of 2 hours at 63° C., the reaction vessel was cooled at 1° C. per minute and held overnight at 20° C. The reaction slurry was filtered, and the cake was washed with MeOH (3×0.5 L). The solids were left drying overnight on the vacuum filter to ensure full removal of liquids. Isolated solids were charged back into the reaction vessel with MeOH (9.0 L) and stirred at 63° C. for 1 hour. The reaction vessel was set to cool at a rate of 1° C. per minute and held at 20° C. for approximately 60 hours. The slurry was filtered and washed with MeOH (2×1.0 L) and solids were dried overnight in a vacuum oven at 45° C. to afford 963 g (91% yield as a solvate with MeOH, 82% yield anhydrous) of N-Boc-protected mucic acid diamine (2).

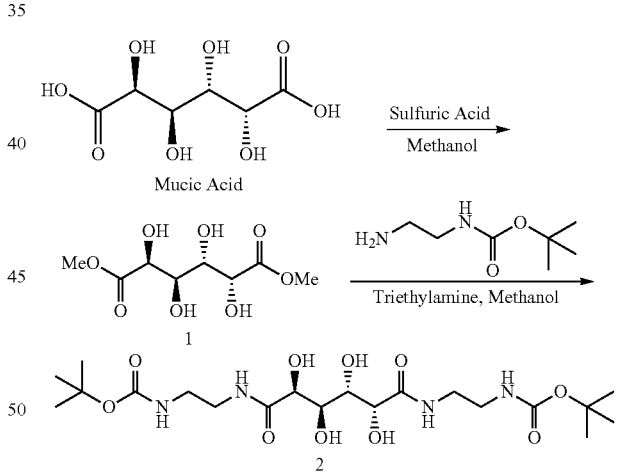

Example 25. Preparative Scale Synthesis of Mucic Acid Diaminochloride (Compound 3)

To a mechanically stirred 15 L reaction vessel was added 890 g of N-Boc-protected mucic acid diamine (2) (1.80 mmol), 3.6 L water, and 7.1 L MeOH. To this slurry was added 12 M HCl (3.6 L) over a period of 2 hours while maintaining a temperature in a range of from 20° C. to 30° C. The reaction was allowed to stir overnight at which point the slurry was filtered and washed with 1.8 L MeOH. Isolated solids were dried in trays at 45° C. in a vacuum oven. The isolated solids were charged into a 15 L reaction vessel under nitrogen along with water (5.5 L), and stirred at 45° C. 5.5 L of MeOH was added over 30 minutes resulting in crystallization. The reaction vessel was chilled to allow the reaction contents to cool to room temperature. Solids were isolated by filtration and washed with MeOH (2×1.0 L). Solids were collected and dried in a vacuum oven at 40° C. overnight to afford 504 g (1.37 mol, 76% yield) of mucic acid diaminochloride (3).

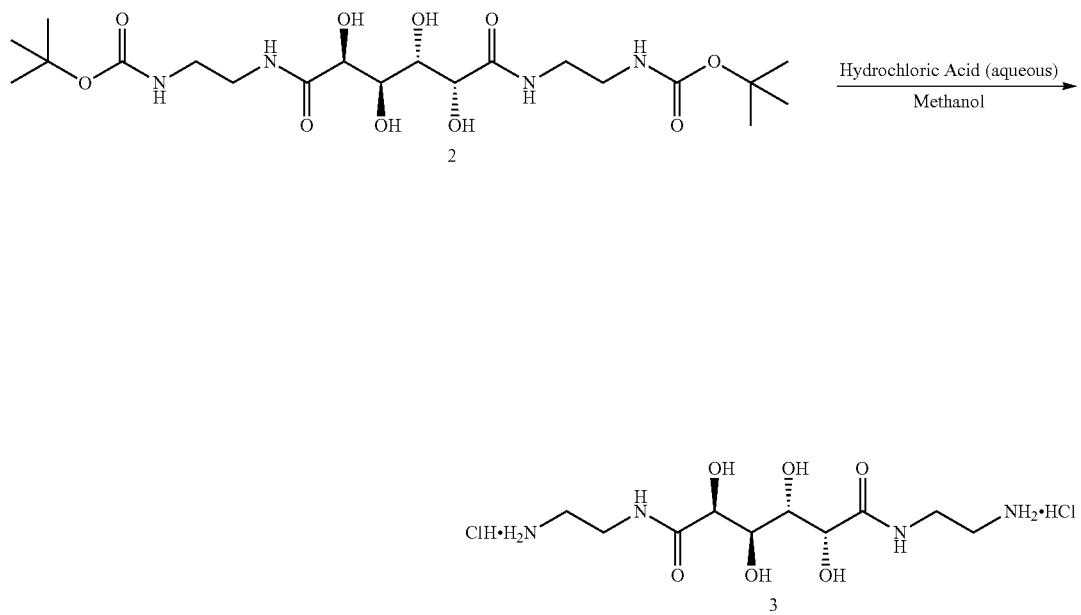

Example 26. Preparative Scale Synthesis of Mucic Acid di(Asp(OtBu)-Boc) (Compound 4)

To a 15 L, mechanically stirred reactor was added 1.27 kg Boc-L-aspartic acid 4-tert-butyl ester (4.39 mol), 0.62 kg Oxyma (ethyl cyanohydroxyiminoacetate) (4.39 mol), and 3.5 L DCM. The reaction mixture was cooled to 5° C. and stirred for 30 minutes. To the reaction mixture was added 0.84 kg EDC·HCl (4.40 mol) as a solid over the course of 10 minutes. The EDC·HCl was rinsed into the reaction with an additional 0.5 L DCM and the reaction was allowed to stir for about 30 minutes and was then chilled to 10° C. A separate 12 L flask was charged with 1.02 kg sodium carbonate (9.61 mol) and 5.0 L water. The components were allowed to dissolve and then cool to room temperature. Over the course of 10 minutes, 504 g (1.37 mol) of 3 was added to the sodium carbonate solution. This mixture was allowed to stir for 15 minutes at which point it was added to the Boc-L-aspartic acid 4-tert-butyl ester in the 15 L reaction flask, over the course of about 3 minutes. The mixed reaction exothermed but a cooling jacket was set to 10° C. for 30 minutes and subsequently to 15° C. for another 45 minutes. The reaction jacket was then set to 33° C. for 1 hour after which was added 8.06 L of water, under stirring for 5 minutes. Stirring was then discontinued and the phases of the reaction separated after 15 minutes. The DCM (bottom layer) was removed and to the reactor was then added an additional 1.0 L DCM. This mixture was then stirred for 10 minutes and then allowed to settle. The DCM layer was collected and combined with the initially collected organic layer, and concentrated to a total volume of about 3 L. 1 L of water was added to the organic mixture to help further distill off the DCM. The organic reaction mixture was then added to a 15 L reactor containing 11.1 L water heated to 40° C. The stirring mixture was returned to 20° C. and a slurry formed. Water was removed and solids remained in the reactor. To the wet solids was added 10.1 L of water. The reaction mixture was heated to 37° C. to facilitate stirring. The reaction was then cooled to 3° C. overnight and allowed to stir. Solids were filtered and then charged back into the reactor with an additional 10 L of water. The slurry was allowed to stir at room temperature for 3 hours. Solids were filtered again, washed with 1.0 L of water, and allowed to dry to afford 815 g of material. 790 grams of crude 4 were added to a 5 L round bottom flask along with 2.4 L of ACN and heated to 60° C. Water was continuously distilled off through azeotropic distillation under partial vacuum and the continued addition of ACN, to a volume of about 1.6 L. To this was added 3.1 L of ACN to induce crystallization. The slurry was heated back to reflux briefly and then cooled to 5° C. and kept there for 30 minutes. Following cooling, the slurry was filtered and washed with ACN (4×0.5 L, 5° C.). The solids were heated to 50° C. under vacuum to remove solvent. 6.3 L of DCM was added in two portions to the reaction mixture at which point the slurry was concentrated to distill off ACN. Solids were then heated to 80° C. under vacuum to remove DCM and afford a free flowing powder. Solids were then placed in a vacuum oven to dry at 80° C. under reduced pressure to afford 310 g (0.35 mol, 26% yield) of mucic acid di(Asp(OtBu)-Boc) (4) as a 1:1 molar solvate with ACN.

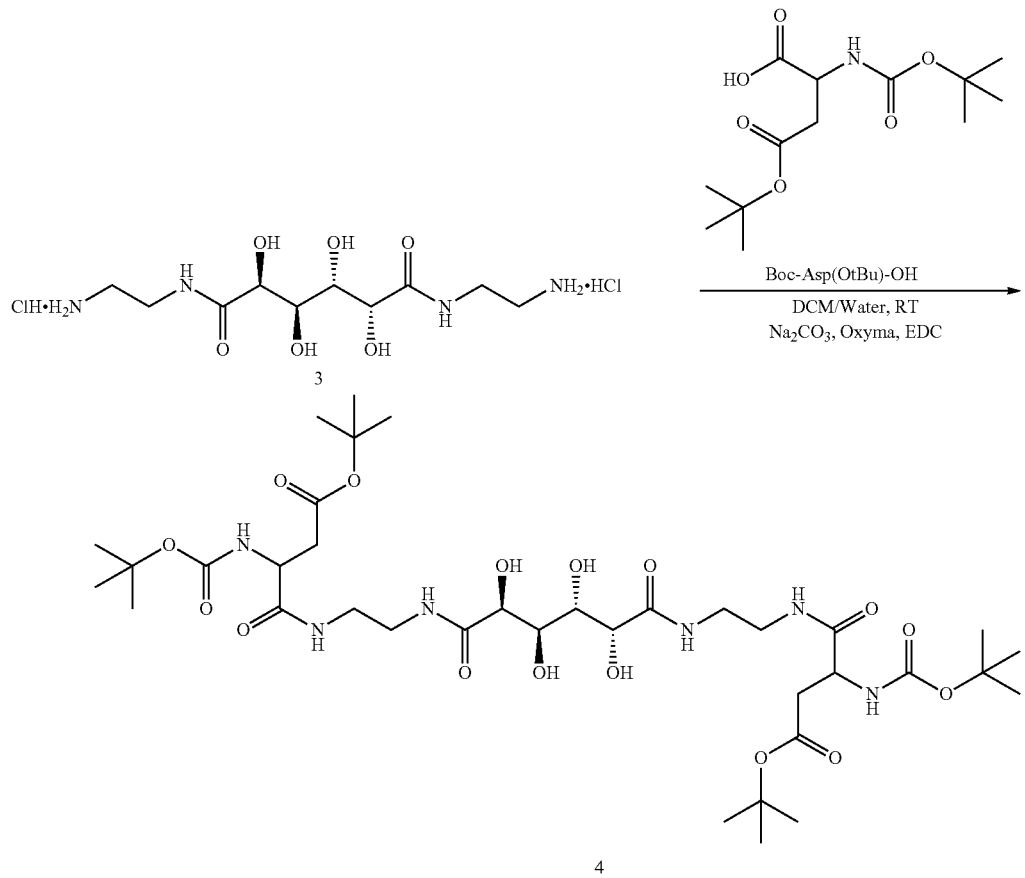

Example 27. Preparative Scale Synthesis of Mucic Acid Monomer Neutral Species (Compound 20)

A 5 L jacketed round bottom flask equipped with mechanical stirring was charged with 300 g of 4 (0.34 mol), 1.2 L of DCM, 0.11 L of water (6.13 mol), and 0.279 L of triisopropylsilane (1.36 mol). The reaction mixture was cooled to 5° C. and subsequently formed a slurry. 1.2 L of TFA, which had previously been cooled in an ice bath over the course of 1 hour, was added to this stirred slurry. The reaction was held at an internal temperature of 4° C. overnight. An additional 0.30 L of TFA was added and stirring continued at 4° C. overnight. The reaction was stirred at 5° C. for 10 minutes upon the addition of 0.90 L of hexanes. The reaction mixture was then poured into a separatory funnel and the bottom phase was separated into a 5 L round bottom funnel. The reaction material was rinsed with additional DCM (300 mL), which was combined with the initially collected fraction. The combined collected fractions were concentrated on a rotary evaporator below 30° C. An additional 0.90 L of DCM was added to the flask and subsequently removed at 25° C. using a rotary evaporator. 0.60 L of toluene was then added and concentrated on a rotary evaporator to azeotrope off water and TFA, resulting in an oil. The oil was filtered through a plug of celite and washed four times with DCM (0.40 L). The DCM was removed by the rotary evaporator at 35° C. The resulting biphasic mixture was added to a clean 5 L reaction vessel and heated to 23° C. 3.0 L of cyclopentyl methyl ether (CPME) was added over the course of 20 minutes resulting in the formation of an oily solid. The vessel was cooled to 22° C. and stirred overnight to afford sticky crystals. A short path distillation column was used to distill off 1.5 L of DCM at 35° C. The resulting slurry was filtered and washed with CPME (2×0.45 L). Solids were then dried in a round bottom flask on a rotary evaporator and then dried on vacuum overnight at room temperature to afford 261 g of mucic acid monomer neutral species (208.8 g, 82% yield accounting for potency).

To further recrystallize, 0.24 kg of mucic acid monomer neutral species was added to a 1 L Erlenmeyer flask along with water (0.20 L). The mixture was stirred at room temperature for 1 hour to afford a solution. This solution was filtered through a filter funnel into a 5 L round bottom flask with the aid of additional water (50 mL). 2.2 L of tetrahydrofuran (THF) was added to the flask under stirring, over the course of 30 minutes. The mixture was allowed to stir for a total of 60 minutes at which point it was concentrated at 35° C. on a rotary evaporator to remove 1 L of distillate. Over 10 minutes additional THF (0.98 L) was added. The slurry was cooled to room temperature and allowed to stir for 20 minutes. The cooled slurry was filtered and washed with THF (2×0.25 L), and subsequently dried in a vacuum oven at room temperature for 2.5 days to afford 119 g (0.23 mol, 66% yield) of mucic acid monomer in the neutral form (20).

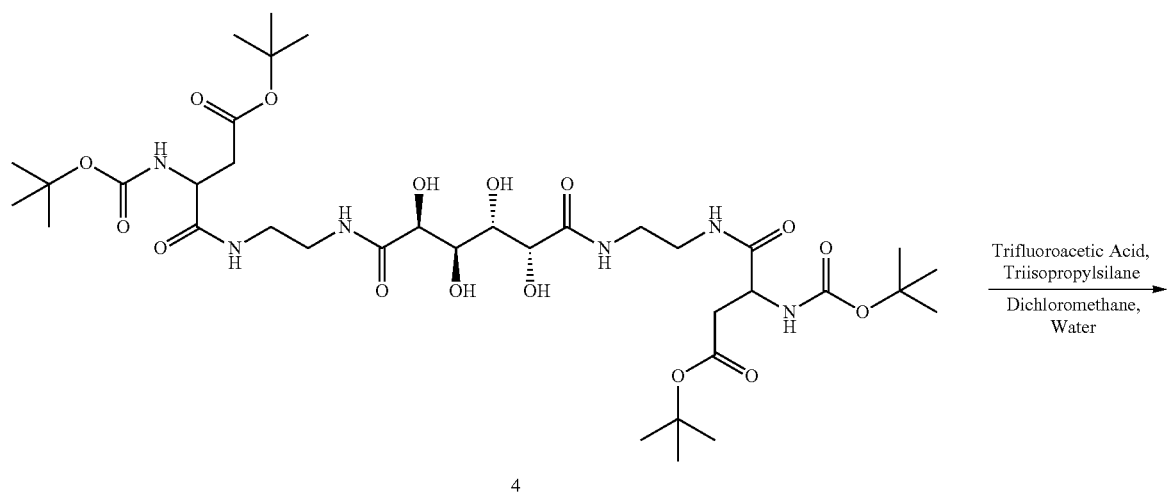

4

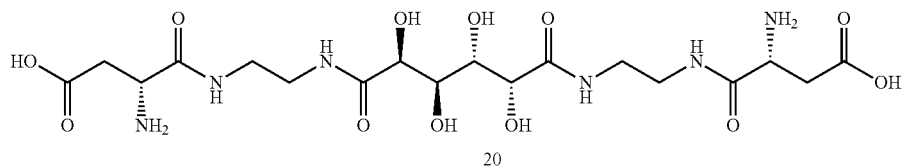

20

Example 28. Preparative Scale Synthesis of MAM (Compound 5)

A 3 L round bottom flask charged with 120 g (0.23 mol) of 20 and DCM (1.2 L) was stirred for 10 minutes at which point water (0.06 L) was added. Stirring continued for 15 minutes at which point TFA (66.0 mL, 0.86 mol) was added over 5 minutes. Solids dissolved and the mixture was allowed to stir for 1 hour at room temperature. The mixture was concentrated on a rotary evaporator at 30° C. To a 5 L round bottom flask equipped with mechanical stirring was added ether (4.0 L) as well as MAM seed crystals (5, 12 g). The 20/TFA/water solution was slowly added to ether under stirring. After 1 hour, the ether was decanted off, and fresh additional ether was added (3.6 L). The mixture was stirred at room temperature until the MAM-diTFA salt precipitated. Solids were filtered and washed once with ether (0.2 L). Solids were dried at room temperature under vacuum and then heated for 1 hour at 30° C. to afford 122 g (75% yield) of MAM (5).

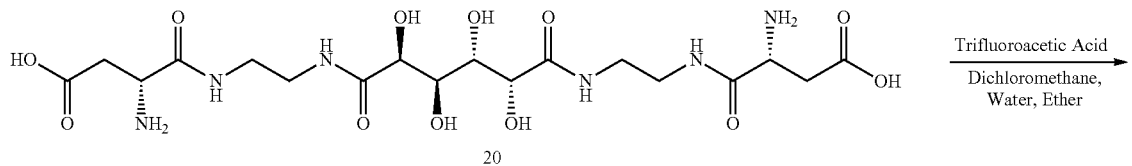

20

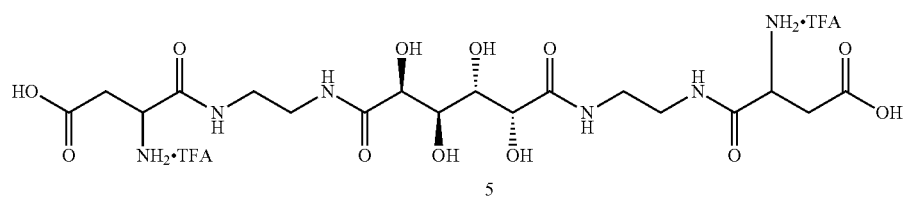

5

Example 29. Preparative Scale Synthesis of Mucic Acid Polymer (Compound 6)

MAP (6) was synthesized by a step-growth polymerization between mucic acid monomer (MAM) (5) and diSPA-PEG$_{3.5k}$.

A 20 mL glass vial with 108.52 mg (0.158 mmol) of MAM (5) containing ~1.5 equivalents TFA, 579.54 mg of diSPA-PEG$_{3.5k}$ (0.157 mmol) and magnetic stir bar was sealed, and the two solids were dried under vacuum at room temperature for 1 hour. To the reaction flask was added 3.43 mL of anhydrous DMSO under argon. Reactants were solubilized at room temperature. Following solubilization, to the reaction mixture was added 126 µL of anhydrous DIPEA (0.72 mmol) under argon. The reaction mixture was stirred at room temperature under constant magnetic stirring for 3 hours.

The reaction mixture was precipitated in cold isopropyl alcohol (IPA, ×10 volume, 0-4° C.). The reactor was washed with DMSO (3×1 mL), followed by the precipitation in cold IPA. The white suspension obtained was stirred for 30 minutes at 0-4° C. and centrifuged for 12 minutes at 4° C. The white fluffy polymer settled at the bottom was isolated by decanting the IPA. The polymer was washed twice with cold IPA (×5 volume) and the procedure was repeated. The product was dried under vacuum overnight on Schlenk line at room temperature to remove the IPA and then dissolved in milli-Q water (8 mL). The solution in water was frozen and lyophilized to afford 612.5 mg (quantitative yield) of MAP (6).

Molecular weight of the polymer was controlled by incorporating a stoichiometric skew between the two monomers. At 1:1, the MAP (6) molecular weight was greatest, and as the molar ratio departed from 1:1 the molecular weight decreased. Exemplary stoichiometric skews and experimental molecular weights, obtained by GPC, are shown in Table 1.

TABLE 1

Stoichiometric Skews for Controlled MAP (6) Synthesis

| MAM:diSPA-PEG$_{3.5k}$ Ratio | Molecular Weight (kDa) |
| --- | --- |
| 1.01 | 77.49 |
| 1.04 | 62.44 |
| 1.10 | 55.87 |

Example 30. Synthesis of 20-(Boc-Gly)-CPT (Compound 21)

200.4 mg (0.58 mmol) of CPT, 302.7 mg (1.73 mmol) of Boc-Gly-OH, and 140.6 mg (1.15 mmol) of DMAP were added to a 10 mL round bottom flask equipped with a magnetic stir bar and rubber septum. The vessel and its contents were purged with argon for 10 minutes at which point the materials were made into a slurry by the addition of anhydrous DCM (1 mL). 280 µL (1.81 mmol) of DIC was added dropwise to the reaction mixture via syringe over the course of approximately three minutes. The reaction was allowed to stir at room temperature for three hours at which point about 50% of the solvent was removed under vacuum. To the concentrated slurry was added 4 mL of chilled MeOH. The reaction was allowed to stir for several minutes to promote further precipitation followed by filtration into a Büchner funnel. Solids were washed with more chilled MeOH and then chilled MTBE. Isolated solids were dried under high vacuum to afford 110.8 mg (0.22 mmol, 38% yield) of 20-(Boc-Gly)-CPT (21).

Boc-Gly-OH can be substituted with other Boc-protected amino acids and dipeptides in the above procedure. By substituting Boc-Ala-OH, Boc-β-Ala-OH, Boc-Val-OH, Boc-GABA-OH and Boc-Phe-Gly-OH, the same procedure has yielded 20-(Boc-Ala)-CPT (Compound 41), 20-(Boc-β-Ala)-CPT (Compound 42), 20-(Boc-Val)-CPT (Compound 40), 20-(Boc-GABA)-CPT (Compound 43), and 20-(Boc-Phe-Gly)-CPT (Compound 44), respectively.

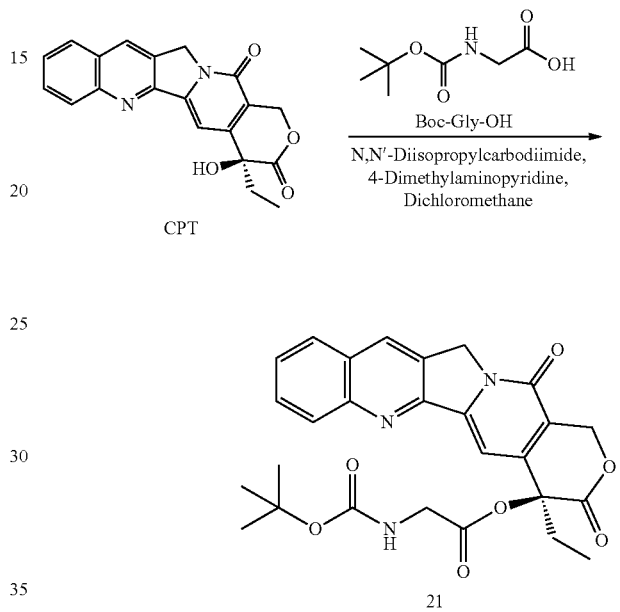

Example 31. Synthesis of 20-(TFA·Gly)-CPT (Compound 22)

To a scintillation vial charged with a magnetic stirrer and vent needle was added 97.1 mg (0.20 mmol) 20-(Boc-Gly)-CPT (21). A stirred suspension was produced by the addition of DCM (0.2 mL). Under stirring, TFA (0.2 mL) was gradually added. The reaction mixture was allowed to stir for 2 hours. After 2 hours, the product was precipitated with MTBE, filtered, and washed. The isolated sample was dried under high vacuum to afford 82.5 mg (0.16 mmol, 83% yield) of 20-(TFA·Gly)-CPT (22).

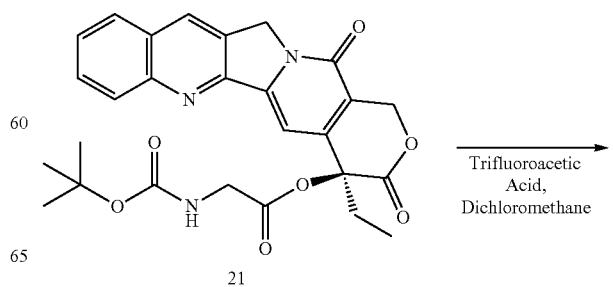

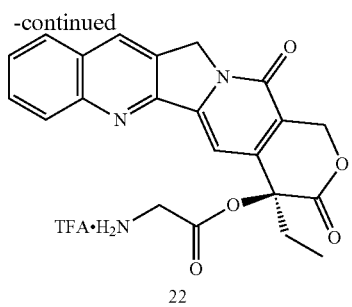

22

Substitution, in the method described above, of 20-(Boc-Gly)-CPT with 20-(Boc-Ala)-CPT, 20-(Boc-β-Ala)-CPT, 20-(Boc-Val)-CPT, 20-(Boc-GABA)-CPT and 20-(Boc-Phe-Gly)-CPT yields 20-(TFA·Ala)-CPT (Compound 45), 20-(TFA·β-Ala)-CPT (Compound 46), 20-(TFA·Val)-CPT (Compound 47), 20-(TFA·GABA)-CPT (Compound 48) and 20-(TFA·Phe-Gly)-CPT (Compound 49), respectively.

Example 32. Synthesis of MAP-Gly-CPT (Compound 23)

149.2 mg (0.07 mmol on CO$_2$H basis) of MAP (6) and 21.5 mg 20-(TFA·Gly)-CPT (22) (0.04 mmol) were added to a 20 mL scintillation vial charged with a magnetic stirrer. The vessel headspace was allowed to vent with an argon atmosphere for approximately 30 minutes, and then sealed under argon. Vial contents were dissolved under stirring following the addition of anhydrous DMSO (~9 mL, ~85% total reaction volume). An 8 mL scintillation vial charged with 166.3 mg of (7-azabenzotriazol-1-yloxy)trispyrrolidinophosphonium hexafluorophosphate (PyAOP, 0.32 mmol, 4.4 eq) and a magnetic stirrer was allowed to purge under an argon atmosphere. Contents of this vessel were dissolved in anhydrous DMSO (~3.2 mL) under stirring. Once all solids in both vessels had dissolved, 1.6 mL of the PyAOP solution (83.2 mg PyAOP, 0.16 mmol PyAOP, ~15% total reaction volume) was transferred to the polymer containing vessel. The reaction was allowed to stir for about 2 minutes at which point anhydrous ~45 µL (0.26 mmol) DIPEA (targeted 31.3 µL, 0.18 mmol) was added. The reaction vessel was allowed to stir in the dark at room temperature for approximately 18 hours. After 18 hours, the reaction vessel was removed from the argon atmosphere and about ⅓ of the reaction contents were transferred to a 50 mL glass centrifuge tube. The reaction was precipitated by slow addition of cold ethyl acetate (EtOAc) (0-4° C.). The suspension was allowed to stir for ~30 minutes at 0-4° C. followed by centrifugation. The EtOAc layer was decanted off, and the next ⅓ of the reaction medium was added to the same vessel. The procedure was repeated until all of the reaction media had been precipitated into the same tube. The precipitated solids were washed with chilled EtOAc (×5 volume) a total of 3 times with vortexed agitation to resuspend solids. After the final wash cycle, the last of EtOAc was decanted off, and solids were frozen in the centrifuge tube using liquid nitrogen. The frozen centrifuge tube was exposed to high vacuum for ~3 hours to dry the solid and afford 115.2 mg (quantitative yield) of MAP-Gly-CPT (23).

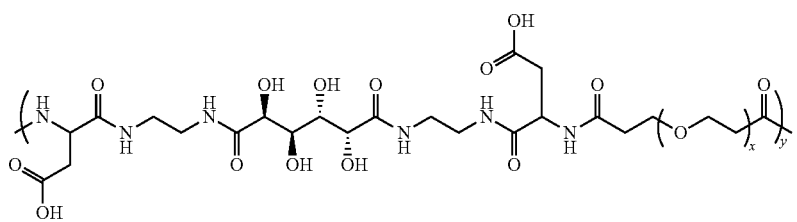

6

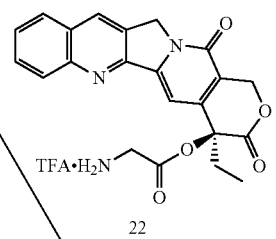

(7-Azabenzotriazol-1-yloxy)trispyrrolidinophosphonium hexafluorophosphate (PyAOP)
Diisopropylethylamine,
Dimethylsulfoxide

22

-continued
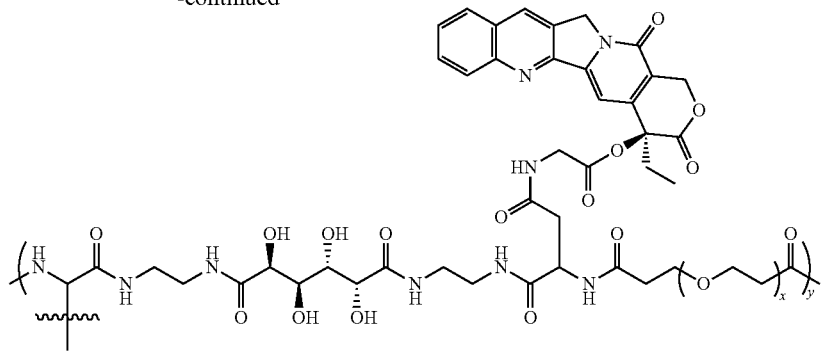
23
MAP-CPT conjugates are also produced by the same method using 20-(TFA·Ala)-CPT, 20-(TFA·β-Ala)-CPT, 20-(TFA·Val)-CPT, 20-(TFA·GABA)-CPT or 20-(TFA·Phe-Gly)-CPT as starting material, instead of 20-(TFA·Gly)-CPT, to generate MAP-Ala-CPT (Compound 50), MAP-β-Ala-CPT (Compound 51), MAP-Val-CPT (Compound 52), MAP-GABA-CPT (Compound 53) and MAP-Phe-Gly-CPT (Compound 54).
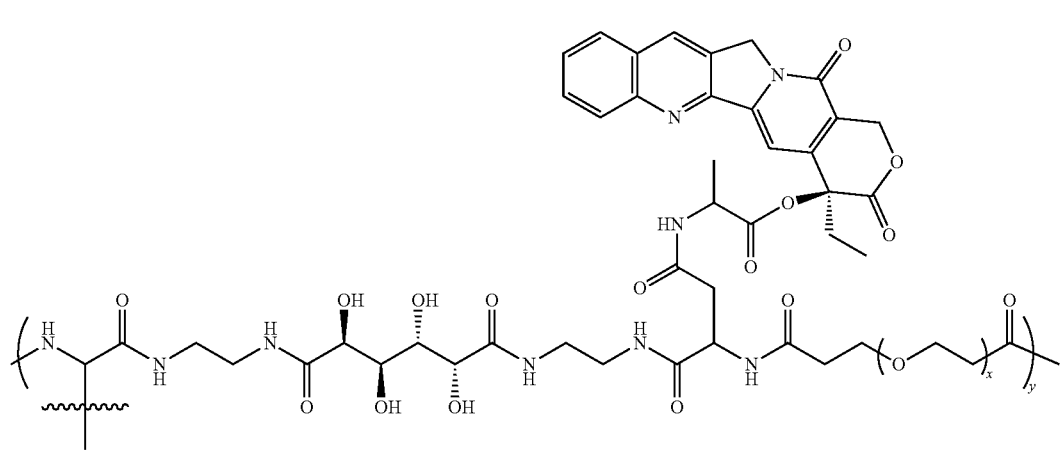
MAP-Ala-CPT
50
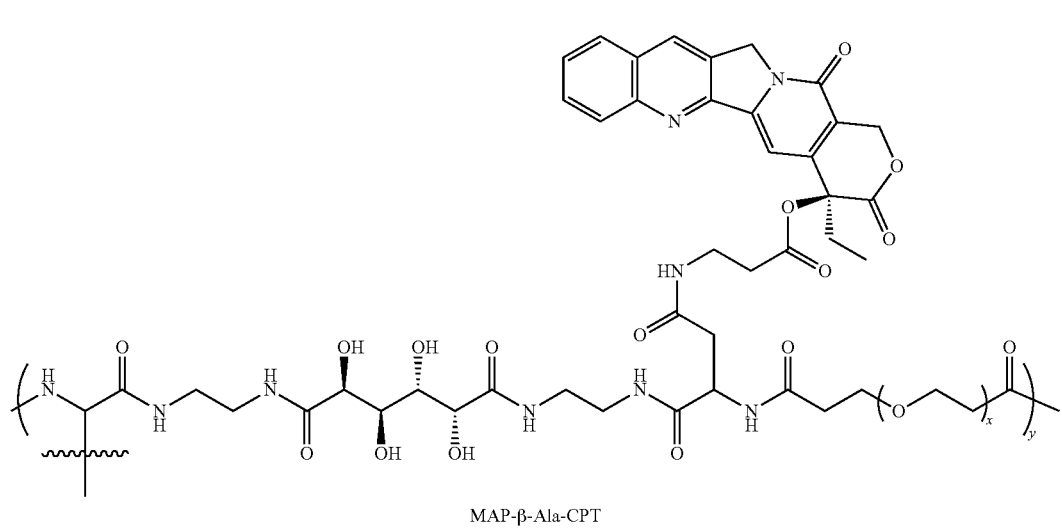
MAP-β-Ala-CPT
51

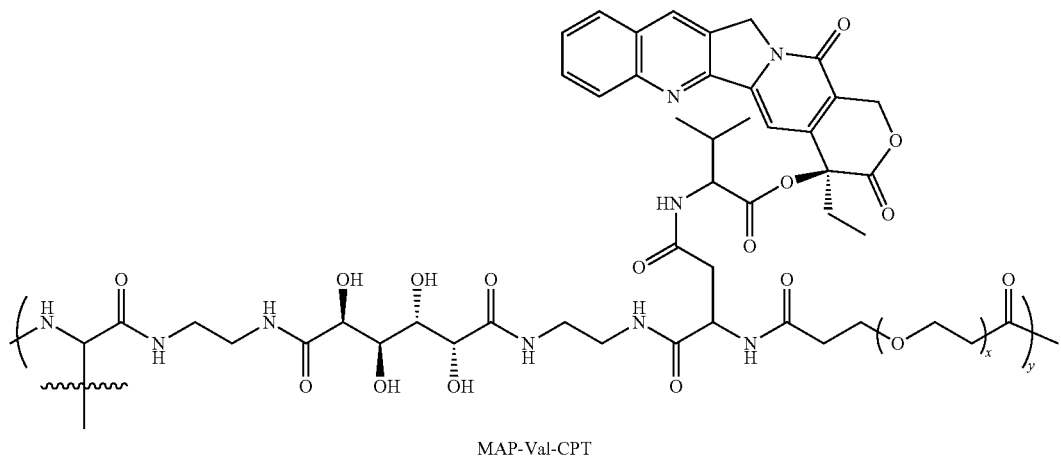
MAP-Val-CPT
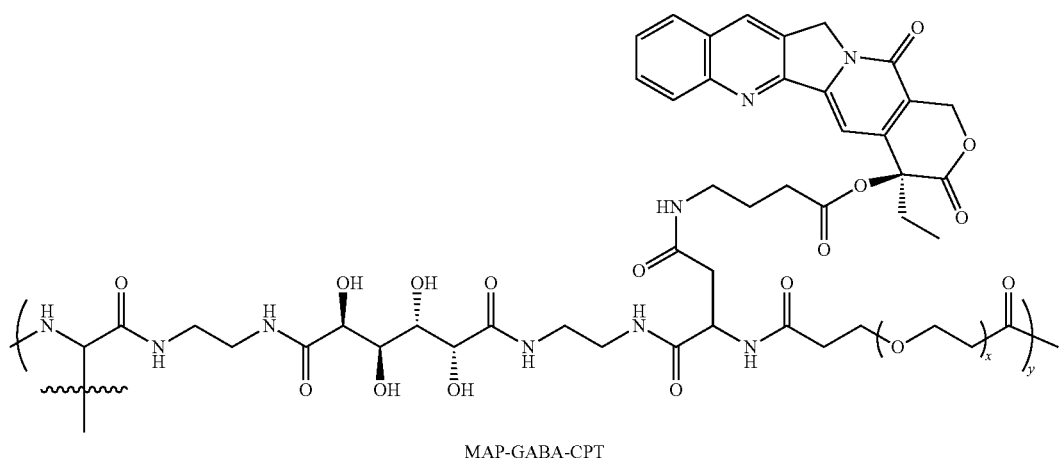
MAP-GABA-CPT
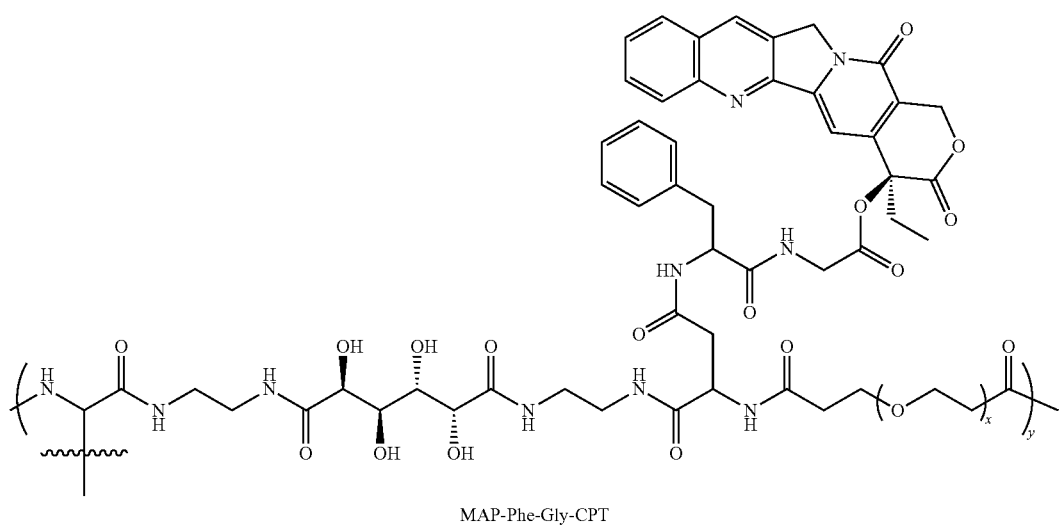
MAP-Phe-Gly-CPT

Example 33. Synthesis of 10-OBoc-SN38 (Compound 24)

A reaction vessel was charged with 2.0 g (5.10 mmol) SN38 under an argon atmosphere. 204 mL anhydrous DCM was added to the reaction vessel followed by 12.2 mL (151 mmol) anhydrous pyridine and 1.5 mL (6.53 mmol) di-tert-butyl dicarbonate. The reaction was allowed to stir for approximately 16 hours at room temperature at which point the reaction was filtered over Celite 545 (filtration aid), and washed with 0.5 N HCl and saturated sodium bicarbonate solution. The organic phase was dried over magnesium sulfate and concentrated under vacuum. The reaction mixture was diluted into DCM, and subsequently precipitated into hexanes. The solids were filtered and dried under vacuum to afford 2.2 g (4.47 mmol, 88% yield) of 10-OBoc-SN38 (24).

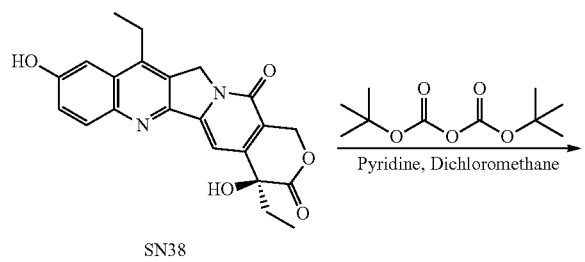

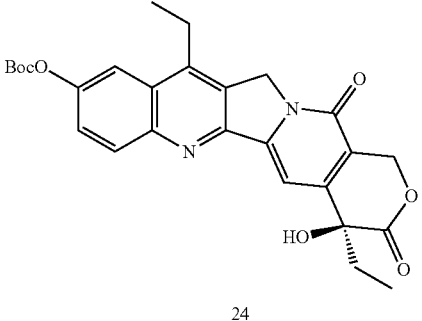

24

Example 34. Synthesis of 20-(Boc-Gly)-10-OBoc-SN38 (Compound 25)

To a reaction vessel cooled to 0° C., under an argon atmosphere, charged with 502 mg (1.02 mmol) 10-OBoc-SN38 (24) was added 8.8 mL DCM. To this reaction vessel a chilled solution comprising 3.8 mL DCM, 447 mg (2.55 mmol) Boc-Gly-OH, 489 mg (2.55 mmol) EDC·HCl, and 125 mg (1.02 mmol) DMAP was added. The reaction was allowed to stir at 0° C. for 3 hours. The reaction was washed with 0.5% sodium bicarbonate solution, water, 0.1 N HCl, and brine. The organic phase was dried over magnesium sulfate and evaporated under vacuum to afford 639 mg (0.98 mmol, 97% yield) 20-(Boc-Gly)-10-OBoc-SN38 (25).

Boc-Gly-OH can be substituted with other Boc-protected amino acids in the above procedure. By substituting Boc-Ala-OH, Boc-β-Ala-OH, Boc-Val-OH and Boc-Leu-OH as starting material, the same procedure has yielded 20-(Boc-Ala)-10-OBoc-SN38 (Compound 29), 20-(Boc-β-Ala)-10-OBoc-SN38 (Compound 30), 20-(Boc-Val)-OBoc-SN38 (Compound 31) and 20-(Boc-Leu)-10-OBoc-SN38 (Compound 35), respectively.

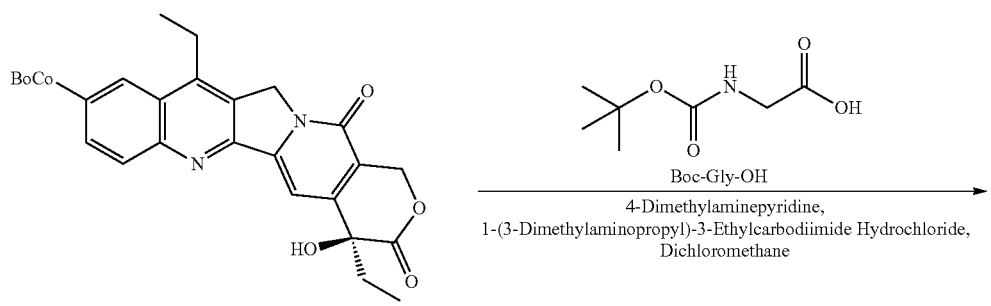

24

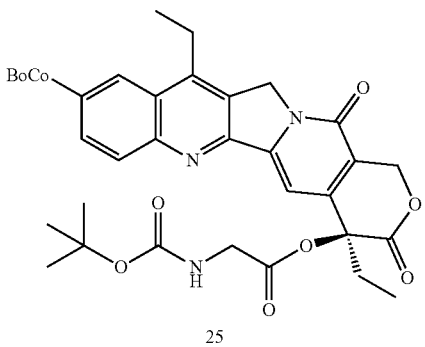

25

Example 35. Synthesis of 20-(TFA·Gly)-SN38 (Compound 26)

To a reaction vessel charged with 250 mg (0.38 mmol) of 20-(Boc-Gly)-10-OBoc-SN38 (25) and 1.88 mL DCM was added 0.47 mL (6.14 mmol) TFA. The reaction was allowed to stir at RT for 2.5 hours. The reaction mixture was precipitated into chilled (4° C.) MTBE, isolated by centrifugation, washed again with MTBE, and dried under vacuum to afford 133 mg (0.24 mmol, 61% yield) 20-(TFA·Gly)-SN38 (26).

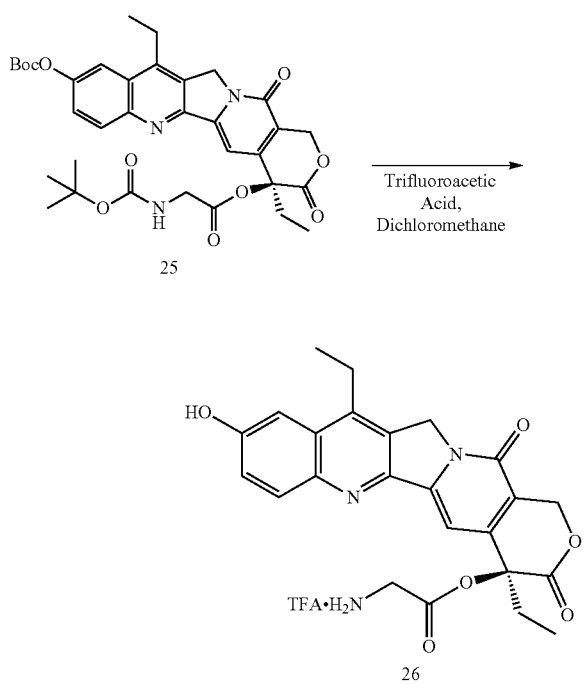

20-(Boc-Gly)-10-OBoc-SN38 was substituted, as starting material, by 20-(Boc-Ala)-10-OBoc-SN38, 20-(Boc-β-Ala)-10-OBoc-SN38, 20-(Boc-Val)-10-OBoc-SN38 and 20-(Boc-Leu)-10-OBoc-SN38 to yield 20-(TFA·Ala)-SN38 (Compound 32), 20-(TFA·β-Ala)-SN38 (Compound 33), 20-(TFA·Val)-SN38 (Compound 34) and 20-(TFA·Leu)-SN38 (Compound 36), respectively.

The foregoing TFA salts of amino acid-linked SN38 derivatives can be used to form MAP-SN38 conjugates as described in Examples 17 and 18.

Example 36. Synthesis of NPBA-PEG$_{5k}$-AA (Compound 27)

A 250 mL round bottom flask with 20 g (4 mmol) of NH$_2$-PEG$_{5k}$-acetic acid (AA) hydrochloride, DIPEA (2.1 mL, 12 mmol) was charged with anhydrous DCM (40 mL) and flushed with argon. The solution was cooled in ice/water bath. In 20 mL vial with magnetic stir bar, 934 mg (5.5 mmol) of 3-carboxy-5-nitrophenylboronic acid (NPBA) was dissolved in anhydrous DCM/dimethyl formamide (DMF) (8 mL, 4:1 v/v). 1038 mg (5.25 mmol) of N-ethoxycarbonyl-2-ethoxy-1,2-dihydroquinoline (EEDQ) was added to the solution of NPBA. The activated acid was stirred for 15 minutes, then added dropwise to the precooled solution of PEG-amines in DCM. The reaction mixture was stirred for 20 minutes at 0° C. Deionized water (100 mL) was added to the reaction mixture, which was stirred vigorously and warmed to room temperature. At this stage, pH of the reaction mixture was 9. Subsequently, monosodium phosphate (NaH$_2$PO$_4$, 2.5 g) was added to obtain a pH of 7. Addition of 1 M HCl (12 mL) further reduced the pH of the reaction mixture to 4. The reaction mixture was transferred to separatory funnel and isopropyl acetate (iPrOAc, 100 mL) was added. The mixture was shaken well and allowed to settle to obtain the separated phases. The organic phase was discarded, and extraction was repeated with iPrOAc (3×100 mL). Aqueous phase was transferred to a 250 mL round bottom flask and concentrated on a rotary evaporator at room temperature at 20 Torr for 30 minutes. The aqueous solution was lyophilized to afford a powder. Lyophilized powder was dissolved in DMSO/water (40 mL, 3:1 v/v). The solution was purified by Hydrophobic Interaction Chromatography on a C18Aq Teledyne ISCO column (475 g) preequilibrated with 95% mobile phase A (water+0.05% TFA) and 5% mobile phase B (ACN+0.05% TFA), in 12-15 mL injections. The gradient was run from 5% B to 40% B before the column was washed and subsequent injections were carried out. The purification was repeated for the rest of product solution. The product-containing fractions were analyzed by HPLC. Fractions with purity >99.5% were combined and lyophilized to afford 14.2 g (2.71 mmol, 68% yield) of NPBA-PEG$_{5k}$-AA (27).

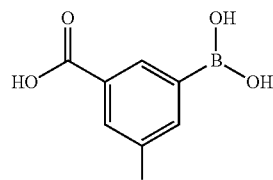

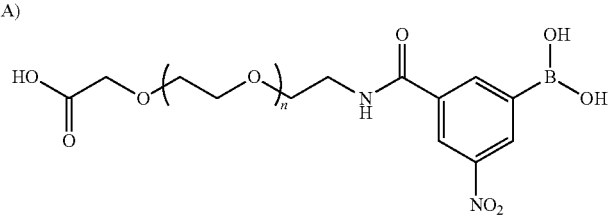

3-carboxy-5-nitrophenylboronic acid (NPBA)

1. N-ethoxycarbonyl-2-ethoxy-1,2-dihydroquinoline
   Dichloromethane, Dimethylformamide
2. HCl·NH$_2$—PEG$_{5k}$—COOH
   N,N-Diisopropylethylamine, Dichloromethane

27

For Compound 27 synthesized by this method, n was about 114. These values will change if a different starting material (e.g., NH$_2$-PEG$_{3.5k}$-AA) is used (e.g., n is about 80 for 3.5 kDa PEG).

Example 37. Synthesis of NPBA-PEG$_{5k}$-AA-PFP (Compound 28)

To an 8 mL reaction vessel was added 301.8 mg (0.06 mmol) NPBA-PEG$_{5k}$-AA (27) along with a magnetic stir bar. The reaction vessel was purged with vacuum and argon cycles in triplicate. Solids were dissolved in anhydrous DCM (1.2 mL) after which 35 μL of anhydrous N-methylmorpholine (0.35 mmol) was added via syringe. The reaction vessel was opened briefly and 45.3 mg of bis(pentafluorophenyl) carbonate (0.12 mmol) was added. The reaction headspace was purged with argon, and the reaction was allowed to stir at room temperature for approximately 2 hours. The reaction solution was added dropwise to a stirred volume of MTBE (25 mL) to facilitate precipitation. The mixture was allowed to stir for 30 minutes under an argon atmosphere before centrifugation at 2600 g. The liquid layer was decanted at which point heptane (20 mL) was added to the centrifuge tube. The sample was mechanically agitated prior to a second round of centrifugation at 2600 g (8 minutes). Liquid was decanted from the vessel to leave remaining wet solids. The vessel was cooled briefly in liquid nitrogen and then pumped using a Schlenk line to remove solvents to afford 300 mg (0.055 mmol, 96% yield) of NPBA-PEG$_{5k}$-AA-PFP (28).

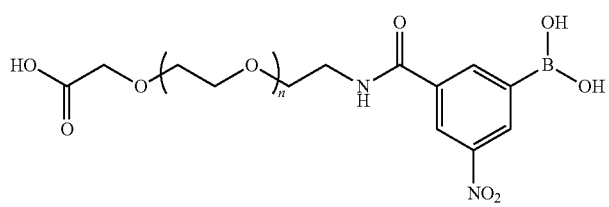
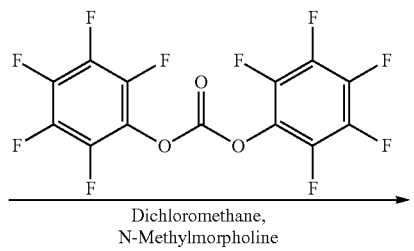

Dichloromethane, N-Methylmorpholine

27

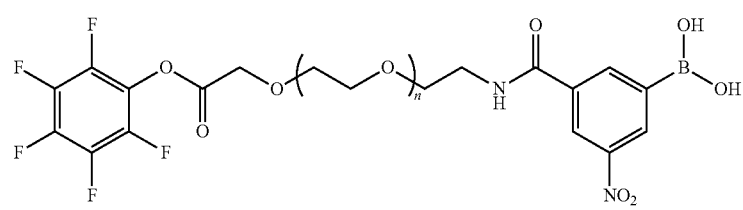

28

As stated in Example 36, n was about 114 for Compounds 27 and 28.

Example 38. Synthesis of NPBA-PEG$_{5k}$-Tf Crude Mixture

A reaction vessel was charged with 35 g (0.440 mmol) holo-transferrin (Tf) and 1.75 L of 50 mM HEPES (pH 7.8) was added slowly to dissolve Tf at a concentration of 20 g/L. Following solubilization, 4.77 g (0.881 mmol) of NPBA-PEG$_{5k}$-AA-PFP (28) in 44 mL DMSO was added slowly to the reaction mixture and mixed well. The reaction mixture was incubated at room temperature for 2 hours. The crude reaction mixture was analyzed on an Agilent 1290 HPLC system with a reverse phase (RP) column (Zorbax 300SB-CN 4.6 mm ID×150 cm) with a mobile phase A (water+0.1% TFA) and mobile phase B (ACN/IPA (4:1 v/v)+0.1% TFA) at a flow rate of 0.7 mL/min. The column was connected to an absorbance detector set to a 280 nm wavelength and reference at 360 nm wavelength. In addition, the crude reaction mixture was analyzed on an Agilent 1290 HPLC system with a hydrophobic interaction chromatography (HIC) column (TSK gel Butyl-NPR 4.6 mm ID×3.5 cm) with a mobile phase A (20 mM sodium phosphate, 1.5 M ammonium sulfate, pH 7.0) and mobile phase B (20 mM sodium phosphate, pH 7.0/IPA (4:1 v/v)) at a flow rate of 0.8 mL/min. The column was connected to an absorbance detector set to a 280 nm wavelength signal and reference at 360 nm. After 2 hours incubation, the crude reaction mixture was ready for HIC purification.

Example 39. Isolation of Mono-NPBA-PEG$_{5k}$-Tf 1.75 L of NPBA-PEG$_{5k}$-Tf crude mixture (20 g/L) was added to a reaction vessel. 7 L of mobile phase A (1.5 M ammonium sulfate, 20 mM sodium phosphate, pH 7.4) was added to crude mixture to achieve a 1.2 M ammonium sulfate, 16 mM sodium phosphate, pH 7.4 concentration. After mixing, sample mixture was loaded onto an AxioChrom 140 column (1.7 L) packed with GE Sepharose Phenyl High Performance HIC resin with a pump flow rate of 200 mL/min. Approximately 10 minutes of residence time was allowed for loading the sample mixture onto the HIC column. IPA/10 mM sodium phosphate, pH 7.4 (1:4 v/v, mobile phase B) was used as the eluent. Prior to the elution step, column was washed with 20% mobile phase B for 2 column volumes (CV) to remove unbound species. Purified NPBA-PEGk-Tf was eluted with gradient 20-100% mobile phase B over 15 CV. Fractions of mono-PEGylated Tf (mono-NPBA-PEGk-Tf) were collected and combined for ultrafiltration and diafiltration (UF/DF). Sartocon Slice Hydrosart Cassette 30 kDa membrane was used for UF/DF of mono-NPBA-PEG$_{5k}$-Tf. Mono-NPBA-PEG$_{5k}$-Tf conjugate was concentrated to 50 g/L by diafiltration using 7 volumes of PBS pH 7.4. After that, mono-NPBA-PEGk-Tf was sterile filtered through a 0.22 μm polyethersulfone (PES) membrane.

Example 40. Determination of Number of NPBA Per Tf

The number of NPBA per Tf in mono-NPBA-PEGk-Tf was determined by calculating the ratio between the molar concentration of NPBA-PEGk in mono-NPBA-PEG$_{5k}$-Tf and the molar concentration of Tf using the Alizarin Red S (ARS) detection assay for NPBA. To prepare a standard curve, NPBA-PEG$_{5k}$-AA (27) samples were prepared at varying concentrations (0-0.0098 mM) dissolved in PBS, pH 7.2. ARS was prepared at 0.049 mM dissolved in water. Samples were then mixed with ARS, and fluorescence was measured (Ex: 468 nm, Em: 572 nm) using a Varioskan LUX Spectrophotometer (ThermoFisher) and SkanIt (Thermo Fisher) or a similar fluorescence analysis software. Linear regression of these data (fluorescence v. concentration) provided a calibration curve for determination of NPBA in samples of interest.

Samples of interest (e.g., Tf and mono-NPBA-PEG$_{5k}$-Tf) were prepared at 0.007 mM dissolved in PBS, pH 7.2. Molar concentrations of NPBA-PEGk in mono-NPBA-PEGk-Tf were calculated from average fluorescence values of mono-NPBA-PEG$_{5k}$-Tf samples and the calibration curve of fluorescence values for varied known concentrations of NPBA-PEGk-AA standards (0-0.0098 mM) using the following equation:

$$\text{Fluorescence} = \varepsilon \ast C_N + b$$

in which ε=slope of linear regression of calibration curve, b=intercept of the linear regression of the calibration curve and $C_N$=concentration of NBPA-PEG (mM). Therefore, $C_N$ (mM)=(Fluorescence−b)/ε.

The number of NPBA per Tf ($N_{Tf}$) was then calculated by dividing $C_N$ by the known concentration of Tf according the following equation:

$$N_{Tf} = (\text{NPBA-PEG}_{5k}\text{ mmol/L})/(\text{Tf mmol/L})$$

The determined number of NPBA in mono-NPBA-PEG$_{5k}$-Tf using the ARS detection assay of NPBA was 1 NPBA per Tf in mono-NPBA-PEG$_{5k}$-Tf. Reaction with ARS, and therefore fluorescent signal, requires NPBA functional groups that are available for reaction. Some molecules (e.g. citrate) complex with NPBA, decreasing fluorescent signal and altering the measured number of NPBA per mono-NPBA-PEG$_{5k}$-Tf. In other cases, excess unreacted NPBA-PEG conjugate may be present in crude samples, increasing the fluorescent signal and altering the determined number of NPBA per mono-NPBA-PEG$_{5k}$-Tf. Exemplary experimental results are shown in Table 2.

TABLE 2

Number of NPBA per Tf for Mono-NPBA-PEG$_{5k}$-Tf Samples

| Sample | $C_N$ (mM) | $N_{Tf}$ = (NPBA per Tf) |
| --- | --- | --- |
| Mono-NPBA-PEG$_{5k}$-Tf (+ citrate) | 6.40E-03 | 0.91 |
| Mono-NPBA-PEG$_{5k}$-Tf (− citrate) | 7.34E-03 | 1.05 |

Example 41. Synthesis of NPBA-PEG$_{5k}$-Tras Crude Mixture 5.5 g (0.038 mmol) of Trastuzumab was buffer exchanged with 50 mM HEPES (pH 7.8) and the final protein concentration was adjusted to 10 g/L. Following solubilization, 409.07 mg (0.076 mmol) of NPBA-PEG$_{5k}$-AA-PFP (28) in 3.78 mL in DMSO was added slowly to the reaction mixture and mixed well. The reaction mixture was incubated at room temperature for 2 hours. Crude reaction mixture was analyzed on an Agilent 1290 HPLC system with a reverse phase (RP) column (Zorbax 300SB-CN 4.6 mm ID×150 cm) with a mobile phase A (water+0.1% TFA) and mobile phase B (ACN/IPA (4:1 v/v)+0.1% TFA) at a flow rate of 0.7 mL/min. The column was connected to an absorbance detector set to a 280 nm signal and reference at 360 nm. After 2 hours incubation, the crude reaction mixture was ready for HIC purification.

Example 42. Isolation of Mono-NPBA-PEG$_{5k}$-Tras 0.55 L of NPBA-PEG$_{5k}$-Tras crude mixture (10 g/L) was added to a reaction vessel. 1.1 L of mobile phase A (1.5 M ammonium sulfate, 20 mM sodium phosphate, pH 7.4) was added to crude mixture to achieve a 1 M ammonium sulfate, 13.3 mM sodium phosphate, pH 7.4 concentration. After mixing, sample mixture was loaded onto an AxioChrom 140 column (1.7 L) packed with GE Sepharose Phenyl High Performance HIC resin at a flow rate of 200 mL/min. Approximately 10 minutes of residence time was allowed for loading the sample mixture onto the HIC column. IPA/10 mM sodium phosphate, pH 7.4 (1:4 v/v, mobile phase B) was used as the eluent. Prior to the elution step, the column was washed with two CV of 40% mobile phase B to remove unbound species. Purified NPBA-PEG$_{5k}$-Tras was eluted with a gradient of 40-100% mobile phase B over 15 CV. Fractions of mono-PEGylated Tras (mono-NPBA-PEGk-Tras) were collected and combined for UF/DF. Sartocon Slice Hydrosart Cassette 30 kDa membrane was used for UF/DF of mono-NPBA-PEGk-Tras. Mono-NPBA-PEGk-Tras conjugate was concentrated to 50 g/L by diafiltration using 7 volumes of PBS pH 7.4. Following diafiltration, mono-NPBA-PEGk-Tras was sterile filtered through a 0.22 μm PES membrane.

Example 43. Determination of Number of NPBA Per Tras

The number of NPBA per Tras in mono-NPBA-PEGk-Tras was determined by calculating the ratio between the molar concentration of NPBA-PEGk in mono-NPBA-PEGk-Tras and the molar concentration of Tras using the ARS detection assay for NPBA. To prepare a standard curve, NPBA-PEGk-AA (27) samples were prepared at varying concentrations (0-0.0098 mM) dissolved in PBS, pH 7.2. ARS was prepared at 0.049 mM dissolved in water. Samples were then mixed with ARS, and fluorescence was measured (Ex: 468 nm, Em: 572 nm) using a Varioskan LUX Spectrophotometer (ThermoFisher) and SkanIt (Thermo Fisher) or a similar fluorescence analysis software. Linear regression of these data (fluorescence v. concentration) provided a calibration curve for determination of NPBA in samples of interest.

Samples of interest (e.g., Tras and mono-NPBA-PEGk-Tras) were prepared at 0.007 mM dissolved in PBS, pH 7.2. Molar concentrations of NPBA-PEG in mono-NPBA-PEGk-Tras were calculated from average fluorescence values of mono-NPBA-PEGk-Tras samples and the calibration curve of fluorescence values for varied known concentrations of NPBA-PEGk-AA standards (0-0.0098 mM) using the following equation:

$$\text{Fluorescence} = \varepsilon \ast C_N + b$$

in which ε=slope of linear regression of calibration curve, b=intercept of the linear regression of the calibration curve and $C_N$=concentration of NBPA-PEG (mM). Therefore, $C_N$ (mM)=(Fluorescence−b)/ε.

The number of NPBA per Tras ($N_{Tras}$) was then calculated by dividing $C_N$ by the known concentration of Tras according the following equation:

$$N_{Tras} = (\text{NPBA–PEG mmol/L})/(\text{Tras mmol/L})$$

The determined number of NPBA in mono-NPBA-PEG$_{5k}$-Tras using the ARS detection assay of NPBA was ~1 NPBA per Tras in mono-NPBA-PEG$_{5k}$-Tras. As described in Example 40, the number of NPBA per mono-NPBA-PEG$_{5k}$-Tras can be altered by undesired complexation of molecules with NPBA, which decreases fluorescent signal, or by the presence of excess unreacted NPBA-PEG conjugate in crude samples, which increases fluorescent signal. Exemplary experimental results are shown in Table 3.

TABLE 3

Number of NPBA per Tras for Mono-NPBA-PEG$_{5k}$-Tras Samples

| Sample | $C_N$ (mM) | $N_{Tras}$=(NPBA per Tras) |
|---|---|---|
| Mono-NPBA-PEG$_{5k}$-Tras (crude) | 1.15E-02 | 1.64 |
| Mono-NPBA-PEG$_{5k}$-Tras (purified) | 7.05E-03 | 1.01 |

As those skilled in the art will appreciate, numerous modifications and variations of the present disclosure are possible in light of these teachings, and all such are contemplated hereby. For example, in addition to the embodiments described herein, the present disclosure contemplates and claims those inventions resulting from the combination of features of the disclosure cited herein and those of the cited prior art references which complement the features of the present disclosure. Similarly, it will be appreciated that any described material, feature, or article may be used in combination with any other material, feature, or article, and such combinations are considered within the scope of this disclosure.

The disclosures of each patent, patent application, and publication cited or described in this document are hereby incorporated herein by reference, each in its entirety, for all purposes, or at least for the contents related to the context in which it was cited. In addition to the references already mentioned, the present disclosure contains subject matter related to U.S. patent application Ser. No. 12/540,319, filed Aug. 12, 2009, now U.S. Pat. No. 8,557,292; Ser. No. 13/782,458, filed Mar. 1, 2013; Ser. No. 13/782,486, filed Mar. 1, 2013; Ser. No. 13/852,303, filed: Mar. 28, 2013; Ser. No. 15/180,201, filed Jun. 13, 2016, now U.S. Pat. No. 10,287,401; and International Application No. PCT/US2009/053620, filed Aug. 12, 2009, the contents of which are incorporated by reference for all purposes.

What is claimed is:

1. A mucic acid polymer (MAP)-camptothecin (CPT) conjugate consisting essentially of repeating subunits of:

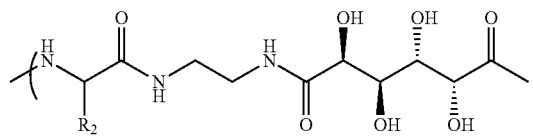

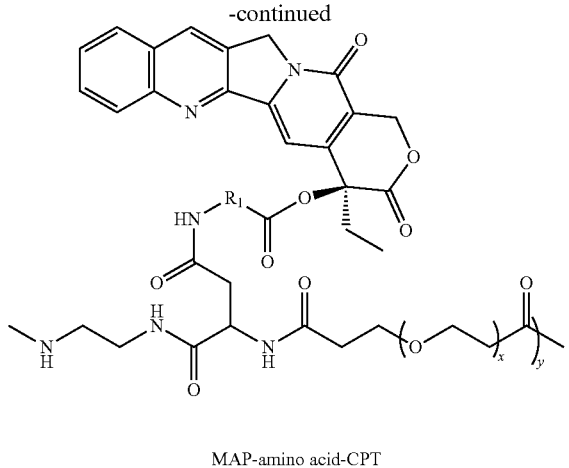

MAP-amino acid-CPT wherein:

R₁ is one or more α-carbon atoms of an amino acid bonded to an amino acid functional group, wherein the amino acid functional group is selected from functional groups of alanine, β-alanine, valine, gamma-aminobutyric acid (GABA) and the dipeptide phenylalanine-glycine, R₂ is

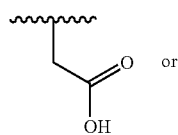 or x is between 20 and 200; and
y is between 5 and 200.

2. A nanoparticle comprising the MAP-CPT conjugate of claim 1.

3. The conjugate of claim 1, wherein the functional group is the functional group of alanine.

4. The conjugate of claim 1, wherein the functional group is the functional group of β-alanine.

5. The conjugate of claim 1, wherein the functional group is the functional group of valine.

6. The conjugate of claim 1, wherein the functional group is the functional group of gamma-aminobutyric acid (GABA).

7. The conjugate of claim 1, wherein the functional group is the functional group of the dipeptide phenylalanine-glycine.

8. The conjugate of claim 1, wherein x is about 114.

9. The conjugate of claim 1, wherein x is about 80.

10. The conjugate of claim 1, wherein x is about 46.

11. The conjugate of claim 1, wherein y is about 16.

12. A mucic acid polymer (MAP)-camptothecin (CPT) conjugate consisting essentially of repeating subunits of:

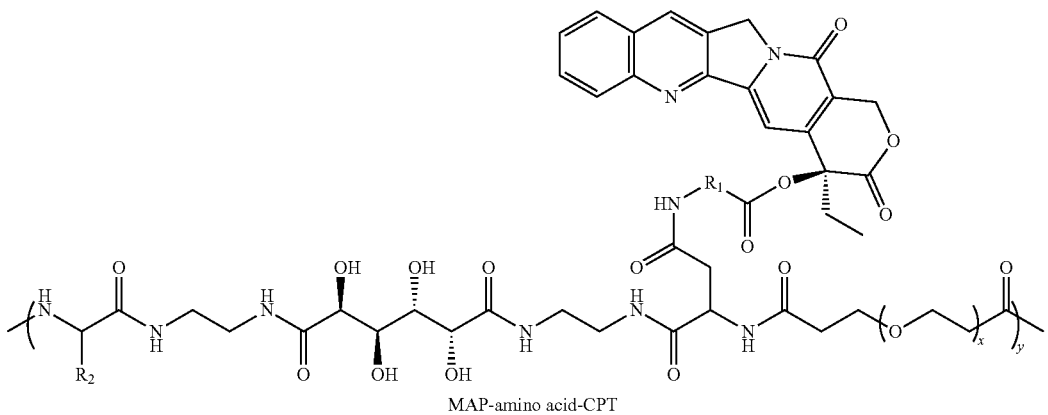

MAP-amino acid-CPT wherein:
R₁ is one or more α-carbon atoms of an amino acid bonded to an amino acid functional group, wherein the amino acid functional group is selected from functional groups of alanine, β-alanine, valine, gamma-aminobutyric acid (GABA) and the dipeptide phenylalanine-glycine,
R₂ is

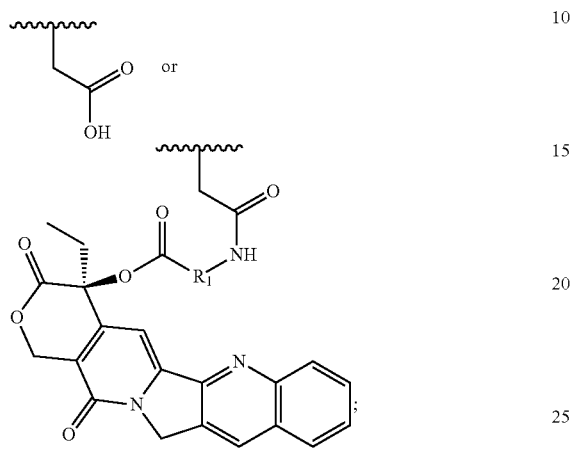

x is between 20 and 200; and
y is between 5 and 200;
to which is conjugated transferrin.

13. A nanoparticle comprising the conjugate of claim 12.

14. A mucic acid polymer (MAP)-camptothecin (CPT) conjugate consisting essentially of repeating subunits of:

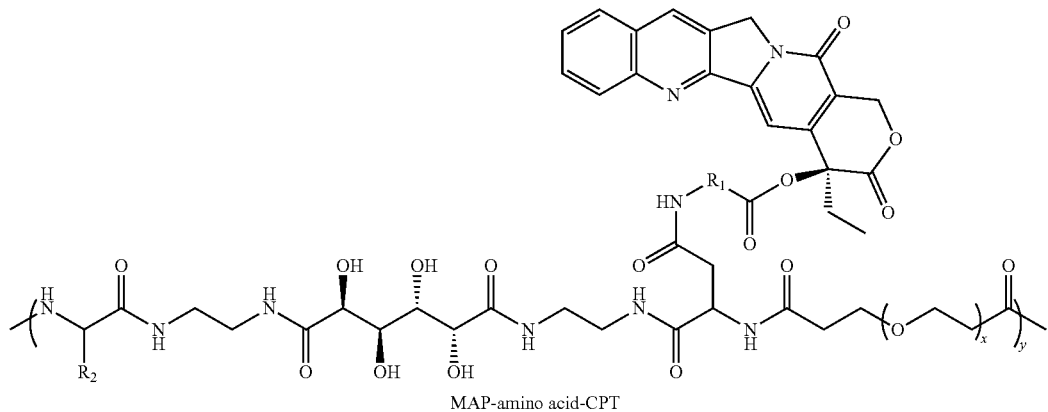

MAP-amino acid-CPT wherein:

R₁ is one or more α-carbon atoms of an amino acid bonded to an amino acid functional group, wherein the amino acid functional group is selected from functional groups of alanine, β-alanine, valine, gamma-aminobutyric acid (GABA) and the dipeptide phenylalanine-glycine, R₂ is

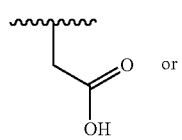 or

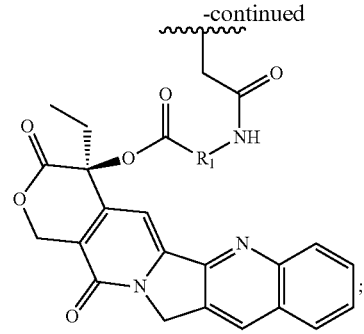

x is between 20 and 200; and
y is between 5 and 200;
to which is conjugated an antibody.

15. The conjugate of claim 14, wherein the antibody is trastuzumab.

16. A nanoparticle comprising the MAP-CPT conjugate of claim 14.

17. A nanoparticle comprising the MAP-CPT conjugate of claim 15.

* * * * *